(12) United States Patent
Koide et al.

(10) Patent No.: US 9,885,050 B2
(45) Date of Patent: Feb. 6, 2018

(54) MOLECULAR AFFINITY CLAMP TECHNOLOGY AND USES THEREOF

(75) Inventors: Shohei Koide, Chicago, IL (US); Akiko Koide, Chicago, IL (US); Jin Huang, Chicago, IL (US)

(73) Assignee: The University of Chicago, Chicago, IL (US)

( * ) Notice: Subject to any disclaimer, the term of this patent is extended or adjusted under 35 U.S.C. 154(b) by 848 days.

(21) Appl. No.: 12/742,014

(22) PCT Filed: Nov. 10, 2008

(86) PCT No.: PCT/US2008/083021
§ 371 (c)(1),
(2), (4) Date: Dec. 15, 2010

(87) PCT Pub. No.: WO2009/062170
PCT Pub. Date: May 14, 2009

(65) Prior Publication Data
US 2011/0143963 A1    Jun. 16, 2011

Related U.S. Application Data

(60) Provisional application No. 60/986,475, filed on Nov. 8, 2007, provisional application No. 61/016,736, filed on Dec. 26, 2007.

(51) Int. Cl.
*C12N 15/62* (2006.01)
*C07K 14/78* (2006.01)
*G01N 33/542* (2006.01)

(52) U.S. Cl.
CPC ............. *C12N 15/62* (2013.01); *C07K 14/78* (2013.01); *G01N 33/542* (2013.01); *G01N 2333/71* (2013.01)

(58) Field of Classification Search
None
See application file for complete search history.

(56) References Cited

U.S. PATENT DOCUMENTS 6,180,341 B1 * 1/2001 Iverson .................. C07K 16/00
435/6.14
6,462,189 B1  10/2002 Koide .......................... 536/23.5
(Continued)

FOREIGN PATENT DOCUMENTS

WO    WO 01/64942    9/2001
WO    WO 02/04523    1/2002
WO    WO 08/066752   5/2008

OTHER PUBLICATIONS

Robert (1999) Int J Canc 81: 285-291.*
(Continued)

*Primary Examiner* — Melanie Y Brown
*Assistant Examiner* — Richard Moerschell
(74) *Attorney, Agent, or Firm* — Norton Rose Fulbright US LLP

(57) ABSTRACT

The invention provides a molecular affinity clamp. The architecture of the affinity clamp is modular with two biorecognition modules, each capable of binding a target motif. The first biorecognition module has a recognition domain that possesses inherent or natural specificity for the target motif. The second biorecognition module also has a recognition domain that binds the motif. The two biorecognition modules are tethered together either directly, e.g., via a peptide bond between the two modules, or indirectly, e.g., via a linker moiety or linker.

17 Claims, 17 Drawing Sheets

(56) References Cited

U.S. PATENT DOCUMENTS

| | | | |
|---|---|---|---|
| 6,673,901 B2 | 1/2004 | Koide | 530/380 |
| 6,703,199 B1 | 3/2004 | Koide | 506/14 |
| 6,818,418 B1* | 11/2004 | Lipovsek | C07K 14/78 |
| | | | 435/69.1 |
| 7,119,171 B2 | 10/2006 | Koide | 530/387.1 |
| 7,153,661 B2 | 12/2006 | Koide | 435/7.1 |
| 7,556,925 B2 | 7/2009 | Koide et al. | 435/7.1 |
| 7,598,352 B2 | 10/2009 | Koide | 530/388.9 |
| 2002/0025317 A1* | 2/2002 | Leung et al. | 424/145.1 |
| 2002/0090607 A1* | 7/2002 | Fields et al. | 435/5 |
| 2002/0197694 A1* | 12/2002 | Shao | C07K 16/00 |
| | | | 435/188.5 |
| 2003/0027209 A1* | 2/2003 | Huse | C12N 9/18 |
| | | | 435/7.1 |
| 2004/0005540 A1* | 1/2004 | Petrenko | G01N 33/569 |
| | | | 435/5 |
| 2004/0018570 A1* | 1/2004 | Sedivy | C12Q 1/485 |
| | | | 435/7.23 |
| 2004/0058400 A1* | 3/2004 | Holliger | C07K 16/1063 |
| | | | 435/7.23 |
| 2007/0196274 A1* | 8/2007 | Sun | 424/1.49 |
| 2007/0264234 A1* | 11/2007 | Sayers et al. | 424/93.2 |
| 2009/0087445 A1* | 4/2009 | Freund et al. | 424/185.1 |
| 2010/0227913 A1* | 9/2010 | Lyakhov et al. | 514/44 R |
| 2016/0024191 A1* | 1/2016 | Koide | C07K 16/00 |
| | | | 506/17 |

OTHER PUBLICATIONS

Law (2005) Immunoassay, a practical guide.*
Blasioli (1990) JBC 274: 2303-2307.*
Beebe (2000) Biochem 39: 13251-13260.*
Tenev (1997) JBC 272: 5966-5973.*
Berglund (2008) Prot Sci 17:606-613.*
Kaplan (1998) J Pep Res 52:249-260.*
Abbas eds (2007) Cellular and Molecular Bio, 6th Edition. pub by Sunders Elsevier, p. 1-566.*
Skerra (2000) J Mol Recog 13: 167-187.*
Abbas eds, Cellular and Molc Immun, (2007) p. 80, Saunders Elsevier pub.*
Nourry (2003) Science Stke vol. 2003, issue 179, p. 1-12.*
Skerra (2000) J Mol Recog 13:167-187.*
Webster's dictionary citation on-line.*
Koide 1998 JMB 284:1141-1151.*
Appleton et al., "Comparative structural anaylysis of Erbin PDZ domain and the first PDZ domain of ZO-1. Insights into the determinants of PDZ domain specificity," *J Biol Chem*, 281:22312-22320, 2006.
Asian et al., "Engineered single-chain dimeric streptavidins with an unexpected strong preference for biotin-4-fluorescein," *Proc Natl Acad Sci U S A* 102:8507-12, 2005.
Baird et al., "Circular permutation and receptor insertion within green fluorescent proteins," *Proc Natl Acad Sci U S A*, 96:11241-6, 1999.
Batori et al., "Exploring the potential of the of the monobody scaffold: effects of loop elongation on the stability of a fibronectin type III domain," *Protein Eng*, 15:1015-20, 2002.
Binz et al., "Engineered proteins as specific binding reagents," *Curr Opin Biotechnol*, 16:459-69, 2005.
Binz et al., "Engineering novel binding proteins from nonimmunoglobulin domains," *Nat. Biotechnol*, 23:1257-1268, 2005.
Birrane et al., "Novel mode of ligand recognition the Erbin PDZ domain," *J Biol Chem.*, 278:1399-1402, 2003.
Blagoev et al., "A proteomics strategy to elucidate functional protien-protein interactions applied to EGF signaling," *Nat. Biotechnol.*, 21:315-318, 2003.
Boder et al., "Directed evolution of antibody fragments with monovalent femtomolar antigen-binding affinity," *Proc Natl Acad Sci.*, 97:10701-5.

Boder et al., "Yeast surface display for directed evolution of protein expression, affinity, and stability," *Methods Enzymol*, 328:430-44, 2000.
Boder et al., "Yeast surface display for screening combinatorial polypeptide libraries," *Nat Biotechnol*, 15:553-7, 1997.
Bogan, "Anatomy of hot spots in protein interfaces," *J Mol Biol*, 280:1-9, 1998.
Bork et al., "Proposed acquisition of an animal protein domain by bacteria," *Proc. Natl. Acad. Sci. USA*, 89:8990-8994, 1992.
Carr et al., "Backbone dynamics of homologous fibronectin type III cell adhesion domains from fibronectin and tenascin," *Structure*, 5:949-959, 1997.
Chou et al., "A simple apparatus for generating stretched polyacrylamide gels, yielding uniform alignment of proteins and detergent micelles," *J Biomol NMR*, 21:377-82, 2001.
Chou et al., "Study of conformational rearrangement and refinement of structural homology models by the use of heteronuclear dipolar couplings," *J Biomol NMR*, 18:217-27.
Decanniere et al., A single domain anti-body in a complex with RNase A: non-canonical loop structures nanomolar affinity using two CDR loops. *Structure Fold Des*, 7:361-70.
Dickinson et al., "Crystal structure of the tenth type III cell adhesion module of human fibronectin," *J Mol Biol*, 236:1079-1092, 1994.
Dieckman et al., "High throughput methods for gene cloning and expression," *Protein Expr Purif*, 25:1-7, 2002.
Dong et al, "Molecular forceps from cominatorial libraries prevent prevent the farnesylation of Ras by binding to its carboxyl terminus," *Chemistry and Biology*, 6:133-141, 1999.
Fan et al., "Biosensors based on binding-modulated donor-acceptor distances," *Trends Biotechnol.*, 23:186-92, 2005.
Fellouse et al., "Molecular recognition by a binary code," *J Mol Biol*, 348:1153-1162. 2005.
Fellouse et al., "Synthetic antibodies from a four-amino-acid code: a dominant role for tyrosine in antigen recognition," *Proc. Natl Acad Sci U S A*, 101:12467-72, 2004.
Ferrer et al., "Directed evolution of PDZ variants to generate high-affinity detection reagents," *Protein Eng Des Sel*, 18:165-173, 2005.
Fuh et al., "Analysis of PDZ domain-ligand interactions using carboxyl-terminal phage display," *J. Biol. Chem.*, 275:21486-91, 2000.
Hogrefe et al., "A bacteriophage lambda vector for the cloning and expression of immunoglobulin Fab fragments on the surface of filamentous phage," *Gene*, 128:119-26, 1993.
Hosse et al., "A new generation of protein display scaffolds for molecular recognition," *Protein Sci*, 15:14-27, (2006).
Huang et al., "Confirmation specific affinity purifications using engineered binding proteins: Application to the estrogen receptor," *Protein Expr Purif*, 2005.
Huang et al., "Design of protein function leaps by directed domain interface evolution," *Proc Natl Acad Sci USA*, 105:6578-83, 2008.
Huang et al., "IH, 13C, 15N NMR backbone assignments of 37kDa surface antigen OspC from Borrelia burgdorferi," *J Biomol NMR*, 14:283-284, 1999.
Ishii et al., "Controlling residual dipolar couplings in high-resolution NMR of protiens by strain induced alignment in a gel," *J Biomol NMR*, 21:141-151, 2001.
Iwakura et al., "Effects of the length of a glycine linker connecting the N- and C-termini of a circularly permuted dihydrofolate reductase," *Protein Eng*, 11:707-13, 1998.
Jones et al., "A quantative protein interaction network for the ERbB receptors using protein microarrays," *Nature*, 439:168-174, 2006.
Karatan et al., "Molecular recognition properties of FN3 monobodies that bind the Src SH3 domain," *Chem. Biol.*, 11:835-844, 2004.
Kessels et al. "Specificity and affinity motifs of Grb2-SH2-lignad interactions," *Proc Natl Acad Sci U S A*, 99:8524-9, 2002.
Kohda et al., "Solution structure and ligand-binding site of the carboxy-terminal SH3 domain of GRB2," *Structure*, 2:1029-40, 1994.

(56) References Cited

OTHER PUBLICATIONS

Kohno et al., "A new general method for the biosynthesis of stabel isotope-enriched peptides using a decahistidine-tagged ubiquitin fusion system: an application to the production of mastoparan-X uniformly enriched with 15N and 15N/13C," *J Biomol NMR*, 12:109-121, 1998.
Koide et al., "Design of single-layer beta-sheets without a hydrophobic core," *Nature*, 403:456-460, 2000.
Koide et al., "High affinity single-domain binding proteins with a binary-code interface," *Proc. Natl. Acad. Sci*, 104:6632-6637, 2007.
Koide et al., "Monobodies:antibody mimics based on the scaffold of fibronectin type III domain," *Methods Mol Biol* 35:95-109, 2007.
Koide et al., "Stabilization of a fibronectin type III domain by the removal of unfavorable electrostatic interactions on the protein surface," *Biochemistry*, 40:20326-33, 2001.
Koide et al., The fibronectin type III domain as a scaffold for novel binding proteins, *J Mol Biol.*, 284:1141-1151, 1998.
Kojima et al., "Importance of terminal residues on circularly permutated *Escherichia coli* alkaline phosphatase with high specific activity," *J Biosci Bioeng*, 100:197-202, 2005.
Kunkel et al., "Rapid and efficient site-directed mutagenesis without phenotypic selection," *Methods Enzymol*, 154:367-382, 1987.
Laura et al., "The Erbin PDZ domain binds with high affinity and specificity to the carboxyl termini of delta-catenin and ARVCF," *J Biol Chem*, 277:12906-12914, 2002.
Lo Conte et al., "The atomic structure of protein-protein recognition sites," *J. Mol Biol*, 285:2177-2199, 1999.
Looger et al., "Computational design of receptor and sensor proteins with novel functions," *Nature*, 423:185-90, 2003.
Lu et al., "Function of WW domains as phosphoserine- or phosphothreonine-binding modules," *Science* 283:1325-8, 1999.
Main et al., The three-dimensional structure of the tenth type III cell adhesion module of fibronectin: an insight into RGD-mediated interactions, *Cell*, 71:671-678,1992.
Martinez et al., "Thermodynamic analysis of alpha-spectrin SH3 and two of its circular permutants with different loop lengths: discerning the reasons for rapid folding in proteins," *Biochemistry* 38:549-59, 1999.
Miyawaki et al., "Dynamic and quantitative Ca2+ measurements using improved cameleons," *Proc Natl Acad Sci U S A*, 96:2135-40, 1999.
Miyawaki et al., "Fluorescent indicators for Ca2+ based on green fluorescent proteins and calmodulin," *Nature*, 388:882-7.
Murphy et al., "Substrates for cell adhesion prepared via active site-directed immobilization of a protein domain," *Langmuir*, 20:1026-1030, 2004.
Nguyen et al., "Evolutionary optimization of fluorescent proteins for antracellular FRET," *Nat Biotechnol*, 23:355-60, 2005.
Nioche et al., "Crystal Structures of the SH2 domain of Grb2: highlight on the binding of a new high-affinity inhibitor," *J Mol Biol*, 315:1167-77, 2002.
Nourry et al., "PDZ domain proteins: plug and play!," *Sci STKE*,RE7, 2003.
Ohnishi et al., "Solution Confirmation and Amyloid-like Fibril Formation of a Polar Peptide Derived from a β-Sheet," *J Mol Biol*, 301:477-489, 2000.
Olson et al., "Design, expression and stability of a diverse protein library based on human fibronectin type III domain," *Protein Science*, 16:476-484, 2007.
Ostermeier et al., "Engineering allosteric protein switches by domain insertion," *Protein Eng Des Sel*, 18:359-64, 2005.
Osuna et al., "Improving a circularly permuted TEM-1 beta-lactamase by directed evolution," *Protein Eng*, 15:463-70, 2002.
Ottiger et al., "Measurement of J and dipolar couplings from simplified two dimensional NMR spectra," *J Magn Reson*, 131:373-8, 1998.
Panni et al., "In vitro evolution of recognition specificity mediated by SH3 domains reveals target recognition rules," *J. Biol. Chem*, 277:21666-74.

Pawson et al., "Assembly of a cell reulatory systems through protein interaction interaction domains," *Science*, 300:445-52, 2003.
Pham et al., "NMR studies of *Borrelia burgdorferi* OspA, a 28kDa protein containing a single-layer β-sheet," *J Biomol NMR*, 11:407-414, 1998.
Plaxco et al., "A comparison of the folding kinetics and thermodynamics of two homologous fibronectin type III modules," *J Mol Biol.*, 270:763-770, 1997.
Plaxco et al., "Rapid refolding of proline-rich all-beta-sheet fibronectin type III module," *Proc. Natl. Acad. Sci. USA*, 93:10703-10706, 1996.
Prestegard., "New techniques in structural NMR—anisotropic interactions," *Nature Struct Biol*, 5:517-522, 1998.
Rahuel et al., "Structural basis for specificty of Grb2-SH2 revealed by a novel ligand binding mode," *Nat Struct Biol* 3:589-9, 1996.
Reina et al., "Computer-aided design of a PDZ domain to recognize new target sequences," *Nat. Struct Biol.*, 9:621-7, 2002.
Rippmann et al., "Phosphorylation-dependent proline isomerization catalyzed by Pin1 is essential for tumor cell survival and entry into mitosis," *Cell Growth Differ* 11:409-16, 2000.
Schlessinger et al., "SH2 and PTB domains in tyrosine kinase signaling," *Sci STKE*, RE12, 1999.
Shaner et al., "A guide to choosing fluorescent proteins," *Nat Methods*, 2:905-9, 2005.
Shierle et al., "The DsbA signal sequence directs efficient, cotranslational export of passenger proteins to the *Escherichia coli* periplasma via the signal recognition particle pathway," *J Biotechnol*, 185:5706-13, 2003.
Sidhu et al., "Phage display for selection of novel binding peptides," *Methods Enymol*, 328:333-363, 2000.
Skelton et al., "Origins of PDZ domain binds with high affinity and specificity structure. Structure determination and mutagenesis of PDZ domain," *J Biol Chem.*, 278:7645-7654, 2003.
Skerraa, "Engineered protein scaffolds for molecular recognition," *J. Mol. Recognit.*, 13(4):167-87, 2000.
Songyang et al., "A single point mutation switches the specificity of group III Src homology," *J Biol Chem* 270:26023-32, 1995.
Songyang et al., "Recognition and specificty in protein tyrosine kinase-mediated signalling," *Trends Biochem Sci*, 20:470-5, 1995.
Songyang et al., "SH2 Domains Recognize Specific Phosphopeptide Sequencess," *Cell*, 72:767-78, 1993.
Steiner et al., "Signal sequences directing cotransitonal translocation expand the range of proteins amenable to phage display," *Nat Biotechnol.*, 24:823-31, 2006.
Steitz et al., "Structural dynamics of yeast hexokinase during catalysis," *Philos. Trans. R. Soc. Lond. B. Biol Sci.*, 293:43-52,1981.
Stern et al., "Tyrosine kinase signaling in breast cancer: ErbB family receptor tyrosine kinases," *Breast Cancer Res*, 2:176-83, 2000.
Tjandra et al., "Defining long range order in NMR structure determination from the dependence of heteronuclear relaxation times on rotational diffusion," *Nature Struct Biol*, 4:443-449, 1997.
Tsien et al., "Seeing the machinery of live cells," *Science*, 280:1654-5, 1998.
VanAntwerp et al., "Fine affinity discrimination by yeast surface display and flow cytometry," *Biotechnol Prog* 16:31-7, 2000.
Verdecia et al., "Structural basis for phosphoserine-proline recognition by group IV WW domains," *Nat Struct Biol* 7:639-43, 2000.
Weiss et al., "The development of molecular clams as drugs," *Drug Discovery Today*, 11:819-824, 2006.
Wiedmann et al, "Quantification of PDZ domain specificty, prediction of ligand affinity and rational designe of super-binding peptides," *J. Mol. Biol.*, 343:703-18, 2004.
Xu et al., "Directed evolution of high-affinity antibody mimics using mRNAdisplay," *Chem Biol*, 9:933-942, 2000.
Yaffe et al., "A motif-base profile scanning approach for genome-wide prediction of signaling pathways," *Nat. Biotechnol*, 19:348-353, 1998.
Yaffe et al., "PhosphoSerine/threonine binding domains: you can pSERious?" *Structure* 9:R33-8, 2001.
Yan et al., "Themodynamic and Kinetic Exploration of the Energy Landscape of Borrelia burgdorferi OspA by Native-state Hydrogen Exchange," *J Mol Biol*, 323:363-75, 2002.

(56) References Cited

OTHER PUBLICATIONS

Yang et al., "TROSY-based HNCO pulse sequences for the measurement of 1HN-15N, 15N-13CO, IHN-13CO, 13CO-13Ca and 1HN-13Ca dipolar couplings in 15N, 13C, 2H-labeled proteins," *J Biomol NMR*, 14:333-343, 1999.

Zucconi et al., "Domain repertoires as a tool to derive protein recognition rules," *FEBS Lett*, 480:49-54, 2000.

\* cited by examiner

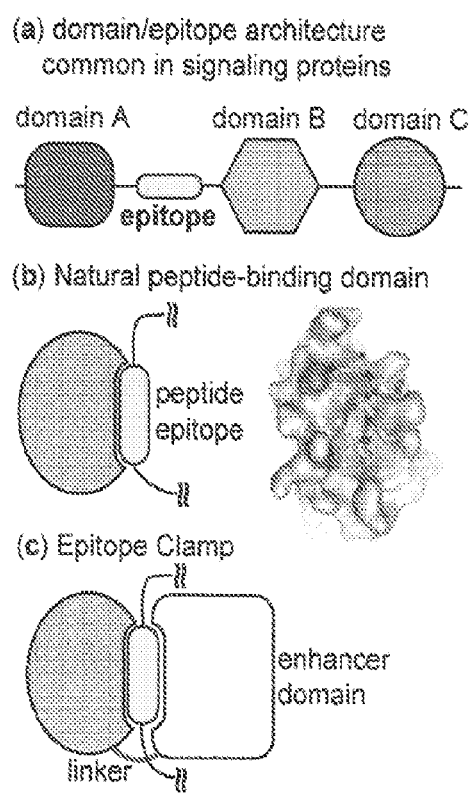
FIG. A1

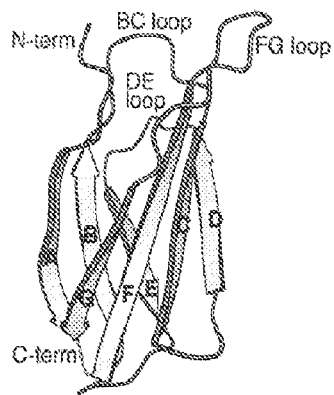
FIG. B1
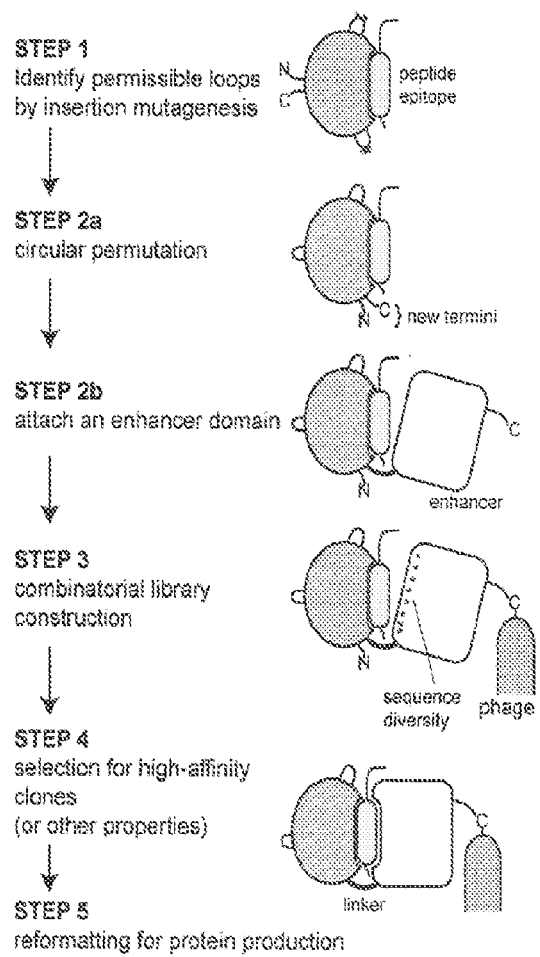
FIG. B2

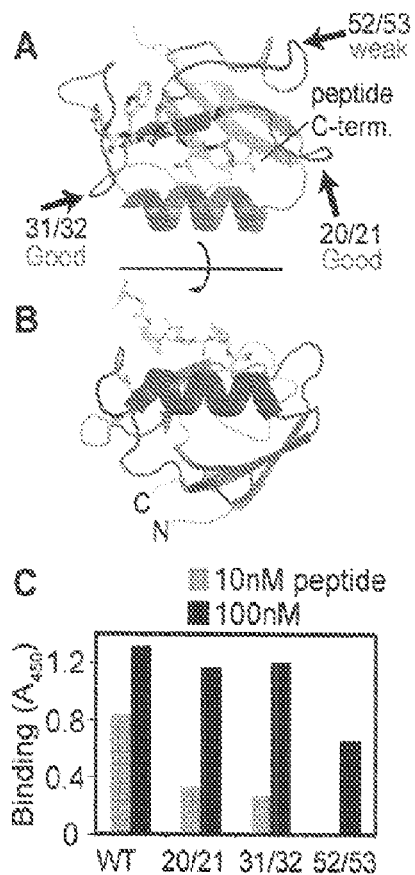
FIG. C1
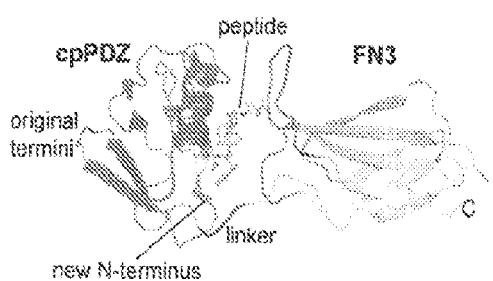
FIG. C2

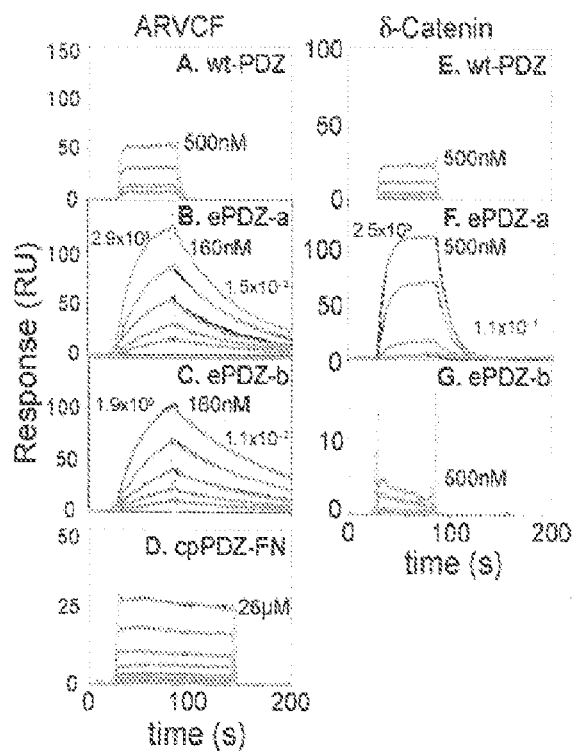
FIG. C3
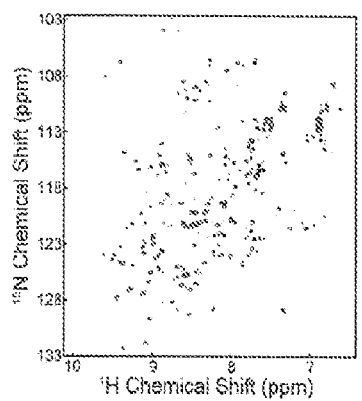
FIG. C4

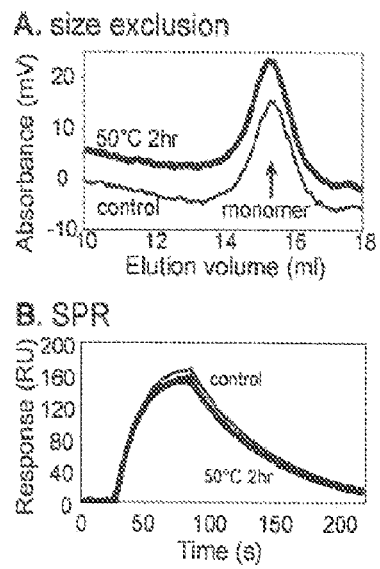
FIG. C5
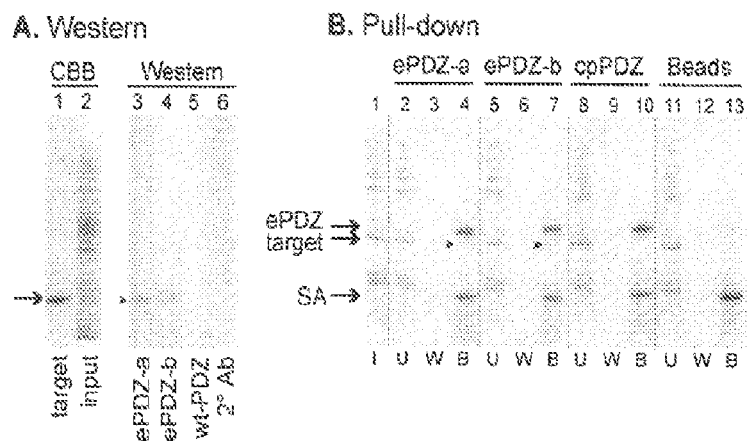
FIG. C6
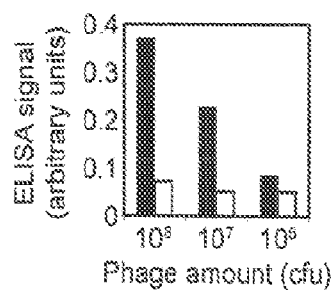
FIG. C7

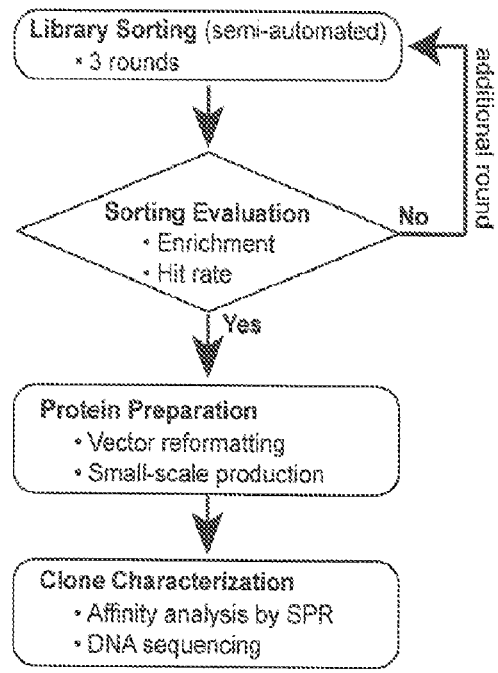
FIG. D1
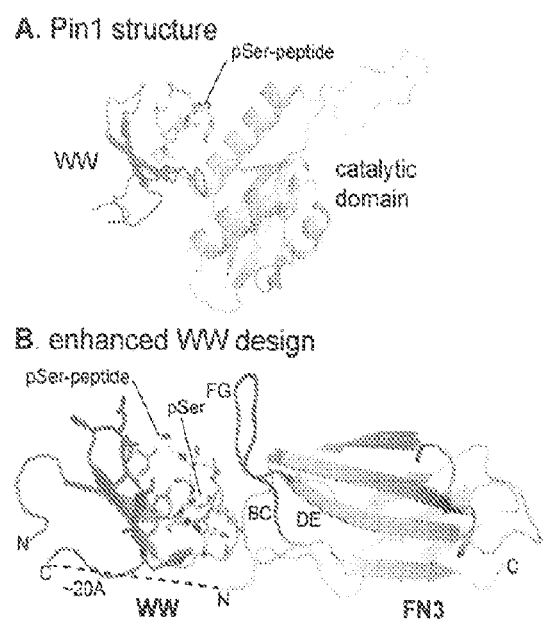
FIG. D2

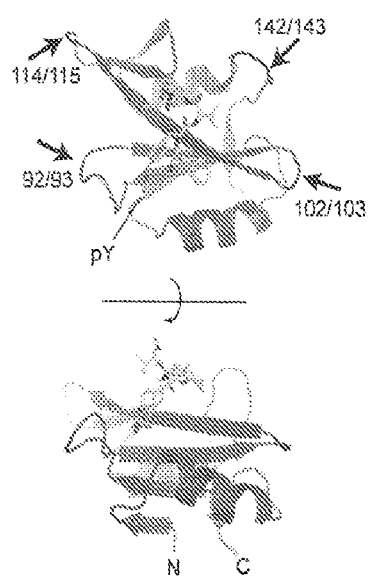
FIG. D3

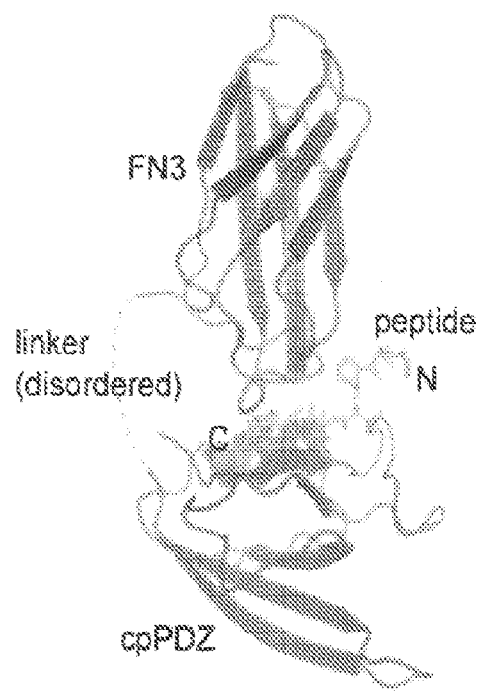
FIG. E1
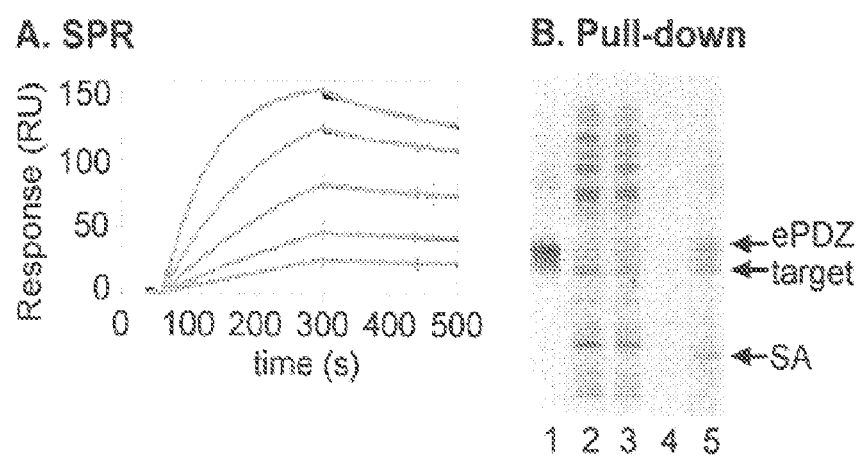
FIG. E2

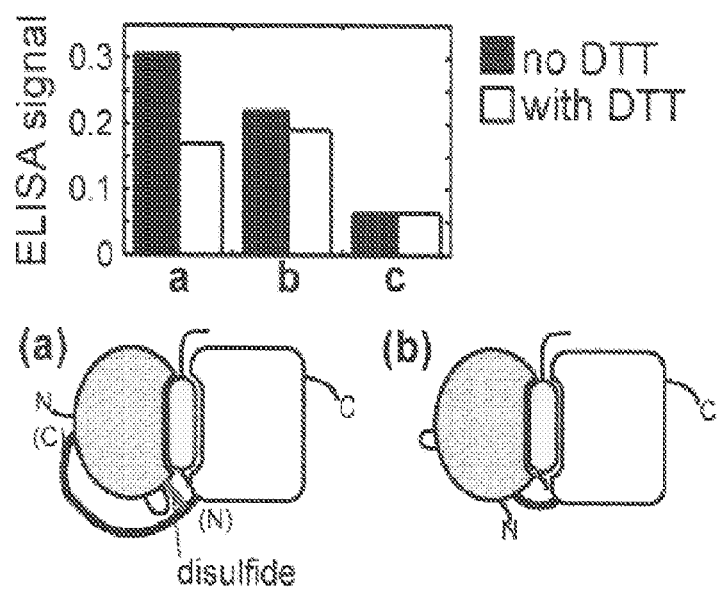
FIG. E3

Library 1: XXXX(STAVIF)X(ILVATP)(SEQ ID NO: 64)-COOH
ePDZ-b           # of occurrence
GEIDTWV (SEQ ID No: 1)    2
GPMDTWV (SEQ ID No: 2)    3
GPLDTWV (SEQ ID No: 3)    1
GPIDTWV (SEQ ID No: 4)    3
ePDZ-b1
SPIDTWV (SEQ ID No: 5)    3
GPIDTWV (SEQ ID No: 6)    11
GSIDTWV (SEQ ID No: 7)    4
GPLDTWV (SEQ ID No: 8)    2
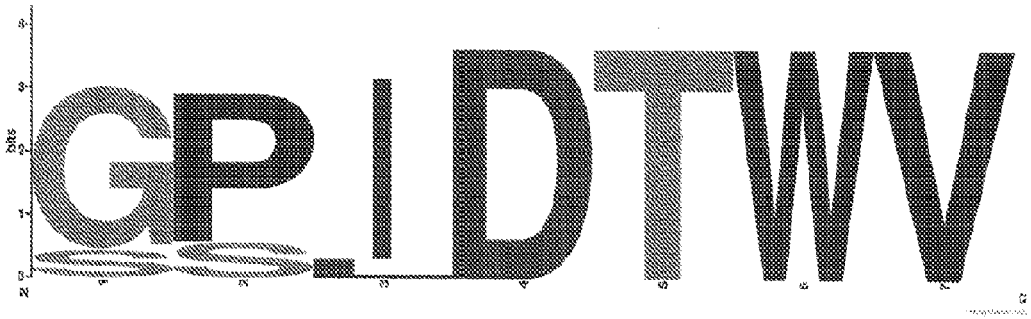
ePDZ-b2
SNIDTWV (SEQ ID No: 9)    6
SQIDTWV (SEQ ID No: 10)   2
SNLDTWV (SEQ ID No: 11)   3
RNIDTWV (SEQ ID No: 12)   1
GSIDTWV (SEQ ID No: 13)   3
TSIDTWV (SEQ ID No: 14)   1
GPMDTWV (SEQ ID No: 15)   1
FIG. E4

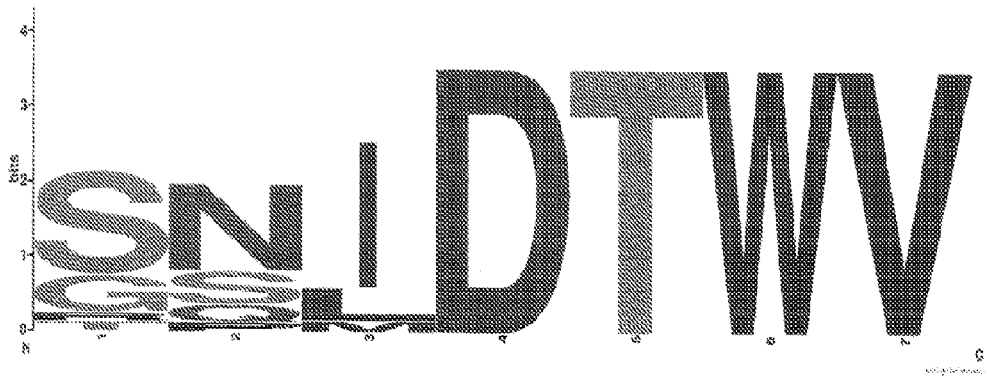

Library 2: XXXXXDSWV (SEQ ID No: 65)-COOH ePDZ-b                          # of occurrence
KRGSIDSWV   (SEQ ID No: 16)     4
ERGAIDSWV   (SEQ ID No: 17)     1
KRGSIDSWV   (SEQ ID No: 18)     1
PRGSIDSWV   (SEQ ID No: 19)     1
KRGAIDSWV   (SEQ ID No: 20)     3
KRMPIDSWV   (SEQ ID No: 21)     1
KRGPIDSWV   (SEQ ID No: 22)     1
PRMPIDSWV   (SEQ ID No: 23)     1
DRMPFDSWV   (SEQ ID No: 24)     1
KRMPLDSWV   (SEQ ID No: 25)     1
PRGELDSWV   (SEQ ID No: 26)     1

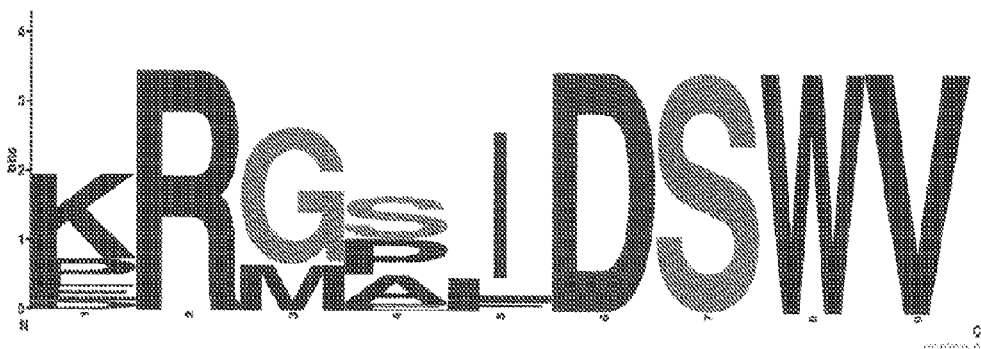

ePDZ-b1
NRGRMDSWV   (SEQ ID No: 27)     1
DRGSMDSWV   (SEQ ID No: 28)     1
KRGSMDSWV   (SEQ ID No: 29)     1
KRGSIDSWV   (SEQ ID No: 30)     3
KRSNIDSWV   (SEQ ID No: 31)     2

FIG. E4 (cont'd)

KRFEIDSWV (SEQ ID No: 32)    1
KRFNIDSWV (SEQ ID No: 33)    1
ERFSIDSWV (SEQ ID No: 34)    1
KRGQIDSWV (SEQ ID No: 35)    1
FRGEIDSWV (SEQ ID No: 36)    1
VRGEIDSWV (SEQ ID No: 37)    1
SRGAIDSWV (SEQ ID No: 38)    1
VRGSIDSWV (SEQ ID No: 39)    1
ARGSIDSWV (SEQ ID No: 40)    2
RRGSIDSWV (SEQ ID No: 41)    1
ePDZ-b2
QRGNIDSWV (SEQ ID No: 42)    1
TRGNIDSWV (SEQ ID No: 43)    1
RRGNIDSWV (SEQ ID No: 44)    1
QRWNIDSWV (SEQ ID No: 45)    1
KRGTIDSWV (SEQ ID No: 46)    2
RSGSIDSWV (SEQ ID No: 47)    1
ERSSIDSWV (SEQ ID No: 48)    1
FIG. E4 (cont'd)

ERQSIDSWV (SEQ ID No: 49) 1
KRSNMDSWV (SEQ ID No: 50) 1
GRGNMDSWV (SEQ ID No: 51) 1
NRGQMDSWV (SEQ ID No: 52) 1
GRGSMDSWV (SEQ ID No: 53) 1
ERGSMDSWV (SEQ ID No: 54) 1
GRGSLDSWV (SEQ ID No: 55) 2
RRGSLDSWV (SEQ ID No: 56) 1
KRNSLDSWV (SEQ ID No: 57) 1
KRSSLDSWV (SEQ ID No: 58) 1
FIG. E4 (cont'd)

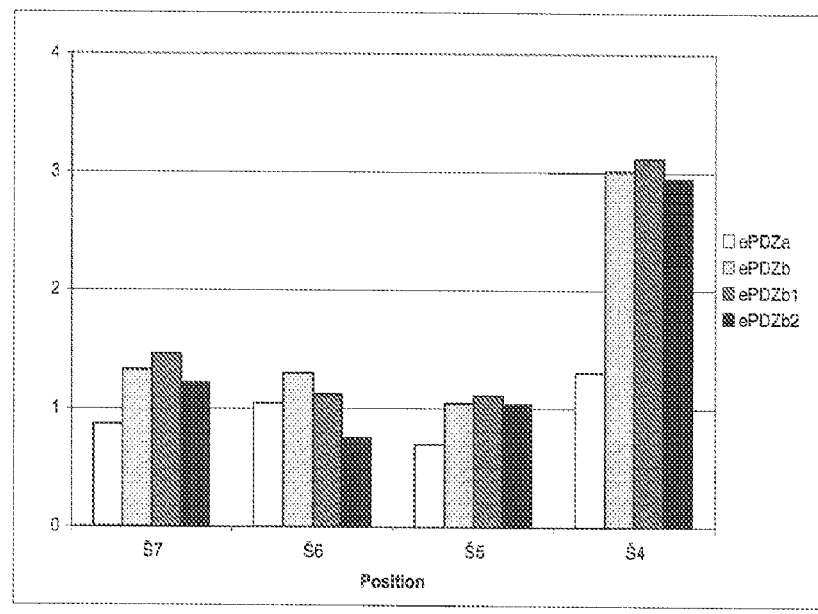
FIG. E5

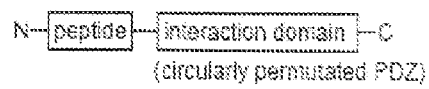
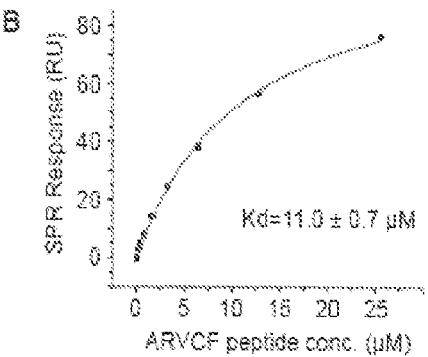
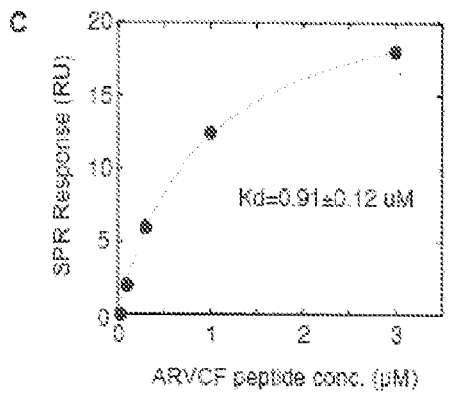
FIG. F1

282-1-H8 w/ signal peptide

```
          10         20         30         40         50         60
MKKIWLALAG LVLAFSASAA GSSNCRHNTG YNSCSRPELG FSISGGVGGR GNPFRPDDDG 70         80         90        100        110        120
IFVTRVQPEG PASKLLQPGD KIIQANGYSF INIEHGQAVS LLKTFQNTVE LIIVREVGNG 130        140
AKQEIRVRVE KDGGHHHHHH HH   (SEQ ID NO: 62)
```

282-6-H8 w/ signal peptide

```
          10         20         30         40         50         60
MKKIWLALAG LVLAFSASAA GSNFCASNGT GNDCRRPELG FSISGGVGGR GNPFRPDDDG 70         80         90        100        110        120
IFVTRVQPEG PASKLLQPGD KIIQANGYSF INIEHGQAVS LLKTFQNTVE LIIVREVGNG 130        140
AKQEIRVRVE KDGGHHHHHH HH   (SEQ ID NO: 63)
```

FIG. G1

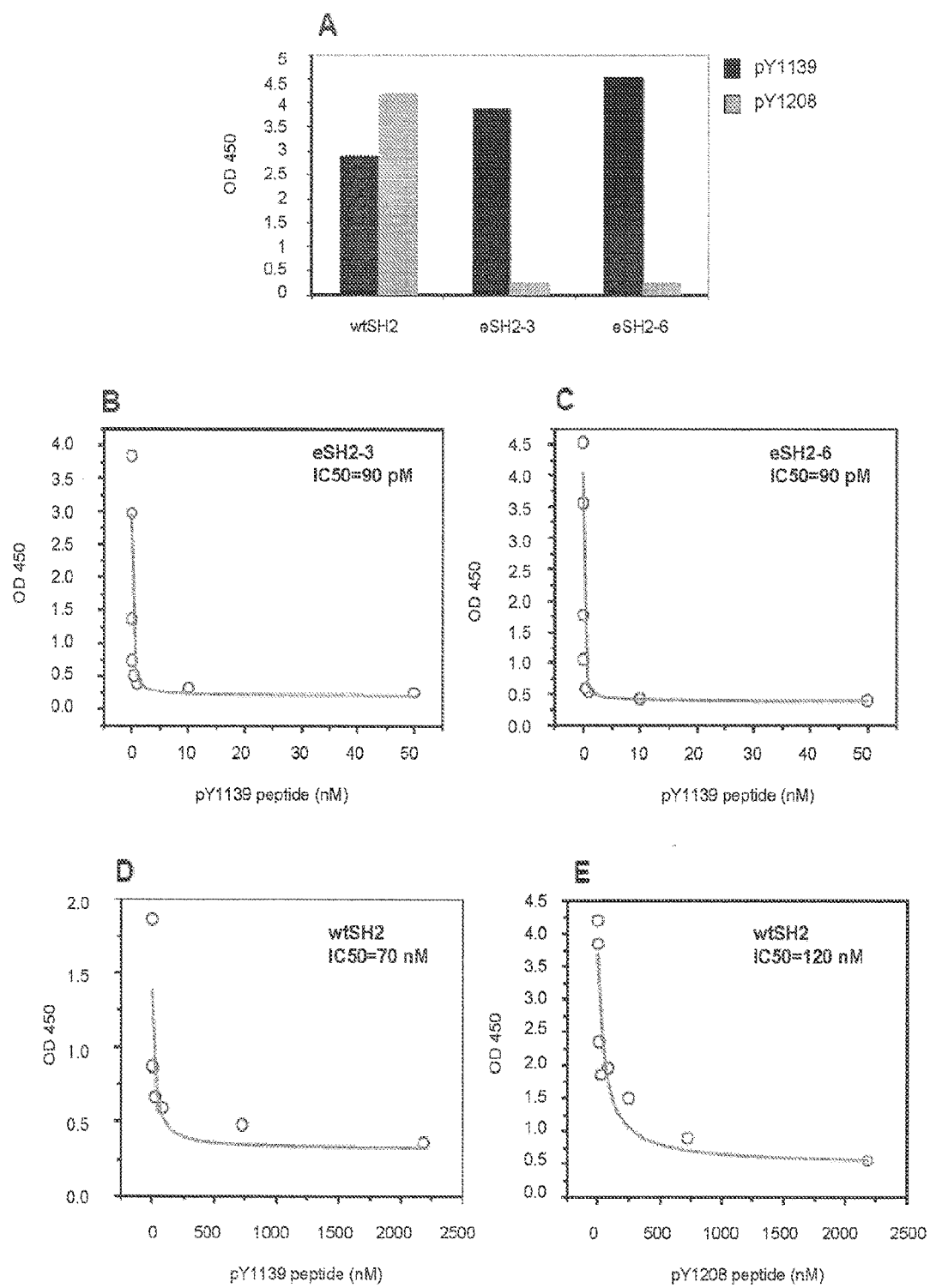
FIG. H1

MOLECULAR AFFINITY CLAMP TECHNOLOGY AND USES THEREOF

CROSS-REFERENCE TO RELATED APPLICATIONS

The present application is a national phase application under 35 U.S.C. § 371 of International Patent Application PCT Application No. PCT/US2008/083021, filed Nov. 10, 2008, which claims the benefit of U.S. Provisional Application No. 60/986,475 filed Nov. 8, 2007 and U.S. Provisional Application No. 61/016,736, filed Dec. 26, 2007. The entire contents of which these applications are incorporated by reference.

STATEMENT REGARDING FEDERALLY SPONSORED RESEARCH OR DEVELOPMENT

This invention was made with government support under DK063090 awarded by the National Institutes of Health. The government has certain rights in the invention.

INTRODUCTION

A major bottleneck in virtually all areas of biomedical sciences and disease diagnoses is a paucity of high-quality affinity reagents. Affinity reagents are indispensable for delineating the molecular mechanisms of diseases, for detecting and characterizing cellular abnormalities, and for characterizing effects of drugs. In this post-genome era, the demand for high-quality affinity reagents is rapidly increasing across all fields of biomedical sciences.

Short peptide motifs are, in principle, attractive targets against which affinity reagents can be generated. Short peptides derived from a target protein can be chemically synthesized, and the epitope (the region within a target that is recognized by an affinity reagent) can be readily deduced. Such short peptide motifs are important, for example, in signaling transduction networks. Many signal transduction processes are mediated by covalent modification within short peptide motifs of proteins that subsequently recruit other proteins or induce protein conformational changes. Short peptide motifs (and their modification state) are thus indicators (or biomarkers) of the functional state of extremely important components of these networks. For example, the phosphorylation/dephosphorylation cycle, comprising specific kinases and phosphatases, has long been recognized as a critical part of many signaling networks. A phosphorylated motif is often a signature of the activated state for transcription factors and receptor kinases. Affinity reagents to such defined peptide motifs within a target protein would provide "the ultimate validation because identical patterns in various assays give strong support for specificity and lack of cross-reactivity." (2).

Currently, antibodies are the gold standard of affinity reagents. However, making antibodies that recognize a particular short peptide motif with high affinity and specificity is difficult and time-consuming. The paucity of good antibodies to short peptides is not due to a lack of intensive effort. The difficulty arises from the fundamental thermodynamics of the binding of a short flexible peptide motif in which a small number of antibody-motif contacts must compensate for a large loss of conformational entropy. This is, perhaps, not so surprising because antibodies have not evolved specifically to bind short peptide motifs.

Antibodies have additional serious limitations. Monoclonal antibody production is low throughput and expensive, and polyclonal antibodies have a fundamental problem in production scalability and archiving. Although many monoclonal antibodies to whole protein antigens exist, very few are available for defined short peptide motifs and even fewer for post-translationally modified peptide segments that play critical roles in, for example, signaling and cancer biology. As to the latter, a recent inspection of a commercial catalog revealed that only 4 of the 280 available antibodies to phosphorylated peptide motifs are monoclonal antibodies.

As to polyclonal antibodies, which are widely used, the upfront costs and efforts to generate such antibodies are low. Polyclonal antibodies do not, however, meet the criteria for high-performance affinity reagents. A polyclonal antibody is impossible to reproduce with the identical properties once the stock is depleted, making it unfeasible to establish a robust standard assay that can be broadly distributed. Further, the inherently heterogeneous nature of a polyclonal antibody makes it impossible to define precisely its properties such as motif specificity and affinity. Polyclonal antibodies also cannot be easily reformatted for different applications.

In the last decade, nucleic acid-based affinity reagents have been developed (3, 4). However, they share the same difficulty as antibodies in generating high-affinity binders to short peptide motifs. To date, no nucleic acid aptamers have been generated that have low nM $K_d$ to a short peptide motif derived from a natural protein.

Each of the current approaches for designing affinity reagents has numerous disadvantages and fails to generate high-performance affinity reagents to small peptide motifs that are critically important.

BRIEF DESCRIPTION OF INVENTION

The inventors have developed a new platform technology for affinity reagents. The affinity reagents embodying the principles of the invention possess affinity and specificity for short peptide target motifs of interest. These affinity reagents are termed "modular molecular affinity clamps" because they have a clamp-like or clamshell architecture and are composed of two discrete modules. One module or shell is a "specificity" shell engineered from a natural binding domain, e.g., protein-interaction domain, which possesses inherent class specificity. The other shell or module is an "enhancer" shell which is an engineered single-domain antibody mimic. The shells or modules are connected to each other through a natural tail of one of the modules, or indirectly via a linker moiety. The shells or modules each bind the same target peptide motif, wherein, simultaneously and synergistically, the specificity of the "specificity shell" can be enhanced by >2,000 fold and the affinity can be increased >2,000 fold.

The molecular affinity clamps in accordance with the invention meet a number of requirements for affinity agents, including high affinity, high specificity, high-throughput (HTP) generation, and scalable and economical production. They have low nM dissociation constant(s) ($K_d$) for the target motifs and function well in immunochemical applications. Further, by exploiting binding-induced conformational changes, the molecular affinity clamps can be used as label-free biosensors for diverse molecular motifs including those containing posttranslational modifications.

BRIEF DESCRIPTION OF THE DRAWINGS

Exemplary embodiments of the invention will hereinafter be described in conjunction with the appended drawing wherein like designations refer to like elements throughout and in which:

FIG. A1 is a schematic representation of the assembly of a modular molecular affinity clamp embodying the principles of the invention;

FIG. B1 is a ribbon drawing of FN3;

FIG. B2 illustrates the modular molecular affinity clamp engineering strategy embodying the principles of the invention;

FIG. C1 (A) is a schematic representation of the erbin PDZ domain (1N7T), (B) is a 90° rotational view, and (C) shows binding effects of loop insertions;

FIG. C2 is a schematic representation of enhanced PDZ (cpPDZ);

FIG. C3 is a SPR (BIAcore) analysis of motif binding of ePDZ's and the parent proteins;

FIG. C4 is a $^1$H, $^{15}$N-HSQC spectra of free $^{15}$N-labeled ePDZ-a (black) and peptide-bound ePDZ-a (gray);

FIG. C5 are graphs demonstrating the heat stability of ePDZs;

FIG. C6 demonstrates applications of ePDZ's in Western blotting and pull-down assays;

FIG. C7 is an analysis of a phage display of the Grb2-SH2 domain;

FIG. D1 is a flowchart of HTP library screening procedures in accordance with the invention;

FIG. D2 (A) is a schematic representation of the Pin1 crystal structure (PDB ID, 1F8A), and (B) is a representation of the designed interactions between the WW and FN3 domains in an eWW protein;

FIG. D3 is a schematic representation of Grb2-SH2 domain bound to a pY-containing peptide (PDB ID: 1TZE);

FIG. E1 illustrates the x-ray crystal structure of ePDZ-a;

FIG. E2 (A) is a graph of the binding kinetics of the affinity-matured ePDZ to the ARVCF target peptide, and (B) illustrates the immunoprecipitation of the target peptide;

FIG. E3 is a graph and schematic representation of the binding of (a) affinity clamps without circular permutation, (b) ePDZ-a (positive control), and (c) PDZ only (negative control) to the ARVCF target peptide as measured by phage ELISA;

FIG. E4 shows libraries of the sequences of isolated clones (SEQ ID NOs: 1-58) from C-terminal peptide libraries (SEQ ID NOs: 64-65);

FIG. E5 is a graph of the effects of Ala substitution of the ARVCF peptide on the binding affinity of PDZ clamps;

FIG. F1 (A) is a schematic of the peptide-cpPDZ, with peptide library (SEQ ID NOs: 59-61); (B) is a graph illustrating the binding kinetics of the circularly permutated PDZ domain, and (C) is a graph illustrating the binding kinetics of the peptide-cpPDZ (clone 282-6);

FIG. G1 shows the sequences of the peptide-PDZ affinity clamps with secretion signal sequences, sequences selected from combinatorial library, and His8 tags (SEQ ID NOs: 62-63); and FIG. H1 is a series of graphs (A-E) comparing of binding affinity and specificity of the Grb2-SH2 domain and SH2 clamps.

BRIEF DESCRIPTION OF THE TABLES

Table 1: FN3 loop sequences of ePDZ's selected for ARVCF.
Table 2: $K_d$ of ePDZ's and the parent proteins.
Table 3: Phospho-peptide motifs.
Table 4: A summary of library sorting and binding parameters of affinity clamps in accordance with the invention.
Table 5: Amino acid sequences of linker and three FN3 loops of the eSH2's selected for pY1139 shown in FIG. H1.

DETAILED DESCRIPTION

In accordance with the invention, modular molecular affinity clamps are provided that have both high affinity and specificity for given targets of interest.

The invention will now be further described through the following detailed description, which description is illustrative of certain embodiments of the invention and is not intended to limit the scope of the invention as set forth in the appended claims. While the following detailed description reveals the invention through reference to embodiments utilizing certain interaction domains and engineered antibody mimics, it should be understood that other natural binding domains and engineered polypeptides are also suitable for use with the principles of the invention.

Further, no admission is made that any reference, including any patent or patent document, cited in this specification constitutes prior art. In particular, it will be understood that, unless otherwise stated, reference to any document herein does not constitute an admission that any document forms part of the common general knowledge in the art in the United States or in any other country. Any discussion of the references states what their authors assert, and applicants reserve the right to challenge the accuracy and pertinency of any of the documents cited herein.

Throughout this disclosure, various aspects of this invention may be presented in a range format. It should be understood that the description in range format is merely for convenience and brevity, and should not be construed as an inflexible limitation on the scope of the invention. Accordingly, as will be understood by one skilled in the art, for any and all purposes, particularly in terms of providing a written description, all ranges disclosed herein also encompass any and all possible subranges and combinations of subranges thereof, as well as integral and fractional numerical values within that range. As only one example, a range of 20% to 40% can be broken down into ranges of 20% to 32.5% and 32.5% to 40%, 20% to 27.5% and 27.5% to 40%, etc. Further, any listed range can be easily recognized as sufficiently describing and enabling the same range being broken down into at least equal halves, thirds, quarters, fifths, tenths, etc. As a non-limiting example, each range discussed herein can be readily broken down into a lower third, middle third, and upper third, etc. Also, as will also be understood by one skilled in the art, all languages such as "up to," "at least," "greater than," "less than," "more than," and the like include the number recited and refer to ranges which can be subsequently broken down into subranges as discussed above. In the same manner, all ratios disclosed herein also include all subratios falling within the broader ratio. These are only examples of what is specifically intended. Moreover, the phrases "ranging/ranges between" a first indicate number and a second indicate number and "ranging/ranges from" a first indicate number "to" a second indicate number are used herein interchangeably.

It is also understood that the use of "comprising," "including," "having," and variations thereof herein is meant to encompass the items listed thereafter and equivalents thereof as well as additional items, e.g., other steps, ingredients or elements that do not affect the final result can be added. The term "comprising" encompasses the terms "consisting of" and "consisting essentially of". The use of "consisting essentially of" means that the composition or method may include additional ingredients and/or steps, but only if the additional ingredients and/or steps do no materially alter the basic and novel characteristics of the claimed composition or method.

Unless otherwise defined, all scientific and technical terms are used herein according to conventional usage, and have the same meaning as commonly understood by one of ordinary skill in the art to which the invention belongs. However, as used herein, the following definitions may be useful in aiding the skilled practitioner in understanding the invention:

"Modular molecular affinity clamp," "molecular affinity clamp" and "affinity clamp" (used interchangeably) are meant to refer to an affinity complex embodying the principles of the invention that has a bimodular architecture of two biorecognition modules which are linked together and bind the same target motif of interest.

"Biorecognition module" and "recognition module" (used interchangeably), as used herein, refer to a biomolecule which makes up one module of the modular molecular affinity clamp embodying the principles of the invention. A biorecognition module contains a molecular recognition domain that has affinity for a target motif of interest.

"Molecular recognition domain" and "recognition domain", (used interchangeably), as used herein, refer to a binding domain within a biorecognition module that demonstrates an ability to bind to a target motif, i.e., has binding affinity for a target motif.

The terms "target" and "target molecule," as used herein, refer to any biomolecule of interest for which a molecular affinity clamp is sought. Exemplary targets include, but are not limited to, secreted peptide growth factors, pharmaceutical agents, cell signaling molecules, blood proteins, portions of cell surface receptor molecules, portions of nuclear receptors, steroid molecules, viral proteins, carbohydrates, enzymes, active sites of enzymes, binding sites of enzymes, portions of enzymes, small molecule drugs, cells, bacterial cells, proteins, epitopes of proteins, surfaces of proteins involved in protein-protein interactions, cell surface epitopes, diagnostic proteins, diagnostic markers, plant proteins, peptides involved in protein-protein interactions, and foods. The target may be associated with a biological state, such as a disease or disorder in a plant or animal as well as the presence of a pathogen. When a target is "associated with" a certain biological state, the presence or absence of the target or the presence of a certain amount of target can identity the biological state.

A "target motif", as used herein, refers to any portion or sequence of a biomolecule of interest for which a molecular affinity clamp is sought, e.g., refers to a pattern of amino acid residues which is recognized by particular recognition domains. In accordance with the invention, the target motif binds more than one recognition domain. In other words, a target motif is one to which an affinity clamp embodying the principles of the invention can bind with high affinity and specificity. Of particular importance are target motifs that are short peptides of about 2-100 amino acid residues, especially those of 3-10 amino acid residues.

As used herein, the term "binds" in connection with the interaction between a target motif and a recognition domain indicates that the recognition domain associates with (e.g., interacts with or complexes with) the target motif to a statistically significant degree as compared to association with proteins generally (i.e., non-specific binding). Thus, the term "molecular recognition domain" is also understood to refer to a domain that has a statistically significant association or binding with a target motif.

In the context of a recognition domain binding to a target motif, the term "greater affinity" indicates that an affinity clamp binds more tightly than a reference domain, or than the same domain in a reference condition, i.e., with a lower dissociation constant. In particular embodiments, the greater affinity is at least 2-fold.

Also in the context of recognition domain binding to a target motif, the term "altered specificity" indicates that relative binding affinity of an affinity clamp to two or more motifs is different from that exhibited by a biorecognition module alone. In other words, "altered binding specificity" may refer to an increased binding constant of the affinity clamp for one target motif without the same level of increase for another target, an unchanged binding constant for one target with a decreased binding constant for another, target or a combination thereof.

The term "linked" refers to any method of functionally connecting peptides, particularly the two modules of the modular affinity clamps embodying the principles of the invention. "Linked" may also refer to non-covalent physical association. The biomolecular modules making up the biorecognition modules of the affinity clamps may be linked directly covalently, e.g., via a peptide linkage, or non-covalently, or indirectly via a linker.

A "linker" or "linker moiety," (used interchangeably) may refer to a peptide sequence of about 30 or more amino acid residues that is configured to associate two biorecognition modules in an orientation that facilitates binding of each module to a target motif. The linker, generally, is bifunctional in that it includes a functionality for linking the first biorecognition module and a functionality for linking the second biorecognition module.

By "molecular scaffold" or "scaffold" is meant a core molecule or framework, particularly a polypeptide, used to design, engineer or select a polypeptide with specific and favorable properties, such as binding affinity. One or more additional chemical moieties can be covalently attached to, modified, or eliminated from the core molecule to form a plurality or library of molecules with common structural elements. Characteristics of a scaffold can include having chemical positions where moieties can be attached that do not interfere with binding of the scaffold to a protein binding site, such that the scaffold or library members can be modified to improve binding affinity and/or specificity. When designing or engineering polypeptides or proteins from a scaffold, amino acid residues that are important for the framework's favorable binding properties are retained, while others may be varied to provide a peptide with improved linkage to generate tailor-made motif-specific binding proteins that are used as modules in molecular affinity clamps in accordance with the invention.

By "binding site" is meant an area or region within a recognition domain where a biomolecule can bind non-covalently, i.e., interact with higher affinity than background interactions between molecules. Binding sites embody particular shapes and often can contain multiple binding pockets present within the binding site. The particular shapes are often conserved within a class of molecules, such as a protein family. Binding sites within a class also can contain conserved structures such as, for example, chemical moieties, the presence of a binding pocket, and/or an electrostatic charge at the binding site or some portion of the binding site, all of which can influence the shape of the binding site.

By "binding pocket" is meant a specific volume of space within a binding site that is available for occupation by a biomolecule. A binding pocket can often be a particular shape, indentation, groove, or cavity in the binding site. Binding pockets can contain particular chemical groups or structures that are important in the non-covalent binding of another molecule such as, for example, groups that contribute to ionic, hydrogen bonding, or van der Waals interactions between the molecules.

By "orientation" or "oriented," in reference to a biorecognition module bound to a target motif, is meant the spatial relationship of the biorecognition module, and at least some of its constituent atoms, to the atoms of the target motif.

By "assaying" is meant the creation of experimental conditions and the gathering of data regarding a particular result of the experimental conditions. For example, enzymes can be assayed based on their ability to act upon a detectable substrate. A particular target motif, in a test sample, can be assayed based on its ability to bind to a molecular affinity clamp.

As used herein, the terms "peptide," "polypeptide," and "protein" are used interchangeably and mean polymers of amino acid monomers linked by peptide linkages between carboxyl (COOH) groups and amine ($NH_2$) groups. A peptide may consist entirely of naturally occurring amino acid monomers, non-naturally occurring amino acids, or mixtures thereof. Unless denoted otherwise, whenever an amino acid sequence is represented, it will be understood that the amino acids are in N-terminal to C-terminal order from left to right. The term "polypeptide" may refer to small peptides, larger polypeptides, proteins containing single polypeptide chains, proteins containing multiple polypeptide chains, and multi-subunit proteins.

The term "amino acid", as used herein, refers to any amino acid, natural or non-natural, that may be incorporated, either enzymatically or synthetically, into a polypeptide or protein. Amino acids may also be altered. The term thus encompasses amino acids that have been modified naturally or by interaction. Examples may include, but are not limited to, phosphorylation, glycosylation, methylation, biotinylation, and any covalent and non-covalent additions to a protein that do not result in a change in amino acid sequence.

The term "label" as used herein refers to any tag, marker, or identifiable moiety. The skilled artisan will appreciate that many labels may be used in the methods of the invention. For example, labels include, but are not limited to, affinity tags, fluorophores, radioisotopes, chromogens, dyes, magnetic probes, magnetic particles, paramagnetic particles, electrophoretic molecules and particles, dielectrophoretic particles, phosphorescence groups, chemiluminescent, mobility modifiers, and particles that confer a dielectrophoretic change.

As used herein, the term "modulating" or "modulate" refers to an effect of altering a biological activity, especially a biological activity associated with a particular biomolecule. For example, an agonist or antagonist of a particular biomolecule modulates the activity of that biomolecule, e.g., an enzyme.

As used herein, the term "library" refers to any collection of two or more different polypeptides or proteins. In certain embodiments, a library may be a collection of polypeptides that have been modified to favor the inclusion of certain amino acid residues, or polypeptides of certain lengths.

As used herein, the term "variant" is meant to refer to a polypeptide differing from another polypeptide by one or more amino acid substitutions resulting from engineered mutations in the gene coding the polypeptide.

As used herein in connection with numerical values, the terms "approximately" and "about" are meant to encompass variations of ±20% to ±10% or less of the indicated value.

As is conventional, the terms "a" and "an" mean "one or more" when used herein, including in the claims.

As stated above, peptide motifs are high-value targets for affinity reagents. Many natural domains are known to bind to such motifs. Although natural peptide-binding domains could be used directly as affinity reagents, their inherently low affinity makes it difficult to do so (they do work in a limited number of cases (6)). Natural peptide-binding domains have evolved to mediate signaling networks by reversibly and weakly binding to a specific peptide motif (5). Thus, their sub-µM to low-µM $K_d$ values are optimal for efficient information flow in signaling networks, but are much too weak to function as robust affinity reagents.

One approach to enhancing the affinity of a peptide-binding domain is simply to optimize residues in and around the peptide-binding site. The common mode of interactions in these domains, however, is such that the target peptide and the binding domain bury a relatively small amount of surface area (5), limiting the affinity that can be achieved with simple optimization of the binding interface. In contrast, high-affinity interactions, such as those between an antibody and its antigen and those between calmodulin and its target, bury a large amount of surface area (7).

The principles embodying the invention provide a unique platform technology which, in one aspect, yields robust affinity clamps that have both high affinity and specificity for a target motif. The molecular affinity clamp strategy embodying the principles of the invention is fundamentally distinct from the standard antibody generation in that it exploits the binding specificity of naturally occurring domains that bind to a targeted peptide motif, but adds additional binding surfaces to the natural domain in the form of an "enhancer domain". The enhancer domain binds the target motif as does the natural domain. The resulting biomolecule thus has two modules that each recognize the targeted motif, and has a clamp-like or clamshell architecture that uses each half of the shells or each module to dramatically enhance affinity and specificity.

It is informative to compare characteristics of molecular affinity clamps with those of antibodies, the gold standard of affinity reagents. Antibodies are general and versatile affinity reagents. The immune system can produce an antibody to virtually any molecule. The diversity of the immunoglobulin repertoire is $10^{10-12}$, which is similar in size to the diversity of a typical phage display library ($10^{10}$). This versatility of the antibodies, however, also means that the antibody repertoire is not focused and that only a small subset of the naive repertoire is available to bind to a particular class of antigen. For example, antibodies that bind to lysozyme and those that bind to a phospho-Ser peptide are distinct subsets of the same repertoire.

Economical and scalable production is another important area of consideration for affinity reagents. As noted above, polyclonal antibodies cannot be reproduced, once the original stock is depleted. Monoclonal antibodies can be reproduced, but the maintenance and large-scale culture of hybridoma cells are cumbersome and expensive. Antibodies can also be produced by recombinant technologies, but the natural diversity throughout the antibody molecules (i.e., framework diversity in addition to the extensive diversity within the antigen binding loops) makes formatting them for different applications fundamentally low throughput.

Moreover, because of the presence of critical disulfide bonds, recombinant production of antibodies is not straightforward. For this reason, a number of alternative "molecular scaffolds" for engineering affinity reagents have been developed that are small and devoid of disulfide bonds (8-10).

Although these new-generation affinity reagents generally have good affinity and specificity, developing affinity reagents for short peptide motifs remains a major challenge in the field, because of the fundamental difficulties stated hereinabove.

In contrast, molecular affinity clamps in accordance with the invention are affinity reagents directed to a pre-defined motif. In one aspect, molecular affinity clamps are built with a particular interaction domain that is specific primarily to the class of target motifs that the interaction domain recognizes. Because of this pre-defined binding specificity, repertoire diversity can then be used to enhance the properties of affinity reagents rather than to blindly search for initial hits. This distinctive feature of the invention may lead to an increased success rate of producing high-affinity reagents for a motif of interest.

Reference is now made to FIG. A1 which is a schematic of the assembly of a modular molecular affinity clamp embodying the principles of the invention. The architecture of the affinity clamp is modular with two biorecognition modules, each capable of binding a target motif. The first biorecognition module has a recognition domain that possesses inherent or natural specificity for the target motif. The second biorecognition module also has a recognition domain that binds the motif. The two biorecognition modules are tethered together either directly, e.g., via a peptide bond between the two modules, or indirectly, e.g., via a linker moiety or linker. The affinity clamp is, in effect, a heterodimer with two different monomers, tethered together, each having affinity for the target motif. In most cases, the recognition domain of the second biorecognition module with appropriate binding characteristics is not known among naturally existing proteins, and thus is suitably engineered using library selection, rational design, computation design, or a combination of these strategies.

A target motif of interest is depicted in FIG. A1(a), illustrating the many proteins having domain/motif organization. FIG. A1(b) depicts the binding of a natural or primary binding domain of a first biorecognition module to the target motif. In one aspect, the primary binding domain is suitably an interaction domain. FIG. A1(c) depicts the binding of a second molecular recognition domain of a second biorecognition module at a second site of the target motif. The two biorecognition modules are linked directly or tethered together indirectly with a linker.

The two biorecognition modules are spatially oriented to bind distinct sites within the target motif. As shown in FIG. A1, the configuration of the two biorecognition modules about the target motif is clamp-like or clamshell-like, i.e., the target motif is "clamped" between the two biorecognition modules. As described above, the second recognition domain is referred to as the enhancer domain. By the binding of the second recognition domain to the target motif which is already bound to the first recognition domain, the affinity for the target motif is increased, the specificity is altered and/or the dissociation rate is decreased compared to the affinity of the natural binding domain alone.

In another aspect, the affinity clamp is suitably described as a ternary complex composition of the type

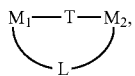

wherein $M_1$ and $M_2$ are first and second biorecognition modules, L is a direct bond or linker moiety used for tethering the first and second biorecognition modules, and T is a target motif. $M_1$ includes a first molecular recognition domain bound to a first site of the target motif, and $M_2$ includes a second molecular recognition domain bound to a second site of the target motif without disrupting the binding of the first biorecognition module. L as a linker is selected from the group consisting of a peptide which is equal to or shorter than 30 residues, a group capable of disulfide bonding, and a chemical crosslinker.

Molecular affinity clamps in accordance with the invention were synthesized. The affinity clamps were found to enhance the affinity of the starting domain (i.e., the natural or first recognition domain) by ~2,000 times, resulting in a dissociation constant in the low nanomolar range, comparable to those of available monoclonal antibodies to peptide motifs. Furthermore, the clamps also enhanced the specificity by >2,000 fold and extended the size of the motif that is recognized.

Target Motif

A target motif suitable in accordance with the invention may be any motif which can be recognized by a biorecognition module, e.g., an interaction domain. Such target motifs include peptides and covalently modified peptides, including but not limited to peptides that are phosphorylated, methylated, acetylated, ubiquinated, SUMOylated, ISGylated, glycosylated, acylated, prenylated, ribosylated, gammacarboxylated, or sulfated.

First Biorecognition Module

Among the commonly occurring domains identified in signaling proteins are the so-called "interaction domains." Interaction domains are typically small (usually less than ~100 amino acids) and autonomously folded. Many of them bind to short peptide motifs that often contain modified amino acids (5). It has been found that a primary binding domain, i.e., the first molecular recognition domain, of the first biorecognition module is suitably an interaction domain. With molecular affinity clamp technology, the interaction domains as the first biorecognition modules can be engineered in such a way that the enhancer domain can be connected in a proper orientation. The bifunctional module architecture of the molecular affinity clamps in accordance with the invention, after optimization, significantly increases the surface areas of the peptide-binding interface by forming the clamshell architecture, leading to higher affinity and/or specificity. Use of interaction domains as the primary binding domain is based on the following common features of these domains (5):

1. A target peptide motif binds to a shallow groove on the interaction domain surface, and the peptide is still highly exposed.
2. There are turns and/or loops located close to the peptide-binding site.
3. The N- and C-termini are juxtaposed in space so that they could be connected and a new set of termini could be created elsewhere.

In short, molecular affinity clamp technology makes it possible to define the primary specificity of affinity reagents in advance (e.g., using the specificity of the interaction domain), and then, enhance that affinity and/or specificity. This modular architecture in accordance with the invention transforms affinity reagent development from an "unguided fishing expedition" to a focused, rational and robust process.

Interaction domains, suitable as the first recognition domain, include, but are not limited to, domains involved in phosho-tyrosine binding (e.g. SH2, PTB), phosphoserine binding (e.g. UIM, GAT, CUE, BTB/POZ, VHS, UBA, RING, HECT, WW, 14-3-3, Polo-box), phospho-threonine binding (e.g. FHA, WW, Polo-box), proline-rich region binding (e.g. EVH1, SH3, GYF), acetylated lysine binding (e.g. Bromo), methylated lysine binding (e.g. Chromo, PHD), apoptosis (e.g. BIR, TRAF, DED, Death, CARD, BH), cytoskeleton modulation (e.g. ADF, GEL, DH, CH, FH2), or other cellular functions (e.g. EH, CC, VHL, TUDOR, PUF Repeat, PAS, MH1, LRR, IQ, HEAT, GRIP, TUBBY, SNARE, TPR, TIR, START, SOCS Box, SAM, RGS, PDZ, PB1, LIM, F-BOX, ENTH, EF-Hand, SHADOW, ARM, ANK).

Second Biorecognition Module

An enhancer domain, i.e., the molecular recognition domain of the second biorecognition module, is suitably an engineered polypeptide of selected affinity for the target motif. It is engineered, in effect, as a single domain antibody mimic. The enhancer domain is suitably a polypeptide scaffold capable of presenting diverse amino acid combinations at surface exposed positions. In accordance with the general architecture of molecular affinity clamps, scaffolds that are capable of presenting a functional surface of sufficient size (estimated it to be ≥5 residues) may serve as an enhancer domain. Peptide scaffolds suitable as enhancer domains include, but are not limited to FN3, affibodies, APP, camelid $V_HH$, ankyrin repeats, and disulfide-constrained peptides (9-11). While there are a number of alternative scaffolds, given the track record of the FN3 scaffold, the FN3 platform provides an excellent foundation to engineer molecular affinity clamps. Another suitable enhancer, a disulfide-constrained peptide, is also demonstrated in the Examples below.

FN3 is an autonomous domain of an extracellular matrix protein, fibronectin. It is a prototype of a large family of proteins, many of which are involved in target binding (12). Among many FN3 domains, the tenth domain of FN3 of human fibronectin is often used. As used herein, hereafter this particular FN3 is simply referred to as "FN3". The effectiveness of this scaffold has been validated by independent groups (14,15). FN3 (SEQ ID NO: 145) is 94 residues long, highly stable and devoid of disulfide bonds. It can be expressed at an extremely high level in E. coli. Its structure, dynamics and folding have been extensively characterized (16-20).

Engineered FN3 variants bind to a variety of targets (37-40). There are established phage display, yeast surface display and yeast two-hybrid screening systems for FN3, demonstrating the compatibility of this scaffold for both the intracellular and extracellular environment.

In an illustrated embodiment, the tenth domain of fibronectin, i.e., FN3, (see, FIG. B1) was used as the scaffold for the enhancer domain. FN3 was found to be a particularly advantageous enhancer scaffold for constructing molecular affinity clamps, because (i) it functions in both reducing and oxidizing conditions, (ii) three surface loops are available for engineering a binding site, allowing for structural adjustment that may be needed to accommodate different target peptide motifs, (iii) FN3 has a highly stable core, and its function is not perturbed by fusion of a foreign protein at either termini, (iv) it can easily be prepared in large quantities, and (v) the inventors have extensive experience in the construction and selection of FN3 combinatorial libraries and possess reagents for making them. FIG. B1 is a ribbon drawing of FN3 with the beta-strands A-G and the three loops that are diversified in libraries.

In a further illustrated embodiment, a disulfide-constrained peptide was used as the enhancer domain. Although this domain has no similarities to the FN3 domain, it is able to enhance binding to the target peptide by at least 12-fold. Thus, other enhancer domains, besides FN3, can be used in embodiments of this invention, demonstrating the generality of affinity clamp technology and its "plug-and-play" aspect.

Linkers

The two biorecognition modules may be linked together either directly, e.g., bound together with a peptide sequence via a tail from one of the modules, or indirectly via a linker. As to the latter, the linker generally is bifunctional in that it includes a functionality for linking the first biorecognition module and a functionality for linking the second biorecognition module. The linker may suitably be a specific moiety, such as an amino acid sequence of about 30 or fewer residues. It is also contemplated that the two biorecognition modules may be linked non-covalently through a high affinity binding interaction or physical association such as the interaction mediated by coiled-coil peptides.

A common feature of interaction domains is that their N- and C-termini are juxtaposed and located far away from the peptide-binding interface. Although it was initially thought that simply connecting an enhancer domain at one of the natural termini would not lead to the clamp architecture, the inventors have found in some embodiments that such termini could be used with a longer tether or linker.

It was also found, however, that by circularly permutating the interaction domain, the termini can be located closer to the peptide-binding site. For example, a PDZ domain and an SH3 domain tolerate circular permutation (21). Many interaction domains can be circularly permutated to yield new termini with minimal effect on their function. As noted, however, in some embodiments, circular permutation is not needed.

Detection of Affinity Clamp Binding

In general, the different conformational states of modular affinity clamps used in accordance with the invention will correspond to different separation distances between the first and second biorecognition modules, whereby changes in conformation may be conveniently monitored by means of a separation sensitive signal.

Various forms of separation sensitive signal systems may be used with the affinity clamps of the invention. In such embodiments, the first biorecognition module includes a first signaling moiety and the second biorecognition module includes a second signaling moiety, and the first and second signaling moieties are capable of interacting to produce a detectable signal. The signaling moieties may include dyes, quenchers, reporter proteins and quantum dots. Particularly useful are embodiments in which the biorecognition modules include optical signaling pairs that can produce a detectable signal when the proximity of the modules with respect to each other changes with the binding of the first and second recognition domains. Suitably, the first and second signaling modules are a fluorescence resonance energy (FRET) donor group and a receptor group, respectively. The change in proximity of the FRET groups produces an optical signal which differs between when the target motif is present and not present.

It will also be appreciated that various other means may be used for "reading" the presence of target motif binding to a modular affinity clamp, and/or the resultant change in conformational state of the affinity clamp structure. Many different labeling systems may be used, such as fluorophore labeling (including quantum dot), radio-labeling, and redox labeling.

Use of Affinity Clamps as Biosensors

Molecular affinity clamps in accordance with the invention may be suitably used as a biosensor wherein the first and second biorecognition modules are each labeled with paired signaling moieties as described above.

A plurality of affinity clamps described herein may be immobilized, directly or indirectly to a support or substrate to form an array of clamps or an array of biosensors. Supports or substrates can take a variety of forms such as polymers, glasses, metal and those with coating therein. Arrays are ordered arrangements of elements, allowing them to be displayed and examined in parallel. Arrays of immobilized affinity clamps can be used to detect the target motif and demonstrate the binding reaction. Certain array formats are sometimes referred to as "biochips." Biochips may include a plurality of locations configured so that each location is spatially addressable. Typically, the clamp format is configured in a row and column format with regular spacing between locations, wherein each location has machine-readable (e.g., computer-readable) information to identify the location on the surface of the substrate.

The affinity clamp technology provides a method of detecting the presence and amount of a target motif in a sample by using the affinity clamp as a biosensor. Specifically, a sample is contacted under specific conditions with a biosensor. Fluorescence events are sensed with the binding of the first and second biorecognition modules to the target motif in the sample and in the absence of the sample, and the fluorescence sensing in the absence of the target motif is correlated with a change in the FRET signal in the presence of the target motif. Thus, absence of the target motif generates a specific FRET signal in terms of the wavelength and amplitude of the emission, and the presence of the target motif generates a modulated FRET signal emission in terms of either the wavelength or amplitude or both. Samples may include blood, saliva or tissue.

Accordingly, an affinity clamp array as a biosensor array includes a plurality of affinity clamps or biosensors anchored to the surface of a substrate, each at an addressable site on the substrate.

Construction of a Modular Molecular Affinity Clamp

Reference is made to FIG. B2 wherein the general molecular affinity clamp engineering procedures are depicted and are summarized below. In FIG. B2, the asterisks denote mutations and the phage portion is not drawn to scale.

The general engineering of a molecular affinity clamp is given basically in four steps using FN3 as an exemplary enhancer domain. Step 1 involves identifying the potential locations for attachment of the second biorecognition module to the first biorecognition module by visual inspection of the domain structure and/or from sequence variability among domain family members, and testing the tolerance of identified locations for extensive modifications, for example, by inserting four Gly residues.

Step 2 includes two sub-steps, Step 2a and 2b. Step 2a is included if circular permutations are performed to construct new termini closer to the interaction domain binding site. In some embodiments, Step 2a is not needed. In Step 2a, if circular permutation is performed, a domain is constructed by joining the original termini and cutting the polypeptide at a location closer to the target-binding site of the interaction domain that tolerates mutations. Then, in Step 2b, the second biorecognition module (i.e., enhancer (e.g., FN3) scaffold) is attached to the C-terminus of the circularly permutated domain or the natural C-terminus (in the case where no circular permutation is performed.) The N-terminus of FN3 is located close to its functional loops, and thus, connecting the FN3 N-terminus to the interaction domain ensures that the FN3 binding loops are facing the target motif-binding site.

In Step 3, amino acid diversity is introduced in FN3 loops to construct a large combinatorial library of mutated polypeptides, and in Step 4, library sorting is performed to optimize the enhancer domain for a specific motif.

Generation of High-Performance Affinity Clamps for a Short Peptide Motif

In an illustrated embodiment, a PDZ domain (SEQ ID NO: 146) was used in constructing an affinity clamp system, because of PDZ's favorable attributes. Extensive structural and functional information of the PDZ domains exists, and the inventors have access to HTP tools used in characterizing affinity and specificity (described below).

PDZ domains are ~100 residues long and bind to the extreme C-termini of other proteins (22). They bind to the (S/T)X(I/L/V) (SEQ ID NO: 67) —COOH motif (where COOH denotes the C-terminus) in general, and individual PDZ domains exhibit more extensive and complex specificity. The free C-terminus represents a unique chemical signature in a peptide motif, which is conceptually equivalent to the phosphate group in phospho-peptide motifs.

The PDZ domain of Erbin (1N7T), a member of the LAP (leucine-rich repeat and PDZ-containing) family was used (see, FIG. C1). It is a particularly well-characterized PDZ domain (23,24). The PDZ recognizes the C-terminus of p120-related catenins (α-catenin and Armadillo repeat gene deleted in Velo-cardio-facial syndrome (ARVCF)), and it also weakly binds to ErbB-2 (25).

A phage display system for the PDZ domain-enhancer domain fusion was constructed. Phase display technology is readily used in the construction of modular affinity clamps. Phage display is a well known technique by which variant polypeptides are displayed as fusion proteins to at least a portion of the coat protein in the surface of the phage particles. An advantage of phage display lies in the fact that large libraries of protein variants can be rapidly and efficiently sorted for those sequences that bind to a target motif with high affinity. The display of the PDZ domain was confirmed by the binding of the PDZ-displaying phages to the target motif, GGRSWFETWV (SEQ ID NO: 68) —COOH(COOH denotes the C-terminus) (24).

The phage display system used herein displays a protein of interest at the N-terminus of the M13 phage minor coat protein, p3 (30). The inventors have found that a co-translational secretion signal (DsbA) (SEQ ID NO: 147) developed by Pluckthun's group (31) improves the display level of FN3 by ~100 fold over the conventional system with a post-translational signal (OmpT) (30). The high stability of FN3 seems to inhibit efficient post-translational secretion of the FN3-phage p3 fusion protein that is necessary for its assembly into phages. Because interaction domains are often stable, the co-translational phage-display system is useful. As shown above, the PDZ domain fused to the FN3 domain was successfully displayed using this system. The Grb2-SH2 domain fused to the FN3 domain was also successfully displayed on the phage surface using this system. (See, FIG. C7 wherein the binding of SH2-displaying phages to targeted-coated (black bars) and control surfaces (white bars) are shown.)

The molecular affinity clamp was produced as a fusion protein linked to the C-terminus of yeast SUMO (26). The peptide can be cleaved with a SUMO-specific protease. Most experiments were with the uncleaved fusion proteins, and results were confirmed with free peptides. In all cases, the attachment of SUMO had no detectable effects on binding data (not shown).

From visual inspection of the erbin PDZ structure and a sequence alignment of PDZ domains, three potential sites were identified for the new termini in a circularly permutated PDZ domain. Three mutant PDZ domains, in which four Gly residues were inserted in one of the three candidate sites, were assayed for binding to the target motif using the phage display format. (See, FIG. C1A in which the bound peptide is shown as sticks, and the positions for a Gly$_4$ insertion tested are indicated with the arrows and labeled with residue numbers and qualitative description of the effects; FIG. C1B illustrates a view after ~90° rotation about the horizontal axis.) Only one (52/53) showed severely reduced binding, indicating that the other two positions tolerate drastic modifications. (FIG. C1C shows the binding of wild-type and loop insertion mutants to a target peptide, as measured using phage ELISA.)

A circularly permutated PDZ domain was then constructed (referred to as "cpPDZ") in which the original termini were connected with an Asn-Gly linker and the new termini were created by disjoining between residues 20 and 21. The Asn-Gly linker has a high propensity to form a turn and is thus suitable for connecting the termini. cpPDZ maintained the target motif binding activity. Surface plasmon resonance (SPR) characterization revealed that its affinity was only slightly reduced relative to the wild-type PDZ domain (data not shown).

A fusion protein of cpPDZ and FN3 in the phage display format was constructed in which FN3 was fused to the C-terminus of cpPDZ (See, FIG. C2 which is a schematic representation of enhanced PDZ, with the FN3 loops that were diversified in the library.). The addition of FN3 did not alter the affinity of cpPDZ (Table 2 and FIG. C3).

Amino acid diversity was then introduced in three FN3 loops, i.e., BC, DE and FG, (Table 1 and FIG. C2) that constitute a contiguous surface. The total sequence diversity of this library was ~10$^9$.

Using semi-automated methods, the phage display library was sorted using an eight-residue motif (SEQ ID NO: 148) corresponding to the ARVCF C-terminus. As seen In FIG. C3 utilizing SPR (BIAcore) analysis of motif binding of ePDZ's and the parent proteins, the left and right columns show data with the ARVCF and δ-catenin epitopes, respectively. The maximal motif/affinity concentrations are indicated. In B, C and F, the on and off rates are also shown on the left and right sides, respectively. The affinity of the starting material (cpPDZ-FN3) was weak with a K$_d$ of ~25 µM. After four rounds of sorting, two clones with high affinity were identified to the ARVCF peptide motif. ePDZ-a (SEQ ID NO: 149) and ePDZ-b (SEQ ID NO: 150) are thus (referred to as "enhanced PDZ-a" and "enhanced PDZ-b" or simply "ePDZ-a" and "ePDZ-b" respectively) potential affinity clamp candidates.

These two clones were characterized as soluble proteins. They both had a K$_d$ of 56 nM as determined by surface plasmon resonance (SPR) (FIG. C3 and Table 2), which corresponds to ~500 fold affinity enhancement when compared with cpPDZ, i.e., the starting material. This large affinity enhancement achieved with the molecular affinity clamp strategy compares very favorably with that by the standard affinity maturation of another PDZ domain where only a 25 fold enhancement to ~600 nM K$_d$ was accomplished after multiple rounds of library selection (27).

The binding specificity of the ePDZ clones was investigated. In addition to the ARVCF motif, wild-type erbin PDZ also binds to the C-terminus of δ-catenin with a low µM K$_d$. The two sequences differ only at positions outside the core recognition motif, DSWV (SEQ ID NO: 69) —COOH (Table 2). The affinity enhancement of ePDZ-a was similar for both targets. Remarkably, the ePDZ-b clone had very weak binding to δ-catenin, similar to the wild-type PDZ domain, showing that ePDZ-b discriminates between the two targets by ~200 fold. Equally importantly, ePDZ-b discriminates amino acids outside the DSWV-COOH motif shared by the two peptides (Table 2), and thus, it expanded the size of the target motif. The improved specificity is consistent with the molecular affinity clamp design where the enhancer domain binds to the motif surface presented on the PDZ domain and thus can "read" the motif sequence (FIG. C2). These results established that the molecular affinity clamp technology can dramatically enhance both affinity and specificity of the original interaction domain.

The ePDZ samples were monomeric as judged by size-exclusion chromatography and by NMR spectroscopy. The $^1$H, $^{15}$N-HSQC spectrum of free ePDZ-a showed excellent dispersion of cross peaks, indicative of a highly structured protein shown in FIG. C4 (black dots; each dot corresponding to signal from an amide H-N pair). Upon addition of the target peptide motif, a large number of peaks shifted, consistent with the presence of a large interface between the protein and peptide motif, as expected from the design (FIG. C4, gray dots).

The ePDZ affinity clamps withstand harsh treatment. The two clones remained monomeric and retained full activity after incubation at 50° C. for two hours (See, FIG. C5 wherein the effects of heat treatment on state (A) (monomeric state not affected) and (B) on binding properties are shown; only data for ePDZ-a is shown). Because they lack disulfide bonds or free Cys, they are naturally resistant to reducing reagents such as DTT and p-mercaptoethanol.

The high affinity of the PDZ-FN3 clamps is comparable to that of typical antibodies. The PDZ-FN3 affinity clamps functioned well in Western blotting and in immunoprecipitation (pull down) assays. In FIG. C6A, Western blotting is shown wherein E. coli lyase containing 5 nanograms of SUMO-ARVCF fusion protein was used as the input (lane 2; CBB staining, i.e. loading control). ePDZ-a and ePDZ-b (lanes 3 and 4) detected the target but the wild-type PDZ did not (lane 5). Lane 6 is a negative control for the secondary, anti-FLAG antibody. In FIG. C6B, pull-down (immunoprecipitation), biotinylated ePDZ's and streptavidin (SA)-magnetic beads were used. The input (I), unbound (U), wash (W) and bound (B) fractions were separated with SDS-PAGE and detected with CBB. Note that this is not Western blotting, which would have given higher sensitivity and specificity. The two ePDZ's precipitated the target (lanes 4 and 7; marked with the triangles) but the circularly permutated PDZ-FN3 fusion (cpPDZ; i.e. the starting material) did not (lane 10). Note that most of nonspecific binding is due to the SA-magnetic beads (lane 13). These results indicate that molecular affinity clamps are antibody alternatives. It is noted that the relatively low recovery of the target in the pull-down assays may be due to the fact that the off-rate was optimized for these clamps (FIG. C3). If desired, affinity and off-rate can be improved by affinity maturation processes, as demonstrated below.

X-Ray Crystal Structure of the Affinity Clamp

The crystal structure of enhanced PDZ-a (ePDZ-a) was determined at 1.7 Å complexed with its target peptide motif (See, FIG. E1 illustrating a cartoon drawing of the crystal structure with the circularly permutated PDZ domain (cpPDZ), FN3 and the peptide are shown; the peptide termini are also indicated.) As shown in FIG. E1, the overall architecture of the affinity clamp in the crystal structure is similar to the original model (FIG. C2). The structure reveals that the target peptide motif is almost completely buried between the two domains and that all three loops of FN3 (the enhancer domain) interact with the PDZ-peptide complex. The atomic structure confirms that the affinity clamp functions as designed.

Affinity Enhancement

Library Sorting

To generate more ePDZ's that are distinct from the identified two clones (ePDZ-a and ePDZ-b; Table 1), new clones are added to the pool of starting ePDZ's for affinity maturation experiments. In affinity maturation, individual loops are optimized separately by phage display. After these initial sorting steps that enrich functional sequences in individual loops, the individual loops are combined (i.e., "shuffled") to make the final library. This strategy ensures a large number of sequences while maintaining the binding mode of the starting clone.

Libraries are constructed using the high-efficiency Kunkel mutagenesis method (32-34) that reliably produces ~$10^{10}$ independent members. Semi-automated and highly streamlined protocols for phage display library screening employing a magnetic beads-handling robot ("KingFisher", Thermo Corporation) (See, FIG. D1 outlining HTP library screening procedures) (30) have been developed. With this robot that moves magnetic beads between the wells of a 96-well plate, 12 selection reactions can be performed in an automated manner.

The biotinylated target at a low concentration (≤1 nM) is incubated with a phage-display library in solution, and library members bound to the target motif are captured using streptavidin magnetic beads. In sorting the final, highly enriched library, the stringency is increased using the "off-rate" selection. In this method, after a phage library is allowed to bind to a biotinylated target, an excess amount of a non-biotinylated target is added as a competitor so that rebinding of the biotinylated target is prevented. This sorting scheme primarily selects variants with a slow off-rate, which is an excellent indicator of high affinity.

Successful selection is confirmed with two parameters— (1) the "enhancement ratio" and (2) the "hit ratio." The enrichment ratio is the number of phages recovered from selection with a target over that from control selection without the target. The hit rate is the number of target-binding clones in a randomly picked number of clones, typically eight. An enrichment ratio of 20 or greater indicates a success, wherein 50% of clones have desired properties. Automated procedures for this assay have been established using a liquid-handling robot (Biomek 2000, Beckman). An additional round of selection is performed if a low enrichment ratio is observed. Selected clones are reformatted into free proteins with a $His_8$-tag. This is done simply by introducing $His_8$ and a stop codon between the molecular affinity clamp gene and the phage p3 gene. Proteins are expressed in a small scale using a deep 96-well plate and purified with Ni-affinity magnetic beads (Novagen) in an automated manner using a KingFisher instrument.

The length and sequence of the linker between the PDZ and FN3 portions are also optimized. Library construction and screening is performed in the same manner as described above.

Improved Affinity of the Affinity Clamp

One method to improve affinity of the affinity clamp is to improve the interaction interface of the enhancer domain (e.g. the FN3 domain). Amino acid diversity was introduced in the BC and FG loops of the FN3 domain of the first-generation affinity clamp, ePDZ-b, and variants that showed enhanced binding were selected. The sequences are listed in Table 4. The two second-generation variants, ePDZ-b1 (SEQ ID NO: 151) and ePDZ-b2 (SEQ ID NO: 143), were prepared as protein samples and their binding properties were analyzed using SPR. Results are summarized in Table 4. The dissociation constants of the ePDZ-b1 and ePDZ-b2 for the AVFCF peptide were 5 and 4 nM, respectively, which were significantly smaller than the parent protein, ePDZ-b (56 nM) and represent 5,000-6,000-fold affinity enhancement relative to the original PDZ protein. The affinity enhancement primarily originated from reduced dissociation rates. The affinity-matured clones also had a much slower dissociation rate as measured by SPR (see, FIG. E2A showing binding kinetics of an affinity matured ePDZ that show much slower dissociation than its parent molecule (compare with FIG. C3C), with a half-life of 45 minutes, corresponding to a 20-fold improvement over the first generation ePDZs and substantially more improvement over the wild-type PDZ whose dissociation rate was too fast to measure.

These $K_d$ values and dissociation rates compare favorably to those for monoclonal antibodies. The reduced dissociation rate of an affinity clamp improves its usefulness in immunochemical applications. As demonstrated in FIG. E2(b) (immunoprecipitation performed in the same manner as in FIG. C6; Lane 1, ePDZ only; lane 2, input; lane 3, unbound; lane 4, wash; lane 5, captured; SA: streptavidin), immunoprecipitation using affinity-matured ePDZs captured substantially larger amounts of the target protein motif from cell extracts than the first generation ePDZs as seen by comparison of FIG. E2B lanes 5 and 7 with FIG. C6b.

The affinity maturation process also dramatically enhanced the specificity of these affinity clamps. ePDZ-b1 and ePDZ-b2 can discriminate the AFVCF peptide (PQPV DSWV (SEQ ID NO: 66) —COOH) and a homologous target from δ-catenin (PASPDSWV (SEQ ID NO: 70) —COOH; identical segment underlined) by more than 2,000 fold, while the wild-type PDZ domain binds to them almost equally. Because the four C-terminal residues of the two peptides are identical, which are the primary recognition motif by the original PDZ domain, the stringent discrimination by these affinity clamps clearly indicates that the affinity clamp strategy can expand the size of recognition motif.

The affinity-matured affinity clamps performed exceedingly well in immunochemical assays. ePDZ-b2 captured a target peptide from *E. coli* lysate in a highly specific and quantitative manner. Its performance in Western blotting of ARVCF in mammalian cell lysate was superior to that of a commercially available monoclonal antibody.

Construction of Affinity Clamps without Circular Permutation

To create a ePDZ-a without the circular permutation step of an interaction domain, the C-terminus of the wildtype PDZ domain was connected to the N-terminus of the engineered FN3 domain from ePDZ-a with a long linker. The linker was tethered to PDZ with a disulfide bond introduced between a Cys residue within the linker and a Cys introduced at position 20. Target binding of this clamp was similar to that of ePDZ-a (FIG. E3) and decreased upon the reduction of the disulfide linkage. FIG. E3 shows target binding of affinity clamps without circular permutation shown as "a" in the graph and as schematics (a) and (b); "b" in the graph is ePDZ-a (positive control) and "c" is PDZ only (negative control). Thus, the application of the affinity clamp technology of this invention may extend to domains that may not tolerate circular permutation, broadening the applicability of the technology in accordance with the invention.

Specificity Enhancement

To ensure consistent selection of highly specific binders, library selection is performed in the presence of excess competitors, e.g. peptide motifs with slightly different sequences from the target's sequence.

The specificity of ePDZ's is evaluated using complementary methods. SPR is used as described above to determine affinities to a panel of peptides, and to identify highly specific ePDZ's. The C-terminal phage display library that has been used to define the sequence specificity (24, 25, 35) is then used. This type of C-terminal peptide library is sorted using an ePDZ of interest as the binding partner, and the binding specificity determined from the amino acid sequences of enriched clones, which can be readily done by HTP DNA sequencing. ePDZ's are also tested in Western blotting to characterize their "practical" specificity.

Peptide Library Selection

The ePDZ-b family of affinity clamps exhibits the ability to discriminate the ARVCF peptide (PQPV<u>DSWV</u> (SEQ ID NO: 66) —COOH) and its homologue, the δ-catenin peptide (PASP<u>DSWV</u> (SEQ ID NO: 70) —COOH; identical sequence underlined). This high specificity is in contrast to those of the parent PDZ domain and of ePDZ-a, which show essentially no difference in affinity to these peptides.

To characterize the levels of specificity, selection of C-terminal peptides that bind to PDZ clamps from large phage-display libraries was performed. In this approach, peptide sequences that bind to the PDZ domain or a PDZ clamp are selected, from which binding specificity is deduced. Briefly, these libraries are constructed by attaching a short peptide segment to the C-terminus of the M13 p8 protein, and then diversifying its sequence. (See, FIG. E4 showing sequences of isolated clones from C-terminal peptide libraries; sequence LOGO representations of sequences are also shown.)

Initial characterization was performed using a library containing seven randomized amino acids. Since the PDZ clamps preserves the underlying specificity of the parent PDZ domain that shows specificity for the C-terminal 4 residues, the C-terminal 4 positions of this peptide library was biased toward the known specificity. After three rounds of library sorting, enriched clones were sequenced. The results show that clones sorted with the ePDZ-b family members show convergence in sequence (FIG. E4). The C-terminal four positions completely converge to DTWV (SEQ ID NO: 71) —COOH, which is identical to the consensus binding motif of the starting PDZ domain, D(S/T)WV-COOH. The N-terminal three residues that are fully randomized also show some levels of sequence convergence. Ile, Leu and Met are found at the −4 position (Val in the ARVCF target), Asn and Pro are common at the −5 position (originally Pro) and Gly and Ser are common at the −6 position (originally Gln). These results suggest that the ePDZ-b family of PDZ clamps has a higher degree of binding specificity than the starting PDZ domain.

To further characterize the sequence specificity of ePDZ-b1 at the positions outside the C-terminal D(S/T)WV sequence, another library was constructed in which the C-terminal four residues were fixed as DSWV and the five preceding positions were completely diversified. Sorting of this library using ePDZ-b1 resulted in sequence convergence to (R)(G/S/neutral)X(I/L/M)DSWV (SEQ ID NO: 72), and sorting with ePDZ-b2 resulted in further conversion at the −4 position to (R)(G/S/neutral)(<u>N/S</u>) (I/L/M)DSWV (SEQ ID NO: 73). Not unexpectedly, these patterns closely resemble the ARVCF sequence. It is remarkable that ePDZ-b1 and ePDZ-b2 exhibit high binding specificity even at −7 position, indicating that the affinity clamping strategy can significantly expand the size of the binding domain relative to that of the original interaction domain, in this case, the PDZ domain.

Alanine-Scanning Analysis

To complement the library sorting experiments described above, Ala-scanning experiments of the ARVCF peptide were performed. When the goal is to define differences in the ability of ePDZ-a and ePDZ-b1 to recognize the differences between the ARVCF and δ-catenin peptides, only those positions that differ between the two peptides are analyzed.

Consistent with the peptide library sorting results, the ePDZ-b family was sensitive to Ala substitution mutations at all positions between −4 and −7. FIG. E5 shows the effects of Ala substitution of the ARVCF peptide on the binding affinity of PDZ clamps. The results are shown in terms of changes in free energy change ($\Delta G = -RT \ln(Kd^{mutant}/Kd^{wild\ type})$). A positive value indicates that a mutation at the position decreases binding affinity. The tested positions are −7 to −4 in the ARVCF peptide (<u>PQPV</u>DSWV-COOH; mutated positions are underlined). For each mutant, binding affinity was determined using surface plasmon resonance as described previously for the wild-type ARVCF peptide (69). As seen in particular, Ala substitution at position −4 results in the largest reduction in affinity by over 200 fold. In contrast to the ePDZ-b1 data, ePDZ-a is much less sensitive to the Ala substitutions at all positions tested, as expected from the peptide library results. These results further support the exquisite binding specificity of the ePDZ-b family of affinity clamps.

Together, these analyses have established that the affinity clamp strategy can achieve a dramatically high level of binding specificity far beyond that can be achieved with an isolated interaction domain.

Engineering New Binding Specificity

Two complementary approaches are used to engineer specificity: (1) increasing the specificity of the first recognition domain, and (2) broadening the specificity spectrum of a highly specific signaling domain. Erbin PDZ is quite specific, with a consensus sequence of (E/D)(T/S)WV (SEQ ID NO: 74) —COOH (24,25). Other PDZ domains have broader specificity. For example, α-1-syntrophin PDZ has a consensus sequence of E(S/T)X(LIV) (SEQ ID NO: 75) —COOH where X is any amino acid, and it is predicted to bind to over 1,500 of all possible 4-residue peptides with a $K_d$ less than 50 μM (36). Thus, it is suitable for the first approach.

For the first approach, a combinatorial library is constructed of a circularly permutated α-1-syntrophin PDZ fused to FN3 in the same manner as for erbin PDZ (FIG. C2). A panel of target motifs is prepared containing Ile, Leu or Val at the C-terminal residue (position 0 according to the standard PDZ ligand numbering), Ser or Thr at the (−2) position and those containing one of 20 amino acids at the (−1) and (−3) positions. Also, the preference to Glu at (−3) of α-1-syntrophin PDZ is not strong (36). Using the SUMO fusion method, a collection of such peptide motifs is made. Amino acid diversity is introduced using degenerate oligonucleotides. Sequencing a sufficiently large number of clones (e.g., 96) provides a thorough and economical coverage of possible peptide sequences. Selections and characterization are performed as described above. Library screening is performed in the "competition" mode as described above to determine which ePDZ's have distinct motif specificity. Selected ePDZ's are labeled with rhodamine and their binding is tested using the quantitative protein microarrays (described below) where each well contains 96 different peptide motifs in the form of SUMO fusion.

The second approach is guided by structure-function and redesign studies that have shown that a few positions are responsible for specificity differences (37,38). The amino acid identities at F25 and I27 (erbin PDZ numbering) are responsible for the specificity at the C-terminal residue. Likewise, H79 is responsible for the strong preference to (T/S) at the (−2) position (PDZ ligands are numbered with zero corresponding to the C-terminal residue), and when it is replaced with an Arg in ZO1-PDZ3, no specificity at this position is observed. Focused amino acid diversity is introduced in the PDZ domain based on the above analysis, and library sorting is performed using a series of closely related peptide motifs.

Protein Array Evaluation

A quantitative protein array platform was also developed (1). A non-contact arrayer (BioChip Arrayer; Packard Biosciences) was used to dispense proteins. It allows for extremely reproducible spotting morphology and volumes (<5% variation between replicate spots) that enabled the comparison of intensities among multiple spots. This is fundamentally different from the standard microarray platform where the relative intensities of two differently colored molecules are compared on a single spot. Furthermore, a total of 96 identical microarrays can be fabricated in the standard 12 by 8 pattern onto custom-made glass slides of microtiter-sized proportions so that each array fits into individual wells of a microtiter plate. The spatial separation of arrays allows titration of ligands into each array. Using this system, quantitative characterization of interactions of most of the human SH2/PTB domains with phosphopeptides derived from ErbB receptors were successfully characterized in a HTP manner (1). This technology for HTP characterization of the affinity and specificity of molecular affinity clamps can be used herein.

Generation of High-Performance Affinity Clamps for Phospho-Peptide Motifs

To engineer high-performance affinity reagents for pSer-, pThr- and pTyr-containing peptides, the molecular affinity clamp technology is applied to the WW and SH2 domains as the primary interaction domain (5,41,42). It is noted that both these domains recognize critical motifs in cancer-related signaling networks. As they are structurally distinct from the PDZ domain used in PDZ-FN3 clamp construction, construction of these clamps expands the generality of the molecular affinity clamp technology.

The design procedures outlined above (FIG. B2) are applied to the Pin1 WW domain that binds to the pSer-Pro and pThr-Pro motifs (FIG. D2 shows in (A) the Pin1 crystal structure; the segment connecting the domains is disordered in the structure; in (B) a representation of the designed interactions between the WW and FN3 domains in an eWW protein is shown; the three binding loops of FN3 and the termini are labeled)) (43,44) and to the Grb2-SH2 domain that binds to pTyr-containing molecular motifs (45,46). (FIG. D3 is a cartoon representation of Grb2-SH2 domain bound to a pY-containing peptide (PDB ID: 1TZE).) The bound peptide is shown as sticks. Potential positions for the new termini after circular permutation are marked. The bottom figure is a side view. The termini are also marked.)

In generating pTyr-binding molecular affinity clamps, the Grb2-SH2 domain was used. The SH2 domain of Grb2 ("Grb2-SH2" hereafter) is ~98 residue autonomously folded domain that binds to a peptide containing a phospho-Tyr (pY) residue (51, 52). This is a well-characterized protein that binds to a consensus sequence of pY(Q/YV)N(Y/Q/F) (SEQ ID NO: 76) (51,52). A recent study showed that except for Asn at the (p+2) site, it has very broad binding specificity (53), suggesting the possibility of making a diverse set of molecular affinity clamps using a single SH2 domain. A phage display system for this domain (FIG. C7) has already been established. Grb2-SH2 binds to a number of important molecules in the receptor tyrosine kinase networks, including ErbB2 (HER2) and c-MET, both of which are intimately involved in multiple cancers (54-60). Initial target peptide motifs are chosen among known targets of Grb2 (Table 3).

As commonly found in interaction domains, the termini of Grb2-SH2 are located on the opposite side from the peptide-binding site of the molecule (45). Therefore, it was necessary to relocate the termini in order to create the clamp architecture, as was done in the case for the erbin PDZ domain (69).

A synthetic gene for human Grb2-SH2 (corresponding to residues 56-153 of GenBank accession number NM_002086.3) (SEQ ID NO: 77) was constructed and cloned in a phage display vector (30). The functional display of Grb2-SH2 on the surface of phage was confirmed by the detection of binding of phages displaying Grb2-SH2 to a cognate pY-containing peptide corresponding to residues 1130-1146 of ErbB2 (HER2) pY1139 (amino acid sequence: PLTCSPQPEpYVNQPDVR) (SEQ ID NO: 78).

Insertion mutations were first employed to identify loops that tolerate extensive structural changes. Four Gly residues were inserted between residues G114-A115, V122-V123 or R142-N143, respectively, and the binding function of these three insertion mutants was assessed using phage ELISA. The Gly4 insertion between V122-V123 was found to minimally affect the peptide-binding function of Grb2-SH2, and thus, this position was chosen to be the new termini for circular permutation.

The natural termini (residues H58-I151) were connected with a linker (GGSGGG (SEQ ID NO: 135) or GGSGGSG (SEQ ID NO: 139)) and the new termini were created between V122-V123. This circularly permutated SH2 domain, referred to as "cpSH2" hereafter, retained the peptide-binding function as tested using phage ELISA.

The cpSH2-FN3 fusion protein was then constructed by connecting the FN3 gene to the 3' of the cpSH2 gene in the phage display vector. A short linker (GGSGGS) (SEQ ID NO: 99) was used between the two domains. As expected from the inert nature of the FN3 scaffold, the addition of FN3 did not significantly affect the function of cpSH2. The three recognition loops (BC, DE and FG loops) of the FN3 scaffold in the SH2-FN3 fusion were diversified. The BC and FG loops were diversified using a biased amino acid composition (a mixture of the following amino acids composition: Tyr, 30%; Ser, 15%; Gly, 10%; Phe, 5%; Trp, 5%; all other except for Cys, 2.5% each) and the DE loop was diversified with a combination of Tyr, Ser and Gly. A phage-display library containing ~10" independent clones was constructed.

The library was sorted using a biotinylated peptide target (pY1139 as described above) following the methods described above. After three rounds of library sorting, 8 clones were selected for characterization using phage ELISA and DNA sequencing, which yielded two unique sequences.

The affinity of selected clones was first characterized using competition phage ELISA (34). The experiment revealed that clones eSH2-3 and eSH2-6 had an $IC_{50}$ value of 90 μM, which is an ~800 fold enhancement compared with the parent, Grb2-SH2 (see, FIG. H1 B-E which is a series of graphs of a comparison of binding affinity and specificity of the Grb2-SH2 domain and SH2 clamps as follows: (A) binding of Grb2-SH2 and two SH2 clamps to the ErbB2 peptide (pY1139; black, SEQ ID NO: 78) and the ErbB4 peptide (pY1208; gray, SEQ ID NO: 144) as measured using phage ELISA; the absorbance of ELISA substrate (vertical scale) indicates the level of binding; (B and C) affinities of eSH2-3 (B) and eSH2-6 (C) to pY1139 measured by competition phage ELISA. In this experiment, phages were first incubated with a free peptide of the given concentrations and phages not bound to the peptide were captured and detected by ELISA. The $IC_{50}$ value is the concentration of the free peptide required to cause 50% inhibition. The curves show the best fit of the 1:1 binding model. (D and E) Affinity of Grb2-SH2 to pY1139 (D) and pY1208 (E) measured by competition phage ELISA. Note that the concentration range for (D) and (E) are higher than that for (B) and (C).)

The binding of these clamps to another related peptide corresponding to residues 1204-1216 of ErbB4 receptor (NEPLpYLNTFANTC) (SEQ ID NO: 144) was also characterized using competition phage ELISA (FIG. H1 A). Remarkably, the SH2 clamps showed significantly reduced binding to the ErbB4 peptide with respect to the starting construct (i.e. cpSH2-FN3 fusion), indicating that these SH2 clamps bind much more strongly to the ErbB2 peptide than the ErbB4 peptide. Thus, their binding specificity was significantly enhanced relative to that of the parent SH2 domain.

The two proteins were expressed as free proteins and their binding was further characterized using surface plasmon resonance.

Generation of Additional High-Performance Affinity Clamps for Phospho-Peptide Motifs As noted above, Pin1 WW is a particularly attractive target for the molecular affinity clamp technology, because, as can be inferred from its role in mitotic control (47,48), it binds to many sites that are phosphorylated by the mitogen-activated protein (MAP) kinases (PX(S/T)P). Available data suggests that the Pin1 WW domain also prefers Pro at the (−2) site (44), making it particularly suitable for recognizing MAP kinase sites. A recent ScanSite search (scansite.mit.edu)(49) suggested the presence of at least a few hundred motifs in the human proteome that can be recognized by both MAP kinases and the Pin1 WW domain (data not shown). The binding specificity of Pin1 WW is also similar to the substrate specificity of cyclin-dependent kinases, (S/T)P. Thus, affinity clamps can be generated to a very large number of particularly important motifs in signal transduction and cell-cycle control using the Pin1 WW domain. The broad specificity of Pin1 WW is an advantage, because diverse molecular affinity clamps can be produced with distinct and enhanced specificity.

The WW domain is very small and the C-terminus is closely located to the peptide-binding site, suggesting that the circular permutation need not be performed. Indeed, the architecture of the entire Pin1 protein (FIG. D2A) is such that the WW domain presents the peptide motif to the catalytic domain in a manner very similar to the molecular affinity clamp architecture (44). The elimination of the circular permutation step reduces the upfront effort of setting up the combinatorial library. Extensive characterization of the Pin1 WW domain has established that this domain is well-folded and stable (44, 50).

Phage Display, Library Construction and Sorting

Initial target peptide motifs are chosen among known targets of Pin1 (Table 3). In addition, known MAP kinase targets that have the consensus sequence for Pin1 WW are included. Unlike the recombinant method described above, these phosphopeptides are chemically synthesized using a HTP peptide synthesizer. Peptides are synthesized with a C-terminal Cys residue so that a biotin moiety can be conveniently attached through chemical modification, and also, with a fluorescence dye at the N-terminus for binding assays.

Alternatively, phosphopeptides are made by enzymatic phosphorylation of recombinantly produced peptides. The SUMO fusion approach described above is used for the production of peptides followed by kinase treatment.

For constructing eWW's, Pin1 WW is fused to the N-terminus of FN3 using a linker, such as a 9-residue linker (GGSSSGSSS) (SEQ ID NO: 79), and binding is tested to a target peptide from Cdc25c (VPRpTPV (SEQ ID NO: 80); pT denotes phospho-Thr). The wild-type Pin1 WW has a $K_d$ of 8 μM, which is sufficiently low for detection with phage ELISA. Libraries are then constructed and sorted using target peptide motifs (Table 3), in the same manner as described for ePDZ's except that all procedures are performed in the presence of a phosphatase inhibitor cocktail.

Affinity and Specificity Evaluation Using Protein Arrays

The affinity and specificity of phospho-peptide binding molecular affinity clamps (e.g., eWW's) is determined using the quantitative protein microarray described above. Phage-displayed molecular affinity clamps are reformatted into soluble proteins. Proteins are spotted at a density of 96 spots per well on an aldehyde-modified glass slide and immobilized by chemical cross-linking. The glass is assembled into a microtiter plate with custom-made parts, a bottom-less 96-well microtiter plate (Eric Scientific) and an intervening silicone gasket (Grace Biolabs). To each well, a fluorescence labeled peptide is added and after brief washing, peptide binding is evaluated using an array reader. Binding specificity is evaluated first from the binding profile of molecular affinity clamps to a series of peptides. Molecular affinity clamps exhibiting a good level of specificity are then tested in Western blotting.

Evaluation of Molecular Affinity Clamps in Immunochemical Assays

The generated molecular affinity clamps are evaluated using pull down and Western blot experiments with cell extracts. For facile detection, biotinylated molecular affinity clamps for streptavidin-based detection are prepared. For the eSH2 clamps, cells containing activated and non-activated forms of c-MET and those containing the two forms of ErbB2 are used. For c-MET, the performance of molecular affinity clamps are compared with antibodies from a collaborator. The detection limit and the level of background are compared. For eWW's, cell extracts containing c-Jun, histone H1 or histone H3 are used.

Use of Molecular Affinity Clamps for Affinity Chromatography

The preparation of a chemically and functionally homogenous sample is a fundamental step in biochemical and biophysical characterization of proteins. Among the purification methods available, affinity chromatography is a preferred method due to its high specificity and capacity. Due to their high affinity, high specificity and low dissociation constants, the molecular affinity clamps in accordance with the invention are very well suited for use as immobilized affinity reagents for use in affinity chromatography. Molecular affinity clamps engineered to bind to a target peptide within a protein of interest, e.g. post-translationally modified histones, can be immobilized on a solid substrate and used to purify the protein of interest by affinity chromatography. Additionally, a target peptide for which a molecular affinity clamp is available, e.g. the ARVCF peptide described above, can be fused to a protein of interest using recombinant techniques. This fusion peptide can then be purified by affinity chromatography by virtue of the binding of the target peptide tag to immobilized molecular affinity clamps.

Evaluation of eWW's in CHIP Assays

Because many of eWW's targets are transcription factors and other DNA binding proteins (e.g., histone H1), eWW's using chromatin immunoprecipitation (CHIP) assays are evaluated (61-63). These tests critically evaluate the performance of eWW's in a standard format.

Engineering of Affinity Clamps, eSH2's and eWW's

After establishing the feasibility of the molecular affinity clamp technology to phospho-peptide motifs, additional rounds of engineering to improve affinity and specificity or to alter motif specificity are performed. Procedures used here are equivalent to those employed for PDZ domains.

For WW, motifs corresponding to MAP kinase sites are used, because this class contains so many motifs that are highly relevant to cancer biology, and improving the affinity and specificity of eWW's is advantageous.

For SH2, two complementary approaches are performed. First, amino acid diversity is introduced into the Grb2-SH2 domain in the same manner as for the PDZ domain described above. Second, the entire Grb2-SH2 domain is replaced with another SH2 domain with a distinct mode of binding preference. A good candidate is SHC1-SH2 that binds to pY(I/E/Y/L)X(I/L/M) (SEQ ID NO: 81). Because SH2 domains share a common architecture, the same scheme for circular permutation can be performed without detrimental effects to eSH2's. In this manner, the specificity of an eSH2 can be drastically altered without cycles of library construction and sorting.

The WW and SH2 domains are stable and well behaved, as evidenced by their popularity in sample intensive biophysical studies. An advantage of phage display is the ability to select clones with the desired phenotype among ten billion variants. Therefore, even in the unlikely event that perturbations to these domains significantly reduce their function, such impacts are minimized by selecting variants with improved function. Stability studies of beta-sheet proteins and stabilization of proteins (64-68) can be exploited to rationally design stabilizing mutations of WW and SH2 proteins.

If a long linker, as used in the initial eWW design, limits the level of affinity enhancement achievable with the molecular affinity clamp strategy, a disulfide cross-link can be introduced between a position within the linker near the FN3 domain and a position in the WW domain near the molecular affinity-binding site (e.g., Ser19). As neither Pin1 WW nor FN3 contains a Cys, a unique disulfide can be introduced in a molecular affinity clamp. It is well established that a disulfide bond is consistently formed between two Cys residues in a phage-displayed protein (34). If necessary, the linker sequence can be optimized by combinatorial selection to maximize the eWW performance. The effectiveness of such a disulfide-mediated tether has been demonstrated for a PDZ-based affinity clamp (FIG. E3).

Generation of Additional High-Performance Affinity Clamps for Histones

Histones are the major protein component of chromatin, and many types of post-translational modifications (PTMs) of the flexible "tails" of histones are now known. These histone PTMs are viewed as "histone codes" that play essential roles in conveying epigenetic information. Therefore, identifying the types and locations of histone PTMs is central to epigenetics research. Among histone PTMs, detecting methylation of Lys residues in histone H3 is of particular interest, although other types of histone PTMs can be detected with this technology as well.

The chromatin organization modifier domain, or chromodomain, was first identified in Drosophila HP1, and it was found to bind to H3K9Me3 ($K_d$=2.5 μM) and H3K9Me2 ($K_d$=7 μM). It has an SH3 domain-like (3-barrel, and it binds to these histone marks using a shallow surface groove, a common mode of interaction found in many interaction domains. The chromodomain of the Drosophila Polycomb protein also binds to H3K27Me3. The chromodomain belongs to the so-called Royal superfamily that includes "double chromodomian" that binds to H3K4me. Thus, as a family, chromodomains can bind to a variety of methylated Lys sites. The plant homeodomain (PHD) domains (also called PHD fingers) are small zinc-stabilized domains and found in proteins involved in transcription activation. The PHD domain of the BPTF subunit of the ATP-dependent chromatin-remodeling complex, NURF, binds to H3K4Me3 ($K_d$=2.7 μM) and H3K4Me2 ($K_d$=5 μM). Importantly, the BPTF PHD domain has been engineered to have a distinct binding preference favoring H3K4Me2 to H3K4Me3, demonstrating the ability to alter binding specificity by mutations within a PHD domain. FN3-based synthetic binding proteins may be used as the enhancer with these domains to form affinity clamps that bind modified or unmodified histones with high affinity and specificity.

Based on the crystal structure, a codon-optimized gene for the structured core of the chromodomain was synthesized. The structural integrity of the chromodomain from this construct has been confirmed by NMR spectroscopy. The HSQC spectrum is well-dispersed, characteristic of a well-folded protein. A peptide corresponding to the H3K9Me3 site was also synthesized. Addition of a peptide corresponding to the H3K9Me3 site caused a large spectral change, indicating peptide binding. Having confirmed the function of the chromodomain construct, a phage-display vector for the chromodomain was constructed in the manner described above. The chromodomain was displayed at a level comparable to that for the FN3 domain. Vectors for the Polycomb chromodomain that are homologous to the HP1 chromodomain but preferentially bind to the H3K27Me3 site over H3K9Me3 can also be constructed. The chromodomains of HP1 and Polycomb and the PHD domain of BPTF may be used. For brevity, these domains will be referred to simply as the Chromo and PHD domains, respectively, hereafter. Both of these domains have been extensively characterized and they bind to $Me_x$%-containing histone H3 segments with a single μM $K_d$.

The functional Chromo domain construct can be displayed on the phage surface. Because the N-terminus of the Chromo domain is located in a close proximity to the peptide-binding site, circular permutation must be used. The gene for the PHD domain can be constructed and its function can be tested in the same manner as for the Chromo domain. High-quality affinity clamps that bind histones can be generated to the cognate targets of the Chromo and PHD domains, i.e. H3K9Me3 and H3K4Me3, respectively. These can be targeted to different methylation forms of the same segment, e.g. H3K4Me1 and H3K4Me2. Because the methylated Lys side chain binds to the so-called aromatic cage in either domain and it is still quite exposed, one can engineer the enhancer (FN3) domain that can discriminate the unmodified, Me1, Me2 and Me3 forms with high specificity.

Because the N-terminus of these histone-binding proteins are located in a close proximity to the peptide binding site, they can be connected to the C-terminus of the FN3 enhancer domain to the N-terminus of the Chromo or PHD domain. This arrangement, which is opposite to the PDZ-based affinity clamps above, results in the "bottom" side of the FN3 scaffold facing the binding site. Therefore, three loops located on the bottom side, AB, CD and EF should be used as the recognition loops for constructing a binding interface.

Amino acid diversity can be introduced in the FN3 loops to construct a combinatorial library. Latest-generation amino acid compositions can be used for these positions, having been developed from the inventors' large-scale selection of synthetic antibodies to diverse targets. Mutagenic oligonucleotides can be synthesized using a trimer nucleotide mixture with the designed composition available from Glen Research. Libraries can be constructed using the high-efficiency Kunkel mutagenesis method that reliably produces ~$10^{10}$ independent members.

A synthetic peptide encompassing −7 to +7 positions from the methylated Lys of interest (i.e. a 15-residue segment) can be used as a target for selection. Because the Chromo and PHD domains recognize a 5-7 residue segment containing a histone mark, a 15-residue segment is sufficiently long for representing the actual histone tail. A four-residue tag, GYCD (SEQ ID NO: 82) —COOH(COOH represents the free carboxyl terminus) is added to the C-terminus of a sequence of interest so that one can accurately determine the peptide concentration using Tyr absorbance and easily conjugate chemical groups (e.g. biotin and fluorescent dye) through Cys. Gly and Asp residues are included to minimize the effect of the tag (Gly) and prevent aggregation of the peptide (Asp). Thus, for example, a target peptide for the H3K9 site is:

NH2-ARTKQTAR(K*)STGGKAPGYCD-COOH where K* represents a methylated Lys.

HTP peptide synthesis is performed using a Symphony 12 channel peptide synthesizer (Protein Technologies). Peptides are synthesized in N,N-dimethylformamide (DMF) on the solid phase at a 50 µmol scale using standard Fmoc chemistry. All amino acids are coupled twice at 5-fold molar excess. In most cases, amino acids are activated in situ with 0.95 equivalents of 2-(1H-benzotriazole-1-yl)-1,1,3,3-tetramethyluronium hexafluorophosphate (HBTU) and 2 equivalents of N,N-diisopropylethylamine (DIPEA) and coupled for 1 h at room temperature. CLEAR®, polyethylene glycol supported resin (0.8 mmol/g) charged with the first amino acid is employed for most peptides but low substitution resin is employed when large (>20 amino acid) peptides are synthesized to minimize aggregation and premature synthesis termination. Following their synthesis but before their deprotection and cleavage, peptides can be labeled with many different tags (e.g. biotin) or dyes by standard amino acid coupling procedures. Peptides are cleaved from the resin using Reagent K [82.5% TFA (v/v), 5% phenol (v/v), 5% water (v/v), 5% thioanisole (v/v), 2.5% 1,2-ethanedithiol (v/v)] and precipitated in cold diethylether.

Peptides are purified by automated analytical-to-preparative mass directed fraction collection-based high performance liquid chromatography (HPLC). This instrument contains an Agilent 1200 series quaternary pump flowing into an Agilent 6140 single quadrupole mass spectrometer. Following analytical-scale analysis, the appropriate preparative gradient program is selected by the instrument along with the pre-selected target mass and the instrument then collects fractions that contain the appropriate mass/charge ratio. A portion of a given peptide can be modified with a biotinylation reagent (Biotin-HPDP; Pierce) or with a fluorescent dye (Alexa 488 or similar) through the single Cys residue.

To generate affinity clamps that bind histones, sorting of combinatorial libraries using a biotinylated peptide can be performed. The inventors have developed semi-automated and highly streamlined protocols for phage display library screening employing a magnetic beads-handling robot ("KingFisher", Thermo Corporation). With this robot that moves magnetic beads between the wells of a 96-well plate, 12 selection reactions can be performed in parallel.

In typical sorting, a biotinylated target is incubated with a phage-display library in solution, and library members bound to the target are captured using streptavidin magnetic beads. When sorting the final, highly enriched library, the stringency is increased using the "off-rate" selection. In this method, after a phage library is allowed to bind to a biotinylated target, an excess amount of a non-biotinylated target is added as a competitor so that rebinding of the biotinylated target is prevented. This sorting scheme primarily selects variants with a slow off-rate, which is an excellent indicator of high affinity. Typically, three to four rounds of sorting is performed, which takes only one week with our automated procedures.

Successful selection is confirmed with two parameters. "Enrichment ratio" is the number of phages recovered from selection with a target over that from control selection without the target. "Hit rate" is the number of target-binding clones in a randomly picked sample of clones, typically eight. When an enrichment ratio of 20 or greater is obtained, ≥50% of clones have desired binding properties. The inventors have established automated procedures for this assay using a liquid-handling robot (Biomek 2000, Beckman). An additional round of sorting may be performed if further enrichment of functional clones is desired.

Selected clones are reformatted into free proteins with a His$_8$-tag. This is achieved conveniently by introducing His$_8$ and the Amber stop codon between the affinity clamp gene and the phage p3 gene. In this manner, we can produce a soluble protein in a non-suppressor strain (e.g. DH5a) and also phage particles in a suppressor strain (e.g. XL1-Blue), thus giving us a high level of flexibility. Proteins are expressed in a small scale using a deep 96-well plate and purified with Ni-affinity magnetic beads (Novagen) in an automated manner using a Kingfisher instrument.

The affinity of the affinity clamps can be determined using fluorescence polarization (FP) assays. Briefly, the FP of a fluorescence-labeled target peptide can be determined in the presence of different amounts of a purified affinity clamp protein. These assays are performed in 96- or 384-well format using a liquid handler and a fluorescent plate reader (Tecan Safire 2), and they are naturally high-throughput. When binding kinetics data (in particular the off rate) are needed, SPR assays can be performed by immobilizing a biotinylated target peptide on a streptavidin surface. HTP procedures have been implemented that measure 64 samples overnight using a Biacore 2000 instrument. $K_d$ values from sub-nM to ~20 µM can be determined using current SPR methods, which is sufficient for the targeted affinity for the affinity clamps (single-digit nM). Binding specificity of affinity clamps that exhibit high-affinity ($K_d$<100 nM) can then be characterized. A panel of peptide targets can be used that differs in either amino acid sequence or methylation state from the target of interest. Affinity can be determined using FP and/or SPR assays.

If the initial library sorting does not yield affinity clamps with sufficiently high levels of affinity and specificity towards the target histone, affinity maturation can be performed. Here, additional sequence diversity is introduced in the FN3 loops of initially obtained affinity clamps to construct a second-generation library. Such a library is sorted under more stringent conditions (e.g. lower target concentrations and longer washing period). Because FN3 sequence diversity is restricted in three loops, sequence optimization can be focused on these loops. Each loop is first individually optimized by phage display. After these initial sorting steps that enrich functional sequences in individual loops, the selected loop sequences can then combined (or "shuffled") to make the final library. This strategy ensures that a large number of sequences can be sampled while maintaining the binding mode of the starting clones.

To engineer high specificity, library selection can be performed in the presence of excess competitors, i.e. peptides with slightly different sequences and/or methylation states from the real target. For example, to obtain affinity clamps with high specificity toward H3K9Me3 with the HP1 Chromo domain, which discriminates Met and Me3 states of H3K9 only by less than 2 fold, a library can be sorted with biotinylated H3K9Me3 as the target and nonbiotinylated H3K9Me2 as a competitor.

The length and sequence of the linker between the two biorecognition domains, e.g. the Chromo/PHD and FN3 portions, can also be optimized. Library construction and screening can be performed in the same manner as described above. Once the optimum linker is identified, it can be introduced into the initial library to improve the probability of obtaining highly functional affinity clamps from the initial library.

Affinity clamp proteins produced for initial binding characterization as described above are designed to be monomeric. Because antibodies (IgG's) have the "Y" shape containing two antigen-binding fragments (Fab) per molecule, the avidity effect, i.e. the ability to form multivalent interactions, can significantly enhance the apparent binding affinity of an IgG. To make a fair comparison, the affinity clamps that are selected for these tests can be reformatted into a dimeric format. This can be easily done by making a glutathione-S-transferase (GST) fusion protein of an affinity clamp. GST is a dimeric and highly stable protein that is widely used as a fusion partner. Affinity clamp-GST fusion proteins can be expressed in the cytoplasm of E. coli. A His$_{10}$ tag and a free Cys residue can be attached for efficient purification and derivatization. Alternatively, an Fc (the IgG constant fragment) fusion of affinity clamps can also be made so that the identical protocols can be used for antibodies and affinity clamps. It is noted that protein A and protein G, commonly used in ChIP assays, bind tightly to the Fc portion of IgG.

Thermal unfolding properties of affinity clamps can be determined using circular dichroism spectroscopy. In this experiment, circular dichroism spectra are recorded as the sample temperature is slowly raised until a cooperative unfolding is observed. It is likely that the interaction domain used in the construction of affinity clamps, e.g., Chromo or PHD domain, will unfold at a lower temperature than the FN3 domain because FN3 is highly thermostable (the stabilized form of FN3 used herein has a melting mid-point of ~95° C.). The "heat inactivation" profile can also be determined by incubating an affinity clamp at 50° C. for variable duration and then determining the residual activity. For affinity clamps that bind to histones, HeLa cell extracts and MCF-7 cell extracts can be used as standard samples for Western as well as ChIP experiments. Histone tails can be detected with affinity clamps labeled with IRDye (LI-COR Biosciences) or monoclonal antibodies (and a secondary antibody labeled with IRDye) and quantified with a LI-COR Odyssay Infrared Imaging system. Western blotting with varied amounts of cell extracts can determine the sensitivity of affinity clamps as compared to monoclonal antibodies.

Because affinity clamps can be directly labeled with the dye, a secondary detection reagent may not be required. This decreases the experiment time and reagent costs. It is possible that the detection sensitivity may be decreased due to the absence of the signal amplification step by the secondary antibody. Thus, multiple formats of affinity clamps (e.g. directly labeled with the dye, biotinylation followed by dye-labeled streptavidin and Fc fusion followed by dye-labeled secondary antibody) can be tested to obtain the best sensitivity per costs and time.

Mutations can also be introduced in the interaction domain (e.g. Chromo and PHD) that alters the underlying specificity of affinity clamps. Alteration of specificity is relatively straightforward. The Chromo domains from HP1 and Polycomb have 54% sequence identity and very similar three-dimensional structures, but HP1 Chromo preferentially binds to the H3K9Me3 (QTARK*ST (SEQ ID NO: 83); K* denotes a methylated Lys) and Polycomb binds to the H3K27Me3 (KAARK*SA) (SEQ ID NO: 84). These results demonstrate that subtle sequence differences of Chromo domain can alter the sequence specificity. Likewise, the "aromatic cage" of the BPTF PHD domain has been engineered to have a reversed binding preference favoring H3K4Me2 to H3K4Me3, demonstrating the ability to alter binding specificity toward methylation states by mutations within a PHD domain. The aromatic cage motif is also present in the methyl-Lys binding site of the Chromo domain, and thus a similar mutation can be used to alter the methylation preference of the Chromo domain. Previously described directed evolution approaches can be applied to systematically identify specificity-altering mutations.

Other Enhancer Domains

A disulfide-constrained peptide was used as an enhancer domain. A peptide-PDZ affinity clamp was designed in which the diversified peptide segment was N-terminal connected to the circularly permutated PDZ domain (cpPDZ) described above. (See, FIG. F1 showing an affinity clamp constructed with Cys-constrained peptide as an enhancer domain in which (A) is a schematic drawing of the affinity clamp. Note that the peptide is attached to the N-terminus of the interaction domain. (B, C) are saturation curves of the parent PDZ (B) and peptide-PDZ Affinity Clamp (C) determined using surface plasmon resonance (SPR). SPR experiments were performed in the equilibrium mode, and the SPR response is plotted as a function of the concentration of the target peptide. The target peptide fused to the yeast SUMO protein was used in these measurements. The curves show the best fit of the 1:1 binding model to the data. The K$_d$ values are also shown.)

As noted, the construct is schematically drawn in FIG. F1, panel A. A combinatorial phage display library of peptide-PDZ affinity clamps was constructed. The phage display library was sorted in a similar manner to the PDZ-FN3 affinity clamps described above. By sequencing the enriched phage clones, two unique clones exhibited higher binding as tested using phage ELISA. The two unique clones had sequences of their peptide segment as:

Clone 282-1: SNCRHNTGYNSCSR
Clone 282-6: NFCASNGTGNDCRR

Clone 282-6 was transferred to an expression vector pHFT2 (30), a derivative of pHFT1 (69) in which the His$_6$ tag had been replaced with a His$_{10}$ tag. The peptide-PDZ affinity clamps were expressed and purified in the same manner as PDZ-FN3 affinity clamps. The peptide-PDZ affinity clamp was monomeric as measured with size-exclusion chromatography (Superdex 75; Amersham Biosciences).

Using surface plasmon resonance, the dissociation constant ($K_d$) of the peptide-PDZ affinity clamp, clone 282-6, and the ARVCF peptide was determined to be 0.91±0.12 μM (FIG. F1 panel C). The circularly permutated PDZ domain (i.e. the parent interaction domain) had the $K_d$ of 11.0±0.7 μM (FIG. F1 panel B). Thus, the peptide-PDZ affinity clamp has 12-fold higher affinity than the parent interaction domain. It is very likely that the affinity of this peptide-PDZ affinity clamp can be further increased by iterative affinity maturation processes in which a subset of positions within the peptide segment is diversified and clones with higher affinity are selected. (See, also, FIG. G1 which shows sequences of peptide-PDZ affinity clamps. Residues 1-20 correspond to a secretion signal sequence. Residues shown are the peptide sequences selected from the combinatorial library and the C-terminal His8 tag for purification.)

Other Interaction Domains

Molecular affinity clamps can be developed using other interaction domains (5). Candidate domains (and their respective binding motifs) include PTB (phospho-Tyr), (pY), FHA (phospho-Thr), Bromo (acetylated Lys), Chromo (methylated Lys) and SH3 (Pro-rich) (5). A more extensive list of candidate domains has been provided hereinabove. These interaction domains meet the topological requirement for engineering molecular affinity clamps, and thus the "plug-and-play" nature of the molecular affinity clamp technology will enable application of the same procedures described herein.

In summary, the invention embodies a bifunctional modular molecular architecture in the form of a molecular affinity clamp. A first biorecognition module of the clamp generally contains a naturally occurring binding domain for a target motif. The second biorecognition module of the clamp contains the enhancer domain which is an engineered polypeptide with enhanced affinity and specificity for the target motif as selected from a combinational library of candidate polypeptides. The two modules may be directly linked, e.g., through a naturally occurring tail of one of the modules, or indirectly via a linker moiety. Affinity clamps embodying the principles of the invention are, in effect, heterodimers of different monomers or subunits, each of which has a binding site for the target motif of interest, and each of which is capable of binding the target motif at distinct sites. The affinity clamps in accordance with the invention are thus unispecific, bivalent heterodimers, i.e., constructs that have two binding sites, one on each monomer or subunit of different structure, which can simultaneously bind the target motif.

While the invention has now been described and exemplified with some specificity, those skilled in the art will appreciate the various modifications, including variations, additions, and omissions that may be made in what has been described. Accordingly, it is intended that these modifications also be encompassed by the present invention and that the scope of the present invention be limited solely by the broadest interpretation that lawfully can be accorded the appended claims.

All patents, publications and references cited herein are hereby fully incorporated by reference. In case of conflict between the present disclosure and incorporated patents, publications and references, the present disclosure should control.

REFERENCES

1. Jones R B, Gordus A, Krall J A & MacBeath G. (2006). A quantitative protein interaction network for the ErbB receptors using protein microarrays. *Nature* 439, 168-74.
2. Haab B B, Paulovich A G, Anderson N L, Clark A M, Downing G J, Hermjakob H, Labaer J & Uhlen M. (2006). A reagent resource to identify proteins and peptides of interest for the cancer community: a workshop report. *Mol Cell Proteomics* 5, 1996-2007.
3. Rimmele M. (2003). Nucleic acid aptamers as tools and drugs: recent developments. *Chembiochem* 4, 963-71.
4. Yan A C, Bell K M, Breeden M M & Ellington A D. (2005). Aptamers: prospects in therapeutics and biomedicine. *Front Biosci* 10, 1802-27.
5. Pawson T & Nash P. (2003). Assembly of cell regulatory systems through protein interaction domains. *Science* 300, 445-52.
6. Blagoev B, Kratchmarova I, Ong S E, Nielsen M, Foster L J & Mann M. (2003). A proteomics strategy to elucidate functional protein-protein interactions applied to EGF signaling. *Nat Biotechnol* 21, 315-8.
7. Lo Conte L, Chothia C & Janin J. (1999). The atomic structure of protein-protein recognition sites. *J Mol Biol* 285, 2177-98.
8. Skerra A. (2000). Engineered protein scaffolds for molecular recognition. *J Mol Recognit* 13, 167-87.
9. Binz H K, Amstutz P & Pluckthun A. (2005). Engineering novel binding proteins from nonimmunoglobulin domains. *Nat Biotechnol* 23, 1257-68.
10. Binz H K & Pluckthun A. (2005). Engineered proteins as specific binding reagents. *Curr Opin Biotechnol* 16, 459-69.
11. Hosse R J, Rothe A & Power B E. (2006). A new generation of protein display scaffolds for molecular recognition. *Protein Sci* 15, 14-27.
12. Bork P & Doolittle R F. (1992). Proposed acquisition of an animal protein domain by bacteria. *Proc. Natl. Acad. Sci. USA* 89, 8990-8994.
13. Koide A, Bailey C W, Huang X & Koide S. (1998). The fibronectin type III domain as a scaffold for novel binding proteins. *J. Mol. Biol.* 284, 1141-1151.
14. Xu L, Aha P, Gu K, Kuimelis R, Kurz M, Lam T, Lim A, Liu H, Lohse P, Sun L, Weng S, Wagner R & Lipovsek D. (2002). Directed evolution of high-affinity antibody mimics using mRNA display. *Chem Biol* 9, 933-42.
15. Karatan E, Merguerian M, Han Z, Scholle M D, Koide S & Kay B K. (2004). Molecular recognition properties of FN3 monobodies that bind the Src SH3 domain. *Chem Biol* 11, 835-44.
16. Dickinson C D, Veerapandian B, Dai X-P, Hamlin R C, Xuong N-H, Ruoslahti E & Ely K R. (1994). Crystal structure of the tenth type III cell adhesion module of human fibronectin. *J. Mol. Biol.* 236, 1079-1092.
17. Main A L, Harvey T S, Baron M, Boyd J & Campbell I D. (1992). The three-dimensional structure of the tenth type III module of fibronectin: an insight into RGD-mediated interactions. *Cell* 71, 671-678.
18. Carr P A, Erickson H P & Palmer AGr. (1997). Backbone dynamics of homologous fibronectin type III cell adhesion domains from fibronectin and tenascin. *Structure* 5, 949-959.
19. Plaxco K W, Spitzfaden C, Campbell I D & Dobson C M. (1997). A comparison of the folding kinetics and thermodynamics of two homologous fibronectin type III modules. *J. Mol. Biol.* 270, 763-770.
20. Plaxco K W, Spitzfaden C, Campbell I D & Dobson C M. (1996). Rapid refolding of a proline-rich all-beta-sheet fibronectin type III module. *Proc. Natl. Acad. Sci. USA* 93, 10703-10706.
21. Martinez J C, Viguera A R, Berisio R, Wilmanns M, Mateo P L, Filimonov V V & Serrano L. (1999). Thermodynamic analysis of alpha-spectrin SH3 and two of its circular permutants with different loop lengths: discerning the reasons for rapid folding in proteins. *Biochemistry* 38, 549-59.
22. Nourry C, Grant S G & Borg J P. (2003). PDZ domain proteins: plug and play! *Sci STKE* 2003, RE7.
23. Birrane G, Chung J & Ladias J A. (2003). Novel mode of ligand recognition by the Erbin PDZ domain. *J Biol Chem* 278, 1399-402.
24. Skelton N J, Koehler M F, Zobel K, Wong W L, Yeh S, Pisabarro M T, Yin J P, Lasky L A & Sidhu S S. (2003). Origins of PDZ domain ligand specificity. Structure determination and mutagenesis of the Erbin PDZ domain. *J Biol Chem* 278, 7645-54.
25. Laura R P, Witt A S, Held H A, Gerstner R, Deshayes K, Koehler M F, Kosik K S, Sidhu S S & Lasky L A. (2002). The Erbin PDZ domain binds with high affinity and specificity to the carboxyl termini of delta-catenin and ARVCF. *J Biol Chem* 277, 12906-14.
26. Malakhov M P, Mattern M R, Malakhova O A, Drinker M, Weeks S D & Butt T R. (2004). SUMO fusions and SUMO-specific protease for efficient expression and purification of proteins. *J Struct Funct Genomics* 5, 75-86.
27. Ferrer M, Maiolo J, Kratz P, Jackowski J, Murphy D, Delagrave S & Inglese J. (2005). Directed evolution of PDZ variants to generate high-affinity detection reagents. *Protein Eng Des Sel* 18, 165-73.
28. Fellouse F A, Li B, Compaan D M, Peden A A, Hymowitz S G & Sidhu S S. (2005). Molecular recognition by a binary code. *J Mol Biol* 348, 1153-62.
29. Fellouse F A, Wiesmann C & Sidhu S S. (2004). Synthetic antibodies from a four-amino-acid code: a dominant role for tyrosine in antigen recognition. *Proc Natl Acad Sci USA* 101, 12467-72.
30. Koide A, Gilbreth R N, Esaki K, Tereshko V & Koide S. (2007). High-affinity single-domain binding proteins with a binary-code interface. *Proc Natl Acad Sci USA* 104, 6632-7.
31. Steiner D, Forrer P, Stumpp M T & Pluckthun A. (2006). Signal sequences directing cotranslational translocation expand the range of proteins amenable to phage display. *Nat Biotechnol* 24, 823-31.
32. Koide A & Koide S. (2007). Monobodies: antibody mimics based on the scaffold of the fibronectin type III domain. *Methods Mol Biol* 352, 95-109.
33. Kunkel T A, Roberts J D & Zakour R A. (1987). Rapid and efficient site-directed mutagenesis without phenotypic selection. *Methods Enzymol.* 154, 367-382.
34. Sidhu S S, Lowman H B, Cunningham B C & Wells J A. (2000). Phage display for selection of novel binding peptides. *Methods Enzymol* 328, 333-63.
35. Fuh G, Pisabarro M T, Li Y, Quan C, Lasky L A & Sidhu S S. (2000). Analysis of PDZ domain-ligand interactions using carboxyl-terminal phage display. *J Biol Chem* 275, 21486-91.
36. Wiedemann U, Boisguerin P, Leben R, Leitner D, Krause G, Moelling K, Volkmer-Engert R & Oschkinat H. (2004). Quantification of PDZ domain specificity, prediction of ligand affinity and rational design of super-binding peptides. *J Mol Biol* 343, 703-18.
37. Appleton B A, Zhang Y, Wu P, Yin J P, Hunziker W, Skelton N J, Sidhu S S & Wiesmann C. (2006). Comparative structural analysis of the Erbin PDZ domain and the first PDZ domain of ZO-1. Insights into determinants of PDZ domain specificity. *J Biol Chem* 281, 22312-20.
38. Reina J, Lacroix E, Hobson S D, Fernandez-Ballester G, Rybin V, Schwab M S, Serrano L & Gonzalez C. (2002). Computer-aided design of a PDZ domain to recognize new target sequences. *Nat Struct Biol* 9, 621-7.
39. Boder E T, Midelfort K S & Wittrup K D. (2000). Directed evolution of antibody fragments with monovalent femtomolar antigen-binding affinity. *Proc Natl Acad Sci USA* 97, 10701-5.
40. Boder E T & Wittrup K D. (1997). Yeast surface display for screening combinatorial polypeptide libraries. *Nat Biotechnol* 15, 553-7.
41. Schlessinger J & Lemmon M A. (2003). SH2 and PTB domains in tyrosine kinase signaling. *Sci STKE* 2003, RE12.
42. Yaffe M B & Smerdon S J. (2001). PhosphoSerine/threonine binding domains: you can't pSERious? *Structure* 9, R33-8.
43. Lu P J, Zhou X Z, Shen M & Lu K P. (1999). Function of WW domains as phosphoserine- or phosphothreonine-binding modules. *Science* 283, 1325-8.
44. Verdecia M A, Bowman M E, Lu K P, Hunter T & Noel J P. (2000). Structural basis for phosphoserine-proline recognition by group IV WW domains. *Nat Struct Biol* 7, 639-43.
45. Rahuel J, Gay B, Erdmann D, Strauss A, Garcia-Echeverria C, Furet P, Caravatti G, Fretz H, Schoepfer J & Grutter M G. (1996). Structural basis for specificity of Grb2-SH2 revealed by a novel ligand binding mode. *Nat Struct Biol* 3, 586-9.
46. Nioche P, Liu W Q, Broutin I, Charbonnier F, Latreille M T, Vidal M, Roques B, Garbay C & Ducruix A. (2002). Crystal structures of the SH2 domain of Grb2: highlight on the binding of a new high-affinity inhibitor. *J Mol Biol* 315, 1167-77.
47. Rippmann J F, Hobbie S, Daiber C, Guilliard B, Bauer M, Birk J, Nar H, Garin-Chesa P, Rettig W J & Schnapp A. (2000). Phosphorylation-dependent proline isomerization catalyzed by Pin1 is essential for tumor cell survival and entry into mitosis. *Cell Growth Differ* 11, 409-16.
48. Shen M, Stukenberg P T, Kirschner M W & Lu K P. (1998). The essential mitotic peptidyl-prolyl isomerase Pin1 binds and regulates mitosis-specific phosphoproteins. *Genes Dev* 12, 706-20.
49. Yaffe M B, Leparc G G, Lai J, Obata T, Volinia S & Cantley L C. (2001). A motif-based profile scanning approach for genome-wide prediction of signaling pathways. *Nat Biotechnol* 19, 348-53.
50. Wintjens R, Wieruszeski J M, Drobecq H, Rousselot-Pailley P, Buee L, Lippens G & Landrieu I. (2001). $^1$H NMR study on the binding of Pin1 Trp-Trp domain with phosphothreonine peptides. *J Biol Chem* 276, 25150-6.
51. Songyang Z & Cantley L C. (1995). Recognition and specificity in protein tyrosine kinase-mediated signalling. *Trends Biochem Sci* 20, 470-5.
52. Songyang Z, Shoelson S E, Chaudhuri M, Gish G, T. P & al. e. (1993). SH2 Domains Recognize Specific Phosphopeptide Sequences. *Cell* 72, 767 ff.
53. Kessels H W, Ward A C & Schumacher T N. (2002). Specificity and affinity motifs for Grb2-SH2-ligand interactions. *Proc Natl Acad Sci USA* 99, 8524-9.
54. Hynes N E & Lane H A. (2005). ERBB receptors and cancer: the complexity of targeted inhibitors. *Nat Rev Cancer* 5, 341-54.
55. Olayioye M A, Neve R M, Lane H A & Hynes N E. (2000). The ErbB signaling network: receptor heterodimerization in development and cancer. *Embo J* 19, 3159-67.

56. Puri N, Ahmed S, Janamanchi V, Tretiakova M, Zumba O, Krausz T, Jagadeeswaran R & Salgia R. (2007). c-Met is a potentially new therapeutic target for treatment of human melanoma. *Clin Cancer Res* 13, 2246-53.
57. Sawada K, Radjabi A R, Shinomiya N, Kistner E, Kenny H, Becker A R, Turkyilmaz M A, Salgia R, Yamada S D, Vande Woude G F, Tretiakova M S & Lengyel E. (2007). c-Met overexpression is a prognostic factor in ovarian cancer and an effective target for inhibition of peritoneal dissemination and invasion. *Cancer Res* 67, 1670-9.
58. Sattler M & Salgia R. (2007). c-Met and hepatocyte growth factor: potential as novel targets in cancer therapy. *Curr Oncol Rep* 9, 102-8.
59. Christensen J G, Burrows J & Salgia R. (2005). c-Met as a target for human cancer and characterization of inhibitors for therapeutic intervention. *Cancer Lett* 225, 1-26.
60. Ma P C, Maulik G, Christensen J & Salgia R. (2003). c-Met: structure, functions and potential for therapeutic inhibition. *Cancer Metastasis Rev* 22, 309-25.
61. Halasz G, van Batenburg M F, Perusse J, Hua S, Lu X J, White K P & Bussemaker H J. (2006). Detecting transcriptionally active regions using genomic tiling arrays. *Genome Biol* 7, R59.
62. Gilad Y, Oshlack A, Smyth G K, Speed T P & White K P. (2006). Expression profiling in primates reveals a rapid evolution of human transcription factors. *Nature* 440, 242-5.
63. Stolc V, Gauhar Z, Mason C, Halasz G, van Batenburg M F, Rifkin S A, Hua S, Herreman T, Tongprasit W, Barbano P E, Bussemaker H J & White K P. (2004). A gene expression map for the euchromatic genome of *Drosophila melanogaster*. *Science* 306, 655-60.
64. Koide S, Huang X, Link K, Koide A, Bu Z & Engelman D M. (2000). Design of single-layer beta-sheets without a hydrophobic core. *Nature* 403, 456-460.
65. Koide A, Jordan M R, Horner S R, Batori V & Koide S. (2001). Stabilization of a fibronectin type III domain by the removal of unfavorable electrostatic interactions on the protein surface. *Biochemistry* 40, 10326-33.
66. Yan S, Kennedy S & Koide S. (2002). Thermodynamic and Kinetic Exploration of the Energy Landscape of *Borrelia burgdorferi* OspA by Native-state Hydrogen Exchange. *J Mol Biol* 323, 363-75.
67. Koide S, Yang X, Huang X, Dunn J J & Luft B J. (2005). Structure-based design of a second-generation Lyme disease vaccine based on a C-terminal fragment of *Borrelia burgdorferi* OspA. *J Mol Biol* 350, 290-9.
68. Yan S, Gawlak G, Makabe K, Tereshko V, Koide A & Koide S. (2007). Hydrophobic Surface Burial Is the Major Stability Determinant of a Flat, Single-layer beta-Sheet. *J Mol Biol* 368, 230-43.
69. Huang J, Koide A, Makabe K and Koide S. (2008). Design of protein function leaps by directed domain interface evolution. *Proc Natl Acad Sci USA* 105:6578-83.

TABLE 1

FN3 Loop sequences of ePDZ selected for ARVCF

|  | BC loop | DE loop | FG loop |
|---|---|---|---|
| template | ASSSSVS (SEQ ID NO: 85) | PGSKST (SEQ ID NO: 86) | ASSSSSSSSSSSKP (SEQ ID NO: 87) |
| library | AX$^{4-8}$VX (SEQ ID NO: 88) | P(YSG)$^3$T (SEQ ID NO: 89) | AXb-14SP (SEQ ID NO: 90) |

TABLE 1-continued

FN3 Loop sequences of ePDZ selected for ARVCF

|  | BC loop | DE loop | FG loop |
|---|---|---|---|
| ePDZ-a | ASYYGVS (SEQ ID NO: 91) | PYSSST (SEQ ID NO: 92) | AYSDYYGSHHYSP (SEQ ID NO: 93) |
| ePDZ-b | AYYDSHVS (SEQ ID NO: 94) | PGSKST (SEQ ID NO: 95) | AHYNYHYYSSP (SEQ ID NO: 96) |

X = Y, 40%; S, 20%; G, 10%; R, L, H, D, N and A, 5% each

TABLE 2

$K_d$ of ePDZ's and the parent proteins

| Protein name Sequence | ARVCF PQPVDSWV (SEQ ID NO: 97) | δ-catenin PASPDSWV (SEQ ID NO: 98) |
|---|---|---|
| starting material |  |  |
| wt-PDZ | ~10 µM | ~10 µM |
| cp-PDZ-FN3 | 25 (±14) µM | n.d. |
| engineered binder |  |  |
| ePDZ-a | 56 (±5) nM | 430 nM |
| ePDZ-b | 56 (±6) nM | >10 µM | n.d.: not determined

TABLE 3

Phospho-peptide motifs

| Protein source | Sequence | Affinity if known |
|---|---|---|
| For eWW |  |  |
| Cdc25c-T48 | VPRpTPV (SEQ ID NO: 80) | 8 µM |
| Myt1-T412 | PPApTPP (SEQ ID NO: 100) | 15 µM |
| PolII-CTD-S5 | YSPTpSPS (SEQ ID NO: 101) | 34 µM |
| Histone H1.4-S186 | KAPKpSPA (SEQ ID NO: 102) | n.d. |
| c-myc-S62 | TPPLpSPSR (SEQ ID NO: 103) | n.d. |
| c-Jun-S244 | TPPLpSPID (SEQ ID NO: 104) | n.d. |
| myelin basic protein-T99 | VTPRpTPPP (SEQ ID NO: 105) | n.d. |
| Elk-1-S389 | IAPRpSPAK (SEQ ID NO: 106) | n.d. |
| SAP-1-S420 | DGPSpTPGP (SEQ ID NO: 107) | n.d. |
| ErbB1-T693 | VEPLpTPSG (SEQ ID NO: 108) | n.d. |

TABLE 3-continued

Phospho-peptide motifs

| Protein source | Sequence | Affinity if known |
|---|---|---|
| VEGFR-2-S1197 | SLPTpSPVS (SEQ ID NO: 109) | n.d. |
| Estrogen Receptor α S118 | PPQLpSPFL (SEQ ID NO: 110) | n.d. |
| Cdc25c-S214 | LYRpSPS (SEQ ID NO: 111) | 72 μM |
| Myt1-T455 | STSpTPR (SEQ ID NO: 112) | 40 μM |
| For eSH2 (Grb2) | | |
| c-MET pY1356 | VNATpYVNVKCVA (SEQ ID NO: 113) | 0.2-1 μM |
| ErbB2 pY1139 | SPQPEpYVNQPDVR (SEQ ID NO: 114) | 76 nM |
| SHC (control) | PSpYVNVQN (SEQ ID NO: 115) | 18 nM | n.d.: not determined

TABLE 5

Amino acid sequences of the linker and three FN3 loops of the eSH2's selected for pY1139

| | Linker (cpSH2) | BC | DE | FG |
|---|---|---|---|---|
| eSH2-3 | GGSGGG (SEQ ID NO: 135) | DMWGWVS (SEQ ID NO: 136) | GSSS (SEQ ID NO: 137) | SSSSRISSS (SEQ ID NO: 138) |
| eSH2-6 | GGSGGSG (SEQ ID NO: 139) | DMWGYVS (SEQ ID NO: 140) | GSSS (SEQ ID NO: 141) | SSSSRISSS (SEQ ID NO: 142) |

TABLE 4

Summary of library sorting and binding parameters of affinity clamps

| | BC loop (25-30)[b] | DE loop (52-55)[b] | FG loop (75-83)[b] | $k_{on}[M^{-1}S^{-1}]$[c] | $k_{off}[S^{-1}]$[c] | Kd [nM] ARVCF | Kd [nM] δ-catenin | IC$_{50}$[nM][c] | Affinity Enhancement[d] | Specificity Index[e] |
|---|---|---|---|---|---|---|---|---|---|---|
| Library[a] | X$^{4-8}$VX (SEQ ID NO: 116) | (S/Y)$^4$ (SEQ ID NO: 117) G(S/Y)$^3$ (SEQ ID NO: 118) | X$^{8-14}$ (SEQ ID NO: 119) | | | | | | | |
| cpPDZFN | SSSSVS (SEQ ID NO: 120) | GSKS (SEQ ID NO: 121) | SSSSSSSS (SEQ ID NO: 122) | ND[f] | ND | 24800 ± 13500 | ND | ND | 1 | 2.5[g] |
| ePDZ-a | SYYGVS (SEQ ID NO: 123) | YSSS (SEQ ID NO: 124) | YSDYYGSHHY (SEQ ID NO: 125) | 2.9 × 10$^5$ | 1.5 × 10$^{-2}$ | 56 ± 6 | 429 | 40 | 520 | 8 |
| ePDZ-b | YYDSHVS (SEQ ID NO: 126) | GSKS (SEQ ID NO: 127) | HYNYHYYS (SEQ ID NO: 128) | 1.9 × 10$^5$ | 1.1 × 10$^{-2}$ | 56 ± 6 | >10000 | 59 | 520 | >178 |
| ePDZ-b1 | YRELPVS (SEQ ID NO: 129) | GSKS (SEQ ID NO: 130) | HYNYHYYS (SEQ ID NO: 131) | 7.3 × 10$^4$ | <3.7 × 10$^{-4}$ | 5 ± 1 | >10000 | ND | 4960 | >2000 |
| ePDZ-b2 | FTDLPVS (SEQ ID NO: 132) | GSKS (SEQ ID NO: 133) | HYNYHYYS (SEQ ID NO: 134) | 7.0 × 10$^4$ | <2.9 × 10$^{-4}$ | 4 ± 1 | >10000 | ND | 6200 | >2500 |

[a]The combinatorial library was constructed by diversifying the BC, DE and FG loops of FN3. X denotes an amino acid mixture consisting of 40% Tyr, 20% Ser, 10% Gly and 5% each of A, D, H, L, N and R.
[b]The residue numbering is according to that in Koide et al. (1998).
[c]The $k_{on}$ and $k_{off}$ and IC$_{50}$ were for the ARVCF peptide.
[d]The affinity enhancement is defined as the ratio of the $K_d$ of the parent protein (cpPDZFN) for ARVCF binding to that of an affinity clamp.
[e]The specificity index is defined as the ratio of the $K_d$ for δ-catenin of to the $K_d$ for ARVCF.
[f]ND, not detectable.
[g]Estimated from published data for the wild-type PDZ domain (Skelton et al. 2002).

The invention claimed is:

1. A modular molecular affinity clamp, comprising, in a single molecule:
   first and second biorecognition modules, and optionally, a linker connecting the first and second biorecognition modules,
   the first biorecognition module including at least one interaction domain or mutant interaction domain, wherein the interaction domain is a first molecular recognition domain comprising PDZ, WW, SH2, PTB, SH3, Bromo, Chromo, PHD, Polo-box, TPR, ARM, ANK, or FHA domain,
   the second biorecognition module, including a second molecular recognition domain comprising a polypeptide scaffold that is a fibronectin type three domain (FN3), wherein the first and second recognition domains bind distinct sites within a target peptide motif that is 3-10 amino acid residues in length.

2. The molecular affinity clamp of claim 1, wherein the $K_d$ for the clamp being equal to or lower than one μM.

3. The molecular affinity clamp of claim 1, wherein the first molecular recognition domain comprises a binding pocket of the first biorecognition module.

4. The molecular affinity clamp of claim 1, wherein the target peptide motif a phosphorylated peptide or a methylated peptide.

5. The molecular affinity clamp of claim 4, wherein the target peptide motif is present within a protein.

6. The molecular affinity clamp of claim 1, wherein the first molecular recognition domain is a primary binding domain for the target peptide motif and the second molecular recognition domain is an enhancer domain, and the affinity of the clamp for the target peptide motif is greater than the affinity of the primary binding domain alone for the target peptide motif by a factor of 10 or greater.

7. The molecular affinity clamp of claim 1, wherein the first molecular recognition domain is a primary binding domain for the target peptide motif and the second molecular recognition domain is an enhancer domain, and the specificity of the clamp for the target peptide motif is altered compared to the specificity of the primary binding domain alone for the target peptide motif.

8. The molecular affinity clamp of claim 1, wherein the first molecular recognition domain is a primary binding domain for the target peptide motif and the second molecular recognition domain is an enhancer domain, and the dissociation rate of the clamp for the target peptide motif is slower than the dissociation rate of the primary binding domain alone for the target peptide motif by a factor of 10 or greater.

9. The molecular affinity clamp of claim 1, wherein the first biorecognition module further comprises a first signaling moiety; and the second biorecognition module further comprises a second signaling moiety, the first and second signaling moieties capable of interacting to produce a detectable signal.

10. The molecular affinity clamp of claim 9, where the signaling moiety is a dye, a quencher, a reporter protein, or a quantum dot.

11. The molecular affinity clamp of claim 9, wherein the first and second signaling moieties comprise a fluorescent resonance energy transfer (FRET) donor group and a FRET acceptor group, respectively, and binding of the first and second molecular recognition domains to the target peptide motif results in a change in the FRET efficiency between the FRET donor and FRET acceptor groups.

12. A biosensor, comprising, in a single molecule:
first and second biorecognition modules, and optionally, a linker, the first biorecognition module including a first molecular recognition domain capable of binding a first site of a target peptide motif, wherein the first molecular recognition domain comprises at least one interaction domain or mutant interaction domain, wherein the interaction domain is PDZ, WW, SH2, PTB, SH3, Bromo, Chromo, PHD, Polo-box, TPR, ARM, ANK, or FHA domain the second biorecognition module including a second molecular recognition domain that is a fibronectin type three domain (FN3), wherein the two modules together bind distinct sites within a single target peptide motif that is 3-10 amino acids in length, the first biorecognition module further comprising a first signaling moiety of a signaling pair, and the second biorecognition module further comprising a second signaling moiety of the signaling pair, the first and second signaling moieties capable of interacting to produce a detectable signal when the first and second signaling moieties change proximity with respect to each other upon binding of the first and second molecular recognition domains to the target peptide motif.

13. The biosensor of claim 12, wherein the first and second signaling moieties comprise a fluorescent resonance energy transfer (FRET) donor group and a FRET acceptor group, respectively, and binding of the first and second molecular recognition domains to the target peptide motif results in a change in the distance between the FRET donor and FRET acceptor groups.

14. A biosensor array, comprising:
a plurality of biosensors of claim 12 and a substrate having a surface, each of the biosensors anchored to the substrate surface at an addressable site,
the first and second signaling moieties being in close proximity to establish a FRET signal in the absence of binding to a target peptide motif such that binding of a target peptide motif is effective to modulate the FRET signal.

15. The modular molecular affinity clamp of claim 1, wherein the modular molecular affinity clamp comprises a linker having 30 or fewer amino acid residues.

16. The modular molecular affinity clamp of claim 1, wherein the first or second molecular recognition domain is circularly permutated.

17. The biosensor of claim 12, wherein the target peptide motif is present within a protein.

* * * * *

UNITED STATES PATENT AND TRADEMARK OFFICE
CERTIFICATE OF CORRECTION

PATENT NO. : 9,885,050 B2
APPLICATION NO. : 12/742014
DATED : February 6, 2018
INVENTOR(S) : Shohei Koide et al.

Page 1 of 1

It is certified that error appears in the above-identified patent and that said Letters Patent is hereby corrected as shown below:

In the Specification

In Column 1, at Line 19, the paragraph should read as follows:
-- This invention was made with government support under grant number DK063090 awarded by the National Institutes of Health. The government has certain rights in the invention. --

Signed and Sealed this
Thirtieth Day of August, 2022

Katherine Kelly Vidal
*Director of the United States Patent and Trademark Office*

SEQUENCE LISTING

<160> NUMBER OF SEQ ID NOS: 174

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1

Gly Glu Ile Asp Thr Trp Val
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2

Gly Pro Met Asp Thr Trp Val
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide

<400> SEQUENCE: 3

Gly Pro Leu Asp Thr Trp Val
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide

<400> SEQUENCE: 4

Gly Pro Ile Asp Thr Trp Val
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide

<400> SEQUENCE: 5

Ser Pro Ile Asp Thr Trp Val
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide

<400> SEQUENCE: 6

Gly Pro Ile Asp Thr Trp Val
1               5

```
<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Gly Ser Ile Asp Thr Trp Val
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide

<400> SEQUENCE: 8

Gly Pro Leu Asp Thr Trp Val
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide

<400> SEQUENCE: 9

Ser Asn Ile Asp Thr Trp Val
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic peptide

<400> SEQUENCE: 10

Ser Gln Ile Asp Thr Trp Val
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide

<400> SEQUENCE: 11

Ser Asn Leu Asp Thr Trp Val
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide

<400> SEQUENCE: 12

Arg Asn Ile Asp Thr Trp Val
1               5
```

```
<210> SEQ ID NO 13
<211> LENGTH: 7
<212> TYPE: PRT
<213> ORGANISM: Artificial Sequence
<220> FEATURE:
<223> OTHER INFORMATION: Synthetic peptide

<400> SEQUENCE: 13

Gly Ser Ile Asp Thr Trp Val
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic peptide

<400> SEQUENCE: 14

Thr Ser Ile Asp Thr Trp Val
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide

<400> SEQUENCE: 15

Gly Pro Met Asp Thr Trp Val
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic peptide

<400> SEQUENCE: 16

Lys Arg Gly Ser Ile Asp Ser Trp Val
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic peptide

<400> SEQUENCE: 17

Glu Arg Gly Ala Ile Asp Ser Trp Val
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic peptide

<400> SEQUENCE: 18

Glu Arg Gly Ser Ile Asp Ser Trp Val
1               5

<210> SEQ ID NO 19
```

```
<211> LENGTH: 9
<212> TYPE: PRT
<213> ORGANISM: Artificial Sequence
<220> FEATURE:
<223> OTHER INFORMATION: Synthetic peptide

<400> SEQUENCE: 19

Pro Arg Gly Ser Ile Asp Ser Trp Val
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic peptide

<400> SEQUENCE: 20

Lys Arg Gly Ala Ile Asp Ser Trp Val
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic peptide

<400> SEQUENCE: 21

Lys Arg Met Pro Ile Asp Ser Trp Val
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic peptide

<400> SEQUENCE: 22

Lys Arg Gly Pro Ile Asp Ser Trp Val
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic peptide

<400> SEQUENCE: 23

Pro Arg Met Pro Ile Asp Ser Trp Val
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic peptide

<400> SEQUENCE: 24

Asp Arg Met Pro Phe Asp Ser Trp Val
1               5

<210> SEQ ID NO 25
<211> LENGTH: 9
```

```
<212> TYPE: PRT
<213> ORGANISM: Artificial Sequence
<220> FEATURE:
<223> OTHER INFORMATION: Synthetic peptide

<400> SEQUENCE: 25

Lys Arg Met Pro Leu Asp Ser Trp Val
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic peptide

<400> SEQUENCE: 26

Pro Arg Gly Glu Leu Asp Ser Trp Val
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic peptide

<400> SEQUENCE: 27

Asn Arg Gly Arg Met Asp Ser Trp Val
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic peptide

<400> SEQUENCE: 28

Asp Arg Gly Ser Met Asp Ser Trp Val
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic peptide

<400> SEQUENCE: 29

Lys Arg Gly Ser Met Asp Ser Trp Val
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic peptide

<400> SEQUENCE: 30

Lys Arg Gly Ser Ile Asp Ser Trp Val
1               5

<210> SEQ ID NO 31
<211> LENGTH: 9
<212> TYPE: PRT
```

```
<213> ORGANISM: Artificial Sequence
<220> FEATURE:
<223> OTHER INFORMATION: Synthetic peptide

<400> SEQUENCE: 31

Lys Arg Ser Asn Ile Asp Ser Trp Val
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic peptide

<400> SEQUENCE: 32

Lys Arg Phe Glu Ile Asp Ser Trp Val
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic peptide

<400> SEQUENCE: 33

Lys Arg Phe Asn Ile Asp Ser Trp Val
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic peptide

<400> SEQUENCE: 34

Glu Arg Phe Ser Ile Asp Ser Trp Val
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic peptide

<400> SEQUENCE: 35

Lys Arg Gly Gln Ile Asp Ser Trp Val
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic peptide

<400> SEQUENCE: 36

Phe Arg Gly Glu Ile Asp Ser Trp Val
1               5

<210> SEQ ID NO 37
<211> LENGTH: 9
<212> TYPE: PRT
<213> ORGANISM: Artificial Sequence
```

```
<220> FEATURE:
<223> OTHER INFORMATION: Synthetic peptide

<400> SEQUENCE: 37

Val Arg Gly Glu Ile Asp Ser Trp Val
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic peptide

<400> SEQUENCE: 38

Ser Arg Gly Ala Ile Asp Ser Trp Val
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic peptide

<400> SEQUENCE: 39

Val Arg Gly Ser Ile Asp Ser Trp Val
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic peptide

<400> SEQUENCE: 40

Ala Arg Gly Ser Ile Asp Ser Trp Val
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic peptide

<400> SEQUENCE: 41

Arg Arg Gly Ser Ile Asp Ser Trp Val
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic peptide

<400> SEQUENCE: 42

Gln Arg Gly Asn Ile Asp Ser Trp Val
1               5

<210> SEQ ID NO 43
<211> LENGTH: 9
<212> TYPE: PRT
<213> ORGANISM: Artificial Sequence
<220> FEATURE:
```

<223> OTHER INFORMATION: Synthetic peptide

<400> SEQUENCE: 43

Thr Arg Gly Asn Ile Asp Ser Trp Val
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic peptide

<400> SEQUENCE: 44

Arg Arg Gly Asn Ile Asp Ser Trp Val
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic peptide

<400> SEQUENCE: 45

Gln Arg Trp Asn Ile Asp Ser Trp Val
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic peptide

<400> SEQUENCE: 46

Lys Arg Gly Thr Ile Asp Ser Trp Val
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic peptide

<400> SEQUENCE: 47

Arg Ser Gly Ser Ile Asp Ser Trp Val
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic peptide

<400> SEQUENCE: 48

Glu Arg Ser Ser Ile Asp Ser Trp Val
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic peptide

<400> SEQUENCE: 49

Glu Arg Gln Ser Ile Asp Ser Trp Val
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic peptide

<400> SEQUENCE: 50

Lys Arg Ser Asn Met Asp Ser Trp Val
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic peptide

<400> SEQUENCE: 51

Gly Arg Gly Asn Met Asp Ser Trp Val
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic peptide

<400> SEQUENCE: 52

Asn Arg Gly Gln Met Asp Ser Trp Val
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic peptide

<400> SEQUENCE: 53

Gly Arg Gly Ser Met Asp Ser Trp Val
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic peptide

<400> SEQUENCE: 54

Glu Arg Gly Ser Met Asp Ser Trp Val
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic peptide

```
<400> SEQUENCE: 55

Gly Arg Gly Ser Leu Asp Ser Trp Val
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic peptide

<400> SEQUENCE: 56

Arg Arg Gly Ser Leu Asp Ser Trp Val
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic peptide

<400> SEQUENCE: 57

Lys Arg Asn Ser Leu Asp Ser Trp Val
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic peptide

<400> SEQUENCE: 58

Lys Arg Ser Ser Leu Asp Ser Trp Val
1               5

<210> SEQ ID NO 59
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(11)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid

<400> SEQUENCE: 59

Xaa Xaa Cys Xaa Xaa Xaa Xaa Xaa Xaa Xaa Cys Xaa Xaa
1               5                   10

<210> SEQ ID NO 60
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(2)
```

```
<223> OTHER INFORMATION: Xaa can be any naturally occurring amino acid
<220> FEATURE:
<221> NAME/KEY: MOD_RES
<222> LOCATION: (4)..(12)
<223> OTHER INFORMATION: Xaa can be any naturally occurring amino acid
<220> FEATURE:
<221> NAME/KEY: MOD_RES
<222> LOCATION: (14)..(15)
<223> OTHER INFORMATION: Xaa can be any naturally occurring amino acid

<400> SEQUENCE: 60

Xaa Xaa Cys Xaa Xaa Xaa Xaa Xaa Xaa Xaa Xaa Cys Xaa Xaa
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(2)
<223> OTHER INFORMATION: Xaa can be any naturally occurring amino acid
<220> FEATURE:
<221> NAME/KEY: MOD_RES
<222> LOCATION: (4)..(11)
<223> OTHER INFORMATION: Xaa can be any naturally occurring amino acid
<220> FEATURE:
<221> NAME/KEY: MOD_RES
<222> LOCATION: (13)..(15)
<223> OTHER INFORMATION: Xaa can be any naturally occurring amino acid

<400> SEQUENCE: 61

Xaa Xaa Cys Xaa Xaa Xaa Xaa Xaa Xaa Xaa Cys Xaa Xaa Xaa
1               5                   10                  15

<210> SEQ ID NO 62
<211> LENGTH: 142
<212> TYPE: PRT
<213> ORGANISM: Artificial Sequence
<220> FEATURE:
<223> OTHER INFORMATION: Synthetic peptide

<400> SEQUENCE: 62

Met Lys Lys Ile Trp Leu Ala Leu Ala Gly Leu Val Leu Ala Phe Ser
1               5                   10                  15

Ala Ser Ala Ala Gly Ser Ser Asn Cys Arg His Asn Thr Gly Tyr Asn
            20                  25                  30

Ser Cys Ser Arg Pro Glu Leu Gly Phe Ser Ile Ser Gly Val Gly
        35                  40                  45

Gly Arg Gly Asn Pro Phe Arg Pro Asp Asp Gly Ile Phe Val Thr
    50                  55                  60

Arg Val Gln Pro Glu Gly Pro Ala Ser Lys Leu Leu Gln Pro Gly Asp
65                  70                  75                  80

Lys Ile Ile Gln Ala Asn Gly Tyr Ser Phe Ile Asn Ile Glu His Gly
                85                  90                  95

Gln Ala Val Ser Leu Leu Lys Thr Phe Gln Asn Thr Val Glu Leu Ile
            100                 105                 110

Ile Val Arg Glu Val Gly Asn Gly Ala Lys Gln Glu Ile Arg Val Arg
        115                 120                 125

Val Glu Lys Asp Gly Gly His His His His His His
    130                 135                 140

<210> SEQ ID NO 63
```

<211> LENGTH: 142
<212> TYPE: PRT
<213> ORGANISM: Artificial Sequence
<220> FEATURE:
<223> OTHER INFORMATION: Synthetic peptide

<400> SEQUENCE: 63

```
Met Lys Lys Ile Trp Leu Ala Leu Ala Gly Leu Val Leu Ala Phe Ser
1               5                   10                  15

Ala Ser Ala Ala Gly Ser Asn Phe Cys Ala Ser Asn Gly Thr Gly Asn
            20                  25                  30

Asp Cys Arg Arg Pro Glu Leu Gly Phe Ser Ile Ser Gly Gly Val Gly
        35                  40                  45

Gly Arg Gly Asn Pro Phe Arg Pro Asp Asp Asp Gly Ile Phe Val Thr
    50                  55                  60

Arg Val Gln Pro Glu Gly Pro Ala Ser Lys Leu Leu Gln Pro Gly Asp
65                  70                  75                  80

Lys Ile Ile Gln Ala Asn Gly Tyr Ser Phe Ile Asn Ile Glu His Gly
                85                  90                  95

Gln Ala Val Ser Leu Leu Lys Thr Phe Gln Asn Thr Val Glu Leu Ile
            100                 105                 110

Ile Val Arg Glu Val Gly Asn Gly Ala Lys Gln Glu Ile Arg Val Arg
        115                 120                 125

Val Glu Lys Asp Gly Gly His His His His His His His
    130                 135                 140
```

<210> SEQ ID NO 64
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(3)
<223> OTHER INFORMATION: Xaa = s, t, a, v, i, f
<220> FEATURE:
<221> NAME/KEY: MOD_RES
<222> LOCATION: (4)..(4)
<223> OTHER INFORMATION: Xaa = i, l, v, a, t, p
<220> FEATURE:
<221> NAME/KEY: MOD_RES
<222> LOCATION: (11)..(11)
<223> OTHER INFORMATION: Xaa can be any naturally occurring amino acid

<400> SEQUENCE: 64

```
Xaa Xaa Xaa Xaa Ser Thr Ala Val Ile Phe Xaa Ile Leu Val Ala Thr
1               5                   10                  15

Pro
```

<210> SEQ ID NO 65
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(5)
<223> OTHER INFORMATION: Xaa can be any naturally occurring amino acid

<400> SEQUENCE: 65

```
Xaa Xaa Xaa Xaa Xaa Asp Ser Trp Val
1               5
```

```
<210> SEQ ID NO 66
<211> LENGTH: 8
<212> TYPE: PRT
<213> ORGANISM: Artificial Sequence
<220> FEATURE:
<223> OTHER INFORMATION: Synthetic peptide

<400> SEQUENCE: 66

Pro Gln Pro Val Asp Ser Trp Val
1               5

<210> SEQ ID NO 67
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(2)
<223> OTHER INFORMATION: Xaa = s or t
<220> FEATURE:
<221> NAME/KEY: MOD_RES
<222> LOCATION: (3)..(5)
<223> OTHER INFORMATION: Xaa = i, l, v

<400> SEQUENCE: 67

Xaa Xaa Xaa Xaa Xaa
1               5

<210> SEQ ID NO 68
<211> LENGTH: 10
<212> TYPE: PRT
<213> ORGANISM: Artificial Sequence
<220> FEATURE:
<223> OTHER INFORMATION: Synthetic peptide

<400> SEQUENCE: 68

Gly Gly Arg Ser Trp Phe Glu Thr Trp Val
1               5                   10

<210> SEQ ID NO 69
<211> LENGTH: 4
<212> TYPE: PRT
<213> ORGANISM: Artificial Sequence
<220> FEATURE:
<223> OTHER INFORMATION: Synthetic peptide

<400> SEQUENCE: 69

Asp Ser Trp Val
1

<210> SEQ ID NO 70
<211> LENGTH: 8
<212> TYPE: PRT
<213> ORGANISM: Artificial Sequence
<220> FEATURE:
<223> OTHER INFORMATION: Synthetic peptide

<400> SEQUENCE: 70

Pro Ala Ser Pro Asp Ser Trp Val
1               5

<210> SEQ ID NO 71
<211> LENGTH: 4
<212> TYPE: PRT
<213> ORGANISM: Artificial Sequence
<220> FEATURE:
```

```
<223> OTHER INFORMATION: Synthetic peptide

<400> SEQUENCE: 71

Asp Thr Trp Val
1

<210> SEQ ID NO 72
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa = r
<220> FEATURE:
<221> NAME/KEY: MOD_RES
<222> LOCATION: (2)..(2)
<223> OTHER INFORMATION: Xaa = g or s
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: Xaa = i, l, m

<400> SEQUENCE: 72

Xaa Xaa Xaa Xaa Asp Ser Trp Val
1               5

<210> SEQ ID NO 73
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa = r
<220> FEATURE:
<221> NAME/KEY: MOD_RES
<222> LOCATION: (2)..(2)
<223> OTHER INFORMATION: Xaa = g or s
<220> FEATURE:
<221> NAME/KEY: MOD_RES
<222> LOCATION: (3)..(3)
<223> OTHER INFORMATION: Xaa = n or s
<220> FEATURE:
<221> NAME/KEY: MOD_RES
<222> LOCATION: (4)..(4)
<223> OTHER INFORMATION: Xaa = i, l, m

<400> SEQUENCE: 73

Xaa Xaa Xaa Xaa Asp Ser Trp Val
1               5

<210> SEQ ID NO 74
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa = e or d
<220> FEATURE:
<221> NAME/KEY: MOD_RES
<222> LOCATION: (2)..(2)
```

<223> OTHER INFORMATION: Xaa = t or s

<400> SEQUENCE: 74

Xaa Xaa Trp Val
1

<210> SEQ ID NO 75
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa = s or t
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: Xaa = Xaa = l, i, v
<220> FEATURE:
<221> NAME/KEY: misc_feature
<222> LOCATION: (8)..(8)
<223> OTHER INFORMATION: Xaa can be any naturally occurring amino acid

<400> SEQUENCE: 75

Glu Xaa Xaa Xaa Glu Ser Thr Xaa Leu Ile Val
1               5                   10

<210> SEQ ID NO 76
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: Xaa = q, y, v
<220> FEATURE:
<221> NAME/KEY: MOD_RES
<222> LOCATION: (5)..(5)
<223> OTHER INFORMATION: Xaa = y, q, f

<400> SEQUENCE: 76

Pro Tyr Xaa Asn Xaa
1               5

<210> SEQ ID NO 77
<211> LENGTH: 98
<212> TYPE: PRT
<213> ORGANISM: Artificial Sequence
<220> FEATURE:
<223> OTHER INFORMATION: Synthetic peptide

<400> SEQUENCE: 77

Lys Pro His Pro Trp Phe Phe Gly Lys Ile Pro Arg Ala Lys Ala Glu
1               5                   10                  15

Glu Met Leu Ser Lys Gln Arg His Asp Gly Ala Phe Leu Ile Arg Glu
            20                  25                  30

Ser Glu Ser Ala Pro Gly Asp Phe Ser Leu Ser Val Lys Phe Gly Asn
        35                  40                  45

Asp Val Gln His Phe Lys Val Leu Arg Asp Gly Ala Gly Lys Tyr Phe
    50                  55                  60

```
Leu Trp Val Val Lys Phe Asn Ser Leu Asn Glu Leu Val Asp Tyr His
 65                  70                  75                  80

Arg Ser Thr Ser Val Ser Arg Asn Gln Gln Ile Phe Leu Arg Asp Ile
                 85                  90                  95

Glu Gln

<210> SEQ ID NO 78
<211> LENGTH: 18
<212> TYPE: PRT
<213> ORGANISM: Artificial Sequence
<220> FEATURE:
<223> OTHER INFORMATION: Synthetic peptide

<400> SEQUENCE: 78

Pro Leu Thr Cys Ser Pro Gln Pro Glu Pro Tyr Val Asn Gln Pro Asp
 1               5                  10                  15

Val Arg

<210> SEQ ID NO 79
<211> LENGTH: 9
<212> TYPE: PRT
<213> ORGANISM: Artificial Sequence
<220> FEATURE:
<223> OTHER INFORMATION: Synthetic peptide

<400> SEQUENCE: 79

Gly Gly Ser Ser Ser Gly Ser Ser Ser
 1               5

<210> SEQ ID NO 80
<211> LENGTH: 7
<212> TYPE: PRT
<213> ORGANISM: Artificial Sequence
<220> FEATURE:
<223> OTHER INFORMATION: Synthetic peptide

<400> SEQUENCE: 80

Val Pro Arg Pro Thr Pro Val
 1               5

<210> SEQ ID NO 81
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: Xaa = i, l, m
<220> FEATURE:
<221> NAME/KEY: misc_feature
<222> LOCATION: (5)..(5)
<223> OTHER INFORMATION: Xaa can be any naturally occurring amino acid

<400> SEQUENCE: 81

Pro Tyr Xaa Xaa Xaa
 1               5

<210> SEQ ID NO 82
<211> LENGTH: 4
<212> TYPE: PRT
<213> ORGANISM: Artificial Sequence
```

```
<220> FEATURE:
<223> OTHER INFORMATION: Synthetic peptide

<400> SEQUENCE: 82

Gly Tyr Cys Asp
1

<210> SEQ ID NO 83
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: Lys is methylated

<400> SEQUENCE: 83

Gln Thr Ala Arg Lys Ser Thr
1               5

<210> SEQ ID NO 84
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: Lys is methylated

<400> SEQUENCE: 84

Lys Ala Ala Arg Lys Ser Ala
1               5

<210> SEQ ID NO 85
<211> LENGTH: 7
<212> TYPE: PRT
<213> ORGANISM: Artificial Sequence
<220> FEATURE:
<223> OTHER INFORMATION: Synthetic peptide

<400> SEQUENCE: 85

Ala Ser Ser Ser Ser Val Ser
1               5

<210> SEQ ID NO 86
<211> LENGTH: 6
<212> TYPE: PRT
<213> ORGANISM: Artificial Sequence
<220> FEATURE:
<223> OTHER INFORMATION: Synthetic peptide

<400> SEQUENCE: 86

Pro Gly Ser Lys Ser Thr
1               5

<210> SEQ ID NO 87
<211> LENGTH: 14
<212> TYPE: PRT
<213> ORGANISM: Artificial Sequence
<220> FEATURE:
<223> OTHER INFORMATION: Synthetic peptide

<400> SEQUENCE: 87

Ala Ser Ser Ser Ser Ser Ser Ser Ser Ser Ser Ser Lys Pro
```

```
1               5                   10
```

<210> SEQ ID NO 88
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(5)
<223> OTHER INFORMATION: Xaa = y, s, g, r, l, h, d ,n and/or a
<220> FEATURE:
<221> NAME/KEY: MOD_RES
<222> LOCATION: (7)..(7)
<223> OTHER INFORMATION: Xaa = y, s, g, r, l, h, d ,n and/or a

<400> SEQUENCE: 88

Ala Xaa Xaa Xaa Xaa Val Xaa
1               5

<210> SEQ ID NO 89
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(6)
<223> OTHER INFORMATION: Xaa = y, s, g, r, l, h, d ,n and/or a
<220> FEATURE:
<221> NAME/KEY: MOD_RES
<222> LOCATION: (8)..(8)
<223> OTHER INFORMATION: Xaa = y, s, g, r, l, h, d ,n and/or a

<400> SEQUENCE: 89

Ala Xaa Xaa Xaa Xaa Xaa Val Xaa
1               5

<210> SEQ ID NO 90
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(7)
<223> OTHER INFORMATION: Xaa = y, s, g, r, l, h, d ,n and/or a
<220> FEATURE:
<221> NAME/KEY: MOD_RES
<222> LOCATION: (9)..(9)
<223> OTHER INFORMATION: Xaa = y, s, g, r, l, h, d ,n and/or a

<400> SEQUENCE: 90

Ala Xaa Xaa Xaa Xaa Xaa Xaa Val Xaa
1               5

<210> SEQ ID NO 91
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(8)
<223> OTHER INFORMATION: Xaa = y, s, g, r, l, h, d ,n and/or a
<220> FEATURE:
<221> NAME/KEY: MOD_RES
<222> LOCATION: (10)..(10)

<223> OTHER INFORMATION: Xaa = y, s, g, r, l, h, d ,n and/or a

<400> SEQUENCE: 91

Ala Xaa Xaa Xaa Xaa Xaa Xaa Xaa Val Xaa
1               5                   10

<210> SEQ ID NO 92
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(9)
<223> OTHER INFORMATION: Xaa = y, s, g, r, l, h, d ,n and/or a
<220> FEATURE:
<221> NAME/KEY: MOD_RES
<222> LOCATION: (11)..(11)
<223> OTHER INFORMATION: Xaa = y, s, g, r, l, h, d ,n and/or a

<400> SEQUENCE: 92

Ala Xaa Xaa Xaa Xaa Xaa Xaa Xaa Xaa Val Xaa
1               5                   10

<210> SEQ ID NO 93
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(4)
<223> OTHER INFORMATION: Xaa = y, s, g
<220> FEATURE:
<221> NAME/KEY: MOD_RES
<222> LOCATION: (5)..(6)
<223> OTHER INFORMATION: Xaa = s or y

<400> SEQUENCE: 93

Pro Xaa Xaa Xaa Xaa Xaa Thr
1               5

<210> SEQ ID NO 94
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(9)
<223> OTHER INFORMATION: Xaa = y, s, g, r, l, h, d, n and/or a

<400> SEQUENCE: 94

Ala Xaa Xaa Xaa Xaa Xaa Xaa Xaa Xaa Ser Pro
1               5                   10

<210> SEQ ID NO 95
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(10)
<223> OTHER INFORMATION: Xaa = y, s, g, r, l, h, d, n and/or a

<400> SEQUENCE: 95

```
Ala Xaa Xaa Xaa Xaa Xaa Xaa Xaa Xaa Ser Pro
1               5                   10

<210> SEQ ID NO 96
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(11)
<223> OTHER INFORMATION: Xaa = y, s, g, r, l, h, d, n and/or a

<400> SEQUENCE: 96

Ala Xaa Xaa Xaa Xaa Xaa Xaa Xaa Xaa Xaa Xaa Ser Pro
1               5                   10

<210> SEQ ID NO 97
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(12)
<223> OTHER INFORMATION: Xaa = y, s, g, r, l, h, d, n and/or a

<400> SEQUENCE: 97

Ala Xaa Xaa Xaa Xaa Xaa Xaa Xaa Xaa Xaa Xaa Xaa Ser Pro
1               5                   10

<210> SEQ ID NO 98
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(13)
<223> OTHER INFORMATION: Xaa = y, s, g, r, l, h, d, n and/or a

<400> SEQUENCE: 98

Ala Xaa Xaa Xaa Xaa Xaa Xaa Xaa Xaa Xaa Xaa Xaa Xaa Ser Pro
1               5                   10                  15

<210> SEQ ID NO 99
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(14)
<223> OTHER INFORMATION: Xaa = y, s, g, r, l, h, d, n and/or a

<400> SEQUENCE: 99

Ala Xaa Xaa Xaa Xaa Xaa Xaa Xaa Xaa Xaa Xaa Xaa Xaa Xaa Ser Pro
1               5                   10                  15

<210> SEQ ID NO 100
<211> LENGTH: 17
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MOD_RES
<222> LOCATION: (2)..(15)
<223> OTHER INFORMATION: Xaa = y, s, g, r, l, h, d, n and/or a

<400> SEQUENCE: 100

Ala Xaa Xaa Xaa Xaa Xaa Xaa Xaa Xaa Xaa Xaa Xaa Xaa Xaa Ser
1               5                   10                  15
Pro

<210> SEQ ID NO 101
<211> LENGTH: 7
<212> TYPE: PRT
<213> ORGANISM: Artificial Sequence
<220> FEATURE:
<223> OTHER INFORMATION: Synthetic peptide

<400> SEQUENCE: 101

Ala Ser Tyr Tyr Gly Val Ser
1               5

<210> SEQ ID NO 102
<211> LENGTH: 6
<212> TYPE: PRT
<213> ORGANISM: Artificial Sequence
<220> FEATURE:
<223> OTHER INFORMATION: Synthetic peptide

<400> SEQUENCE: 102

Pro Tyr Ser Ser Ser Thr
1               5

<210> SEQ ID NO 103
<211> LENGTH: 13
<212> TYPE: PRT
<213> ORGANISM: Artificial Sequence
<220> FEATURE:
<223> OTHER INFORMATION: Synthetic peptide

<400> SEQUENCE: 103

Ala Tyr Ser Asp Tyr Tyr Gly Ser His His Tyr Ser Pro
1               5                   10

<210> SEQ ID NO 104
<211> LENGTH: 8
<212> TYPE: PRT
<213> ORGANISM: Artificial Sequence
<220> FEATURE:
<223> OTHER INFORMATION: Synthetic peptide

<400> SEQUENCE: 104

Ala Tyr Tyr Asp Ser His Val Ser
1               5

<210> SEQ ID NO 105
<211> LENGTH: 6
<212> TYPE: PRT
<213> ORGANISM: Artificial Sequence
<220> FEATURE:
<223> OTHER INFORMATION: Synthetic peptide

<400> SEQUENCE: 105

Pro Gly Ser Lys Ser Thr
1               5

<210> SEQ ID NO 106
```

```
<211> LENGTH: 11
<212> TYPE: PRT
<213> ORGANISM: Artificial Sequence
<220> FEATURE:
<223> OTHER INFORMATION: Synthetic peptide

<400> SEQUENCE: 106

Ala His Tyr Asn Tyr His Tyr Tyr Ser Ser Pro
1               5                   10

<210> SEQ ID NO 107
<211> LENGTH: 8
<212> TYPE: PRT
<213> ORGANISM: Artificial Sequence
<220> FEATURE:
<223> OTHER INFORMATION: Synthetic peptide

<400> SEQUENCE: 107

Pro Gln Pro Val Asp Ser Trp Val
1               5

<210> SEQ ID NO 108
<211> LENGTH: 8
<212> TYPE: PRT
<213> ORGANISM: Artificial Sequence
<220> FEATURE:
<223> OTHER INFORMATION: Synthetic peptide

<400> SEQUENCE: 108

Pro Ala Ser Pro Asp Ser Trp Val
1               5

<210> SEQ ID NO 109
<211> LENGTH: 6
<212> TYPE: PRT
<213> ORGANISM: Artificial Sequence
<220> FEATURE:
<223> OTHER INFORMATION: Synthetic peptide

<400> SEQUENCE: 109

Gly Gly Ser Gly Gly Ser
1               5

<210> SEQ ID NO 110
<211> LENGTH: 7
<212> TYPE: PRT
<213> ORGANISM: Artificial Sequence
<220> FEATURE:
<223> OTHER INFORMATION: Synthetic peptide

<400> SEQUENCE: 110

Pro Pro Ala Pro Thr Pro Pro
1               5

<210> SEQ ID NO 111
<211> LENGTH: 8
<212> TYPE: PRT
<213> ORGANISM: Artificial Sequence
<220> FEATURE:
<223> OTHER INFORMATION: Synthetic peptide

<400> SEQUENCE: 111

Tyr Ser Pro Thr Pro Ser Pro Ser
1               5

<210> SEQ ID NO 112
<211> LENGTH: 8
```

```
<212> TYPE: PRT
<213> ORGANISM: Artificial Sequence
<220> FEATURE:
<223> OTHER INFORMATION: Synthetic peptide

<400> SEQUENCE: 112

Lys Ala Pro Lys Pro Ser Pro Ala
1               5

<210> SEQ ID NO 113
<211> LENGTH: 9
<212> TYPE: PRT
<213> ORGANISM: Artificial Sequence
<220> FEATURE:
<223> OTHER INFORMATION: Synthetic peptide

<400> SEQUENCE: 113

Thr Pro Pro Leu Pro Ser Pro Ser Arg
1               5

<210> SEQ ID NO 114
<211> LENGTH: 9
<212> TYPE: PRT
<213> ORGANISM: Artificial Sequence
<220> FEATURE:
<223> OTHER INFORMATION: Synthetic peptide

<400> SEQUENCE: 114

Thr Pro Pro Leu Pro Ser Pro Ile Asp
1               5

<210> SEQ ID NO 115
<211> LENGTH: 9
<212> TYPE: PRT
<213> ORGANISM: Artificial Sequence
<220> FEATURE:
<223> OTHER INFORMATION: Synthetic peptide

<400> SEQUENCE: 115

Val Thr Pro Arg Pro Thr Pro Pro Pro
1               5

<210> SEQ ID NO 116
<211> LENGTH: 9
<212> TYPE: PRT
<213> ORGANISM: Artificial Sequence
<220> FEATURE:
<223> OTHER INFORMATION: Synthetic peptide

<400> SEQUENCE: 116

Ile Ala Pro Arg Pro Ser Pro Ala Lys
1               5

<210> SEQ ID NO 117
<211> LENGTH: 9
<212> TYPE: PRT
<213> ORGANISM: Artificial Sequence
<220> FEATURE:
<223> OTHER INFORMATION: Synthetic peptide

<400> SEQUENCE: 117

Asp Gly Pro Ser Pro Thr Pro Gly Pro
1               5

<210> SEQ ID NO 118
<211> LENGTH: 9
<212> TYPE: PRT
```

```
<213> ORGANISM: Artificial Sequence
<220> FEATURE:
<223> OTHER INFORMATION: Synthetic peptide

<400> SEQUENCE: 118

Val Glu Pro Leu Pro Thr Pro Ser Gly
1               5

<210> SEQ ID NO 119
<211> LENGTH: 9
<212> TYPE: PRT
<213> ORGANISM: Artificial Sequence
<220> FEATURE:
<223> OTHER INFORMATION: Synthetic peptide

<400> SEQUENCE: 119

Ser Leu Pro Thr Pro Ser Pro Val Ser
1               5

<210> SEQ ID NO 120
<211> LENGTH: 9
<212> TYPE: PRT
<213> ORGANISM: Artificial Sequence
<220> FEATURE:
<223> OTHER INFORMATION: Synthetic peptide

<400> SEQUENCE: 120

Pro Pro Gln Leu Pro Ser Pro Phe Leu
1               5

<210> SEQ ID NO 121
<211> LENGTH: 7
<212> TYPE: PRT
<213> ORGANISM: Artificial Sequence
<220> FEATURE:
<223> OTHER INFORMATION: Synthetic peptide

<400> SEQUENCE: 121

Leu Tyr Arg Pro Ser Pro Ser
1               5

<210> SEQ ID NO 122
<211> LENGTH: 7
<212> TYPE: PRT
<213> ORGANISM: Artificial Sequence
<220> FEATURE:
<223> OTHER INFORMATION: Synthetic peptide

<400> SEQUENCE: 122

Ser Thr Ser Pro Thr Pro Arg
1               5

<210> SEQ ID NO 123
<211> LENGTH: 13
<212> TYPE: PRT
<213> ORGANISM: Artificial Sequence
<220> FEATURE:
<223> OTHER INFORMATION: Synthetic peptide

<400> SEQUENCE: 123

Val Asn Ala Thr Pro Tyr Val Asn Val Lys Cys Val Ala
1               5                   10

<210> SEQ ID NO 124
<211> LENGTH: 14
<212> TYPE: PRT
<213> ORGANISM: Artificial Sequence
```

```
<220> FEATURE:
<223> OTHER INFORMATION: Synthetic peptide

<400> SEQUENCE: 124

Ser Pro Gln Pro Glu Pro Tyr Val Asn Gln Pro Asp Val Arg
1               5                   10

<210> SEQ ID NO 125
<211> LENGTH: 9
<212> TYPE: PRT
<213> ORGANISM: Artificial Sequence
<220> FEATURE:
<223> OTHER INFORMATION: Synthetic peptide

<400> SEQUENCE: 125

Pro Ser Pro Tyr Val Asn Val Gln Asn
1               5

<210> SEQ ID NO 126
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(4)
<223> OTHER INFORMATION: Xaa = y, s, g, , a, d, h, l, n and/or r
<220> FEATURE:
<221> NAME/KEY: misc_feature
<222> LOCATION: (6)..(6)
<223> OTHER INFORMATION: Xaa can be any naturally occurring amino acid

<400> SEQUENCE: 126

Xaa Xaa Xaa Xaa Val Xaa
1               5

<210> SEQ ID NO 127
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(5)
<223> OTHER INFORMATION: Xaa = y, s, g, , a, d, h, l, n and/or r
<220> FEATURE:
<221> NAME/KEY: misc_feature
<222> LOCATION: (7)..(7)
<223> OTHER INFORMATION: Xaa can be any naturally occurring amino acid

<400> SEQUENCE: 127

Xaa Xaa Xaa Xaa Xaa Val Xaa
1               5

<210> SEQ ID NO 128
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(6)
<223> OTHER INFORMATION: Xaa = y, s, g, , a, d, h, l, n and/or r
<220> FEATURE:
<221> NAME/KEY: misc_feature
<222> LOCATION: (8)..(8)
<223> OTHER INFORMATION: Xaa can be any naturally occurring amino acid
```

```
<400> SEQUENCE: 128

Xaa Xaa Xaa Xaa Xaa Xaa Val Xaa
1               5

<210> SEQ ID NO 129
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(7)
<223> OTHER INFORMATION: Xaa = y, s, g, , a, d, h, l, n and/or r
<220> FEATURE:
<221> NAME/KEY: misc_feature
<222> LOCATION: (9)..(9)
<223> OTHER INFORMATION: Xaa can be any naturally occurring amino acid

<400> SEQUENCE: 129

Xaa Xaa Xaa Xaa Xaa Xaa Xaa Val Xaa
1               5

<210> SEQ ID NO 130
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(8)
<223> OTHER INFORMATION: Xaa = y, s, g, , a, d, h, l, n and/or r
<220> FEATURE:
<221> NAME/KEY: misc_feature
<222> LOCATION: (10)..(10)
<223> OTHER INFORMATION: Xaa can be any naturally occurring amino acid

<400> SEQUENCE: 130

Xaa Xaa Xaa Xaa Xaa Xaa Xaa Xaa Val Xaa
1               5                   10

<210> SEQ ID NO 131
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(4)
<223> OTHER INFORMATION: Xaa = s or y

<400> SEQUENCE: 131

Xaa Xaa Xaa Xaa
1

<210> SEQ ID NO 132
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(4)
<223> OTHER INFORMATION: Xaa = s or y

<400> SEQUENCE: 132

Gly Xaa Xaa Xaa
```

```
<210> SEQ ID NO 133
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(8)
<223> OTHER INFORMATION: Xaa = y, s, g, , a, d, h, l, n and/or r

<400> SEQUENCE: 133

Xaa Xaa Xaa Xaa Xaa Xaa Xaa Xaa
1               5

<210> SEQ ID NO 134
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(9)
<223> OTHER INFORMATION: Xaa = y, s, g, , a, d, h, l, n and/or r

<400> SEQUENCE: 134

Xaa Xaa Xaa Xaa Xaa Xaa Xaa Xaa Xaa
1               5

<210> SEQ ID NO 135
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(10)
<223> OTHER INFORMATION: Xaa = y, s, g, , a, d, h, l, n and/or r

<400> SEQUENCE: 135

Xaa Xaa Xaa Xaa Xaa Xaa Xaa Xaa Xaa Xaa
1               5                   10

<210> SEQ ID NO 136
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(11)
<223> OTHER INFORMATION: Xaa = y, s, g, , a, d, h, l, n and/or r

<400> SEQUENCE: 136

Xaa Xaa Xaa Xaa Xaa Xaa Xaa Xaa Xaa Xaa Xaa
1               5                   10

<210> SEQ ID NO 137
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
```

```
<222> LOCATION: (1)..(12)
<223> OTHER INFORMATION: Xaa = y, s, g, , a, d, h, l, n and/or r

<400> SEQUENCE: 137

Xaa Xaa Xaa Xaa Xaa Xaa Xaa Xaa Xaa Xaa Xaa Xaa
1               5                   10

<210> SEQ ID NO 138
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(13)
<223> OTHER INFORMATION: Xaa = y, s, g, , a, d, h, l, n and/or r

<400> SEQUENCE: 138

Xaa Xaa Xaa Xaa Xaa Xaa Xaa Xaa Xaa Xaa Xaa Xaa Xaa
1               5                   10

<210> SEQ ID NO 139
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(14)
<223> OTHER INFORMATION: Xaa = y, s, g, , a, d, h, l, n and/or r

<400> SEQUENCE: 139

Xaa Xaa Xaa Xaa Xaa Xaa Xaa Xaa Xaa Xaa Xaa Xaa Xaa Xaa
1               5                   10

<210> SEQ ID NO 140
<211> LENGTH: 6
<212> TYPE: PRT
<213> ORGANISM: Artificial Sequence
<220> FEATURE:
<223> OTHER INFORMATION: Synthetic peptide

<400> SEQUENCE: 140

Ser Ser Ser Ser Val Ser
1               5

<210> SEQ ID NO 141
<211> LENGTH: 4
<212> TYPE: PRT
<213> ORGANISM: Artificial Sequence
<220> FEATURE:
<223> OTHER INFORMATION: Synthetic peptide

<400> SEQUENCE: 141

Gly Ser Lys Ser
1

<210> SEQ ID NO 142
<211> LENGTH: 9
<212> TYPE: PRT
<213> ORGANISM: Artificial Sequence
<220> FEATURE:
<223> OTHER INFORMATION: Synthetic peptide

<400> SEQUENCE: 142

Ser Ser Ser Ser Ser Ser Ser Ser Ser
```

```
<210> SEQ ID NO 143
<211> LENGTH: 6
<212> TYPE: PRT
<213> ORGANISM: Artificial Sequence
<220> FEATURE:
<223> OTHER INFORMATION: Synthetic peptide

<400> SEQUENCE: 143

Ser Tyr Tyr Gly Val Ser
1               5

<210> SEQ ID NO 144
<211> LENGTH: 4
<212> TYPE: PRT
<213> ORGANISM: Artificial Sequence
<220> FEATURE:
<223> OTHER INFORMATION: Synthetic peptide

<400> SEQUENCE: 144

Tyr Ser Ser Ser
1

<210> SEQ ID NO 145
<211> LENGTH: 10
<212> TYPE: PRT
<213> ORGANISM: Artificial Sequence
<220> FEATURE:
<223> OTHER INFORMATION: Synthetic peptide

<400> SEQUENCE: 145

Tyr Ser Asp Tyr Tyr Gly Ser His His Tyr
1               5                   10

<210> SEQ ID NO 146
<211> LENGTH: 7
<212> TYPE: PRT
<213> ORGANISM: Artificial Sequence
<220> FEATURE:
<223> OTHER INFORMATION: Synthetic peptide

<400> SEQUENCE: 146

Tyr Tyr Asp Ser His Val Ser
1               5

<210> SEQ ID NO 147
<211> LENGTH: 4
<212> TYPE: PRT
<213> ORGANISM: Artificial Sequence
<220> FEATURE:
<223> OTHER INFORMATION: Synthetic peptide

<400> SEQUENCE: 147

Gly Ser Lys Ser
1

<210> SEQ ID NO 148
<211> LENGTH: 8
<212> TYPE: PRT
<213> ORGANISM: Artificial Sequence
<220> FEATURE:
<223> OTHER INFORMATION: Synthetic peptide

<400> SEQUENCE: 148

His Tyr Asn Tyr His Tyr Tyr Ser
1               5
```

<210> SEQ ID NO 149
<211> LENGTH: 7
<212> TYPE: PRT
<213> ORGANISM: Artificial Sequence
<220> FEATURE:
<223> OTHER INFORMATION: Synthetic peptide

<400> SEQUENCE: 149

Tyr Arg Glu Leu Pro Val Ser
1               5

<210> SEQ ID NO 150
<211> LENGTH: 4
<212> TYPE: PRT
<213> ORGANISM: Artificial Sequence
<220> FEATURE:
<223> OTHER INFORMATION: Synthetic peptide

<400> SEQUENCE: 150

Gly Ser Lys Ser
1

<210> SEQ ID NO 151
<211> LENGTH: 8
<212> TYPE: PRT
<213> ORGANISM: Artificial Sequence
<220> FEATURE:
<223> OTHER INFORMATION: Synthetic peptide

<400> SEQUENCE: 151

His Tyr Asn Tyr His Tyr Tyr Ser
1               5

<210> SEQ ID NO 152
<211> LENGTH: 7
<212> TYPE: PRT
<213> ORGANISM: Artificial Sequence
<220> FEATURE:
<223> OTHER INFORMATION: Synthetic peptide

<400> SEQUENCE: 152

Phe Thr Asp Leu Pro Val Ser
1               5

<210> SEQ ID NO 153
<211> LENGTH: 4
<212> TYPE: PRT
<213> ORGANISM: Artificial Sequence
<220> FEATURE:
<223> OTHER INFORMATION: Synthetic peptide

<400> SEQUENCE: 153

Gly Ser Lys Ser
1

<210> SEQ ID NO 154
<211> LENGTH: 8
<212> TYPE: PRT
<213> ORGANISM: Artificial Sequence
<220> FEATURE:
<223> OTHER INFORMATION: Synthetic peptide

<400> SEQUENCE: 154

His Tyr Asn Tyr His Tyr Tyr Ser
1               5

<210> SEQ ID NO 155
<211> LENGTH: 6
<212> TYPE: PRT
<213> ORGANISM: Artificial Sequence
<220> FEATURE:
<223> OTHER INFORMATION: Synthetic peptide

<400> SEQUENCE: 155

Gly Gly Ser Gly Gly Gly
1               5

<210> SEQ ID NO 156
<211> LENGTH: 7
<212> TYPE: PRT
<213> ORGANISM: Artificial Sequence
<220> FEATURE:
<223> OTHER INFORMATION: Synthetic peptide

<400> SEQUENCE: 156

Asp Met Trp Gly Trp Val Ser
1               5

<210> SEQ ID NO 157
<211> LENGTH: 4
<212> TYPE: PRT
<213> ORGANISM: Artificial Sequence
<220> FEATURE:
<223> OTHER INFORMATION: Synthetic peptide

<400> SEQUENCE: 157

Gly Ser Ser Ser
1

<210> SEQ ID NO 158
<211> LENGTH: 9
<212> TYPE: PRT
<213> ORGANISM: Artificial Sequence
<220> FEATURE:
<223> OTHER INFORMATION: Synthetic peptide

<400> SEQUENCE: 158

Ser Ser Ser Ser Arg Ile Ser Ser Ser
1               5

<210> SEQ ID NO 159
<211> LENGTH: 7
<212> TYPE: PRT
<213> ORGANISM: Artificial Sequence
<220> FEATURE:
<223> OTHER INFORMATION: Synthetic peptide

<400> SEQUENCE: 159

Gly Gly Ser Gly Gly Ser Gly
1               5

<210> SEQ ID NO 160
<211> LENGTH: 7
<212> TYPE: PRT
<213> ORGANISM: Artificial Sequence
<220> FEATURE:
<223> OTHER INFORMATION: Synthetic peptide

<400> SEQUENCE: 160

Asp Met Trp Gly Tyr Val Ser
1               5

```
<210> SEQ ID NO 161
<211> LENGTH: 5
<212> TYPE: PRT
<213> ORGANISM: Artificial Sequence
<220> FEATURE:
<223> OTHER INFORMATION: Synthetic peptide

<400> SEQUENCE: 161

Gly Ser Ser Ser Ser
1               5

<210> SEQ ID NO 162
<211> LENGTH: 9
<212> TYPE: PRT
<213> ORGANISM: Artificial Sequence
<220> FEATURE:
<223> OTHER INFORMATION: Synthetic peptide

<400> SEQUENCE: 162

Ser Ser Ser Ser Arg Ile Ser Ser Ser
1               5

<210> SEQ ID NO 163
<211> LENGTH: 222
<212> TYPE: PRT
<213> ORGANISM: Artificial Sequence
<220> FEATURE:
<223> OTHER INFORMATION: Synthetic peptide

<400> SEQUENCE: 163

His His His His His His His His Ser Ser Asp Tyr Lys Asp
1               5                   10                  15

Asp Asp Asp Lys Gly Glu Asn Leu Tyr Phe Gln Gly Ser Pro Glu Leu
                20                  25                  30

Gly Phe Ser Ile Ser Gly Gly Val Gly Gly Arg Gly Asn Pro Phe Arg
            35                  40                  45

Pro Asp Asp Asp Gly Ile Phe Val Thr Arg Val Gln Pro Glu Gly Pro
        50                  55                  60

Ala Ser Lys Leu Leu Gln Pro Gly Asp Lys Ile Ile Gln Ala Asn Gly
65                  70                  75                  80

Tyr Ser Phe Ile Asn Ile Glu His Gly Gln Ala Val Ser Leu Leu Lys
                85                  90                  95

Thr Phe Gln Asn Thr Val Glu Leu Ile Ile Val Arg Glu Val Gly Asn
            100                 105                 110

Gly Ala Lys Gln Glu Ile Arg Val Arg Val Glu Lys Asp Gly Gly Ser
        115                 120                 125

Gly Gly Val Ser Ser Val Pro Thr Asn Leu Glu Val Val Ala Ala Thr
130                 135                 140

Pro Thr Ser Leu Leu Ile Ser Trp Asp Ala Phe Thr Asp Leu Pro Val
145                 150                 155                 160

Arg Tyr Tyr Arg Ile Thr Tyr Gly Glu Thr Gly Gly Asn Ser Pro Val
                165                 170                 175

Gln Glu Phe Thr Val Pro Gly Ser Lys Ser Thr Ala Thr Ile Ser Gly
            180                 185                 190

Leu Lys Pro Gly Val Asp Tyr Thr Ile Thr Val Tyr Ala His Tyr Asn
        195                 200                 205

Tyr His Tyr Tyr Ser Ser Pro Ile Ser Ile Asn Tyr Arg Thr
210                 215                 220

<210> SEQ ID NO 164
```

```
<211> LENGTH: 14
<212> TYPE: PRT
<213> ORGANISM: Artificial Sequence
<220> FEATURE:
<223> OTHER INFORMATION: Synthetic peptide

<400> SEQUENCE: 164

Asn Glu Pro Leu Pro Tyr Leu Asn Thr Phe Ala Asn Thr Cys
1               5                   10

<210> SEQ ID NO 165
<211> LENGTH: 94
<212> TYPE: PRT
<213> ORGANISM: Artificial Sequence
<220> FEATURE:
<223> OTHER INFORMATION: Synthetic peptide

<400> SEQUENCE: 165

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Tyr Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 166
<211> LENGTH: 103
<212> TYPE: PRT
<213> ORGANISM: Artificial Sequence
<220> FEATURE:
<223> OTHER INFORMATION: Synthetic peptide

<400> SEQUENCE: 166

Gly Ser His Met Gly His Glu Leu Ala Lys Gln Glu Ile Arg Val Arg
1               5                   10                  15

Val Glu Lys Asp Pro Glu Leu Gly Phe Ser Ile Ser Gly Gly Val Gly
            20                  25                  30

Gly Arg Gly Asn Pro Phe Arg Pro Asp Asp Gly Ile Phe Val Thr
        35                  40                  45

Arg Val Gln Pro Glu Gly Pro Ala Ser Lys Leu Leu Gln Pro Gly Asp
    50                  55                  60

Lys Ile Ile Gln Ala Asn Gly Tyr Ser Phe Ile Asn Ile Glu His Gly
65                  70                  75                  80

Gln Ala Val Ser Leu Leu Lys Thr Phe Gln Asn Thr Val Glu Leu Ile
                85                  90                  95

Ile Val Arg Glu Val Ser Ser
            100

<210> SEQ ID NO 167
<211> LENGTH: 19
<212> TYPE: PRT
<213> ORGANISM: Artificial Sequence
<220> FEATURE:
<223> OTHER INFORMATION: Synthetic peptide

<400> SEQUENCE: 167
```

```
Met Lys Lys Ile Trp Leu Ala Leu Ala Gly Leu Val Leu Ala Phe Ser
1               5                   10                  15

Ala Ser Ala
```

<210> SEQ ID NO 168
<211> LENGTH: 8
<212> TYPE: PRT
<213> ORGANISM: Artificial Sequence
<220> FEATURE:
<223> OTHER INFORMATION: Synthetic peptide

<400> SEQUENCE: 168

```
Pro Gln Pro Val Asp Ser Trp Val
1               5
```

<210> SEQ ID NO 169
<211> LENGTH: 225
<212> TYPE: PRT
<213> ORGANISM: Artificial Sequence
<220> FEATURE:
<223> OTHER INFORMATION: Synthetic peptide

<400> SEQUENCE: 169

```
Met Lys His His His His His His His Ser Ser Asp Tyr
1               5                   10                  15

Lys Asp Asp Asp Lys Gly Glu Asn Leu Tyr Phe Gln Gly Ser Pro
            20                  25                  30

Glu Leu Gly Phe Ser Ile Ser Gly Val Gly Gly Arg Gly Asn Pro
            35                  40                  45

Phe Arg Pro Asp Asp Asp Gly Ile Phe Val Thr Arg Val Gln Pro Glu
        50                  55                  60

Gly Pro Ala Ser Lys Leu Leu Gln Pro Gly Asp Lys Ile Ile Gln Ala
65                  70                  75                  80

Asn Gly Tyr Ser Phe Ile Asn Ile Glu His Gly Gln Ala Val Ser Leu
                85                  90                  95

Leu Lys Thr Phe Gln Asn Thr Val Glu Leu Ile Ile Val Arg Glu Val
            100                 105                 110

Gly Asn Gly Ala Lys Gln Glu Ile Arg Val Arg Val Glu Lys Asp Gly
            115                 120                 125

Gly Ser Gly Gly Val Ser Ser Val Pro Thr Asn Leu Glu Val Val Ala
        130                 135                 140

Ala Thr Pro Thr Ser Leu Leu Ile Ser Trp Asp Ala Ser Tyr Gly Val
145                 150                 155                 160

Val Ser Tyr Tyr Arg Ile Thr Tyr Gly Glu Thr Gly Gly Asn Ser Pro
                165                 170                 175

Val Gln Glu Phe Thr Val Pro Tyr Ser Ser Thr Ala Thr Ile Ser
            180                 185                 190

Gly Leu Lys Pro Gly Val Asp Tyr Thr Ile Thr Val Tyr Ala Tyr Ser
            195                 200                 205

Asp Tyr Tyr Gly Ser His His Tyr Ser Pro Ile Ser Ile Asn Tyr Arg
        210                 215                 220

Thr
225
```

<210> SEQ ID NO 170
<211> LENGTH: 224
<212> TYPE: PRT
<213> ORGANISM: Artificial Sequence
<220> FEATURE:
<223> OTHER INFORMATION: Synthetic peptide

<400> SEQUENCE: 170

```
Met Lys His His His His His His His His Ser Ser Asp Tyr
1               5                   10                  15

Lys Asp Asp Asp Lys Gly Glu Asn Leu Tyr Phe Gln Gly Ser Pro
            20                  25                  30

Glu Leu Gly Phe Ser Ile Ser Gly Val Gly Gly Arg Gly Asn Pro
        35                  40                  45

Phe Arg Pro Asp Asp Asp Gly Ile Phe Val Thr Arg Val Gln Pro Glu
    50                  55                  60

Gly Pro Ala Ser Lys Leu Leu Gln Pro Gly Asp Lys Ile Ile Gln Ala
65                  70                  75                  80

Asn Gly Tyr Ser Phe Ile Asn Ile Glu His Gly Gln Ala Val Ser Leu
                85                  90                  95

Leu Lys Thr Phe Gln Asn Thr Val Glu Leu Ile Ile Val Arg Glu Val
                100                 105                 110

Gly Asn Gly Ala Lys Gln Glu Ile Arg Val Arg Val Glu Lys Asp Gly
            115                 120                 125

Gly Ser Gly Gly Val Ser Ser Val Pro Thr Asn Leu Glu Val Val Ala
        130                 135                 140

Ala Thr Pro Thr Ser Leu Leu Ile Ser Trp Asp Ala Tyr Tyr Asp Ser
145                 150                 155                 160

His Val Ser Tyr Tyr Arg Ile Thr Tyr Gly Glu Thr Gly Gly Asn Ser
                165                 170                 175

Pro Val Gln Glu Phe Thr Val Pro Gly Ser Lys Ser Thr Ala Thr Ile
            180                 185                 190

Ser Gly Leu Lys Pro Gly Val Asp Tyr Thr Ile Thr Val Tyr Ala His
        195                 200                 205

Tyr Asn Tyr His Tyr Tyr Ser Ser Pro Ile Ser Ile Asn Tyr Arg Thr
    210                 215                 220
```

<210> SEQ ID NO 171
<211> LENGTH: 223
<212> TYPE: PRT
<213> ORGANISM: Artificial Sequence
<220> FEATURE:
<223> OTHER INFORMATION: Synthetic peptide

<400> SEQUENCE: 171

```
Met Lys His His His His His His His His Ser Ser Asp Tyr
1               5                   10                  15

Lys Asp Asp Asp Lys Gly Glu Asn Leu Tyr Phe Gln Gly Ser Pro
            20                  25                  30

Glu Leu Gly Phe Ser Ile Ser Gly Val Gly Gly Arg Gly Asn Pro
        35                  40                  45

Phe Arg Pro Asp Asp Asp Gly Ile Phe Val Thr Arg Val Gln Pro Glu
    50                  55                  60

Gly Pro Ala Ser Lys Leu Leu Gln Pro Gly Asp Lys Ile Ile Gln Ala
65                  70                  75                  80

Asn Gly Tyr Ser Phe Ile Asn Ile Glu His Gly Gln Ala Val Ser Leu
                85                  90                  95

Leu Lys Thr Phe Gln Asn Thr Val Glu Leu Ile Ile Val Arg Glu Val
                100                 105                 110
```

```
Gly Asn Gly Ala Lys Gln Glu Ile Arg Val Arg Val Glu Lys Asp Gly
            115                 120                 125

Gly Ser Gly Gly Val Ser Val Pro Thr Asn Leu Glu Val Val Ala
        130                 135                 140

Ala Thr Pro Thr Ser Leu Leu Ile Ser Trp Asp Ala Tyr Arg Glu Leu
145                 150                 155                 160

Pro Val Ser Tyr Tyr Arg Ile Thr Tyr Gly Glu Thr Gly Gly Asn Ser
            165                 170                 175

Pro Val Gln Glu Phe Thr Val Pro Gly Ser Lys Ser Thr Ala Thr Ile
                180                 185                 190

Ser Gly Leu Lys Pro Gly Asp Tyr Thr Ile Thr Val Tyr Ala His Tyr
            195                 200                 205

Asn Tyr His Tyr Tyr Ser Ser Pro Ile Ser Ile Asn Tyr Arg Thr
            210                 215                 220

<210> SEQ ID NO 172
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: k = Lys is methylated

<400> SEQUENCE: 172

Ala Arg Thr Lys Gln Thr Ala Arg Lys Ser Thr Gly Gly Lys Ala Pro
1               5                   10                  15

Gly Tyr Cys Asp
            20

<210> SEQ ID NO 173
<211> LENGTH: 14
<212> TYPE: PRT
<213> ORGANISM: Artificial Sequence
<220> FEATURE:
<223> OTHER INFORMATION: Synthetic peptide

<400> SEQUENCE: 173

Ser Asn Cys Arg His Asn Thr Gly Tyr Asn Ser Cys Ser Arg
1               5                   10

<210> SEQ ID NO 174
<211> LENGTH: 14
<212> TYPE: PRT
<213> ORGANISM: Artificial Sequence
<220> FEATURE:
<223> OTHER INFORMATION: Synthetic peptide

<400> SEQUENCE: 174

Asn Phe Cys Ala Ser Asn Gly Thr Gly Asn Asp Cys Arg Arg
1               5                   10
```